United States Patent
Wang et al.

(10) Patent No.: US 11,845,970 B2
(45) Date of Patent: Dec. 19, 2023

(54) ENDO-S2 MUTANTS AS GLYCOSYNTHASES, METHOD OF MAKING AND USE FOR GLYCOENGINEERING OF GLYCOPROTEINS

(71) Applicant: UNIVERSITY OF MARYLAND, COLLEGE PARK, College Park, MD (US)

(72) Inventors: Lai-Xi Wang, Ellicott City, MD (US); Qiang Yang, Ellicott City, MD (US); Tiezheng Li, Columbia, MD (US); Xin Tong, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 111 days.

(21) Appl. No.: 17/320,703

(22) Filed: May 14, 2021

(65) Prior Publication Data

US 2021/0269841 A1 Sep. 2, 2021

Related U.S. Application Data

(63) Continuation of application No. 16/069,216, filed as application No. PCT/US2017/013734 on Jan. 17, 2017, now Pat. No. 11,008,601.

(60) Provisional application No. 62/279,087, filed on Jan. 15, 2016.

(51) Int. Cl.
| | |
|---|---|
| C12P 21/00 | (2006.01) |
| C07K 16/28 | (2006.01) |
| C07K 16/32 | (2006.01) |
| A61K 47/54 | (2017.01) |
| C12N 9/24 | (2006.01) |
| A61P 31/18 | (2006.01) |
| A61P 35/00 | (2006.01) |

(52) U.S. Cl.
CPC .......... *C12P 21/005* (2013.01); *A61K 47/549* (2017.08); *C07K 16/2887* (2013.01); *C07K 16/32* (2013.01); *C12N 9/2402* (2013.01); *C12Y 302/01096* (2013.01); *A61P 31/18* (2018.01); *A61P 35/00* (2018.01); *C07K 2317/41* (2013.01)

(58) Field of Classification Search
None
See application file for complete search history.

(56) References Cited

U.S. PATENT DOCUMENTS

| | | | |
|---|---|---|---|
| 7,524,821 B2 | 4/2009 | Wang et al. | |
| 7,556,809 B2 | 7/2009 | Wang | |
| 7,604,804 B2 | 10/2009 | Wang et al. | |
| 7,728,106 B2 | 6/2010 | Wang | |
| 7,807,405 B2 | 10/2010 | Wang | |
| 8,354,247 B2 | 1/2013 | Wang | |
| 8,900,826 B2 | 12/2014 | Wang | |
| 9,175,326 B2 | 11/2015 | Wang | |
| 9,434,786 B2 | 9/2016 | Wang et al. | |
| 9,493,752 B2 | 11/2016 | Collin et al. | |
| 9,605,050 B2 | 3/2017 | Wang | |
| 9,845,360 B2 | 12/2017 | Wang et al. | |
| 9,850,473 B2 | 12/2017 | Wang | |
| 2015/0087814 A1 | 3/2015 | Wang et al. | |
| 2015/0176045 A1 | 6/2015 | Marcel et al. | |
| 2019/0002542 A1 | 1/2019 | Wang et al. | |
| 2019/0002945 A1 | 1/2019 | Wang et al. | |

FOREIGN PATENT DOCUMENTS

| | | |
|---|---|---|
| JP | 2014531205 A | 11/2014 |
| JP | 2017-012152 A | 3/2016 |
| WO | WO2013120066 | 8/2013 |
| WO | WO2015057066 | 4/2015 |

OTHER PUBLICATIONS

Klontz,E.K., et al Moleculare Basis of Broad Spectrum N-Glycan Specificity (2019) ACE Cent. Sci. 5: 524-538.
Adams, G. P. et al. Monoclonal antibody therapy of cancer. *Nat. Biotechnol.* (2005) 23:1147-1157.
Aggarwal, S. R. What's fueling the biotech engine—2011 to 2012. *Nat. Biotechnol.* (2012) 30:1191-1197.
Aggarwal, S. R. A survey of breakthrough therapy designations. *Nat. Biotechnol.* (2014) 32:323-330.
Allhorn, M. et al. EndoS from *Streptococcus pyogenes* is hydrolyzed by the cysteine proteinase SpeB and requires glutamic acid 235 and tryptophans for IgG glycan-hydrolyzing activity. *BMC Microbiol* (2008), 8:3.
Anthony, R. M. et al. Recapitulation of IVIG anti-inflammatory activity with a recombinant IgG Fc. *Science* (2008) 320:373-376.
Cartron, G. et al. Therapeutic activity of humanized anti-CD20 monoclonal antibody and polymorphism in IgG Fc receptor FcgammaRIIIa gene. *Blood* (2002) 99:754-758.

(Continued)

Primary Examiner — Kagnew H Gebreyesus
(74) Attorney, Agent, or Firm — Carter, Deluca & Farrell LLP; George Likourezos

(57) ABSTRACT

The present invention provides for recombinant Endo-S2 mutants (named Endo-S2 glycosynthases) that exhibit reduced hydrolysis activity and increased transglycosylation activity for the synthesis of glycoproteins wherein a desired sugar chain is added to a fucosylated or nonfucosylated GlcNAc-IgG acceptor. As such, the present invention allows for the synthesis and remodeling of therapeutic antibodies thereby providing for certain biological activities, such as, prolonged half-life time in vivo, less immunogenicity, enhanced in vivo activity, increased targeting ability, and/or ability to deliver a therapeutic agent.

12 Claims, 18 Drawing Sheets

Specification includes a Sequence Listing.

(56) References Cited

OTHER PUBLICATIONS

Collin, M. et al. "EndoS, a novel secreted protein from *Streptococcus pyogenes* with endoglycosidase activity on human IgG", *The EMBO Journal*, (2001) 20(12), : 3046-3055.
Cox, K. M. et al. Glycan optimization of a human monoclonal antibody in the aquatic plant *Lemna minor*. *Nat. Biotechnol.* (2006) 24:1591-1597.
Dalziel, M. et al. Emerging principles for the therapeutic exploitation of glycosylation. *Science* (2014) 343:1235681.
Fan, S. Q. et al. Remarkable transglycosylation activity of glycosynthase mutants of Endo-D, an endo-beta-N-acetylglucosaminidase from *Streptococcus pneumoniae*. *J. Biol. Chem.* (2012) 287:11272-11281.
Garrido, D. et al. "Endo-beta-N-acetylglucosaminidases from infant gut-associated bifidobacteria release complex N-glycans from human milk glycoproteins", *Molecular and Cellular Proteomics*, (2012) 11(9);775-785.
Giddens, J. P. et al. Chemoenzymatic Glyco-engineering of Monoclonal Antibodies. *Methods Mol. Biol.* (2015) 1321:375-387.
Giddens, J. P. et al. Endo-F3 Glycosynthase Mutants Enable Chemoenzymatic Synthesis of Core-fucosylated Triantennary Complex Type Glycopeptides and Glycoproteins. *J. Biol. Chem.* (2016) 291:9356-9370.
Huang, W. et al. Chemoenzymatic glycoengineering of intact IgG antibodies for gain of functions. *J. Am. Chem. Soc.* (2012) 134:12308-12318.
Huang, W. et al. Glycosynthases enable a highly efficient chemoenzymatic synthesis of N-glycoproteins carrying intact natural N-glycans. *J. Am. Chem. Soc.* (2009) 131:2214-2223.
Huang, W. et al. Arthrobacter endobeta-N-acetylglucosaminidase shows transglycosylation activity on complex-type N-glycan oxazolines: one-pot conversion of ribonuclease B to sialylated ribonuclease C. *ChemBioChem* (2010) 11:1350-1355.
Illidge, T. et al. Update on obinutuzumab in the treatment of B-cell malignancies. *Expert Opin. Biol. Ther.* (2014) 14:1507-1517.
Jefferis, R. Glycosylation as a strategy to improve antibody-based therapeutics. *Nat. Rev.Drug Discov.* (2009) 8:226-234.
Kaneko, Y. et al. Anti-inflammatory activity of immunoglobulin G resulting from Fc sialylation. *Science* (2006) 313:670-673.
Kurogochi, M. et al. Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities. *PLoS One* (2015) 10:e0132848.
Le, N. P. et al. Immune recruitment or suppression by glycan engineering of endogenous and therapeutic antibodies. *Biochim. Biophys. Acta.* (2016) 1860:1655-1668.
Li, T. et al. Glycosynthase mutants of endoglycosidase S2 show potent transglycosylation activity and remarkably relaxed substrate specificity for antibody glycosylation remodeling, *Journal of Biological Chemistry*, (2016) 291(32):16508-16518.
Li, H. et al. Optimization of humanized IgGs in glycoengineered Pichia pastoris. *Nat. Biotechnol.* (2006) 24:210-215.
Lin, C. W. et al. A common glycan structure on immunoglobulin G for enhancement of effector functions. *Proc. Natl. Acad. Sci. USA* (2015) 112:10611-10616.
Liu, R. et al. Evaluation of a glycoengineered monoclonal antibody via LC-MS analysis in combination with multiple enzymatic digestion. *MAbs* (2016) 8:340-346.
Niwa, R. et al. Defucosylated chimeric anti-CC chemokine receptor 4 IgG1 with enhanced antibody-dependent cellular cytotoxicity shows potent therapeutic activity to T-cell leukemia and lymphoma. *Cancer Res.* (2004) 64:2127-2133.
Park, J. E. Expression and characterization of beta-1,4-galactosyltransferase from Neisseria meningitidis and Neisseria gonorrhoeae. *J. Biochem. Mol. Biol.* (2002) 35: 330-336.
Parsons, T. B. Optimal Synthetic Glycosylation of a Therapeutic Antibody. *Angew. Chem. Int. Ed.* (2016) 55:2361-2367.

Quast I. et al. Sialylation of IgG Fc domain impairs complement-dependent cytotoxicity. *J. Clin. Invest.* (2015) 125:4160-4170.
Rodriguez-Diaz, J. et al. Utilization of natural fucosylated oligosaccharides by three novel alpha-L-fucosidases from a probiotic *Lactobacillus casei* strain. *Appl. Environ. Microbiol.* (2011) 77:703-705.
Saribas, A. S. et al. Refolding of human beta-1-2 GlcNAc transferase (GnTI) and the role of its unpaired Cys 121. Biochem. Biophys. Res. Commun. (2007) 362:381-386.
Schwab, I. et al. Broad requirement for terminal sialic acid residues and FcgammaRIIB for the preventive and therapeutic activity of intravenous immunoglobulins in vivo. *Eur. J. Immunol.* (2014) 44:1444-1453.
Shields, R. L. et al. Lack of fucose on human IgG1 N-linked oligosaccharide improves binding to human Fcgamma RIII and antibody-dependent cellular toxicity. *J. Biol. Chem.* (2002) 277:26733-26740.
Shen, A. et al. Simplified, enhanced protein purification using an inducible, autoprocessing enzyme tag. *PloS One* (2009) 4:e8119.
Sjorgren, J. et al. EndoS2 is a unique and conserved enzyme of serotype M49 group A *Streptococcus* that hydrolyses N-linked glycans on IgG and alpha1-acid glycoprotein. *Biochem. J.* (2013) 455:107-118.
Sjorgren, J. et al. EndoS and EndoS2 hydrolyze Fc-glycans on therapeutic antibodies with different glycoform selectivity and can be used for rapid quantification of high-mannose glycans. *Glycobiology* (2015) 25:1053-1063.
Stanley, P. et al. Molecular analysis of three gain-offunction CHO mutants that add the bisecting GlcNAc to N-glycans. *Glycobiology* (2005) 15:43-53.
Strasser, R. et al. Improved virus neutralization by plant-produced anti-HIV antibodies with a homogeneous beta1,4-galactosylated N-glycan profile. *J. Biol. Chem.* (2009) 284:20479-20485.
Strome, S.E. et al. A mechanistic perspective of monoclonal antibodies in cancer therapy beyond target-related effects. *Oncologist* (2007) 12:1084-1095.
Umana, P. et al. Engineered glycoforms of an antineuroblastoma IgG1 with optimized antibody-dependent cellular cytotoxic activity. *Nat. Biotechnol.* (1999) 17:176-180.
Umekawa, M. et al. Mutants of Mucor hiemalis endo-beta-N-acetylglucosaminidase show enhanced transglycosylation and glycosynthase-like activities. *J. Biol. Chem.* (2008) 283:4469-4479.
Umekawa, M. et al. Efficient glycosynthase mutant derived from Mucor hiemalis endo-beta-Nacetylglucosaminidase capable of transferring oligosaccharide from both sugar oxazoline and natural N-glycan. *J. Biol. Chem.* (2010) 285:511-521.
Van de Bovenkamp, F. S. et al . The Emerging Importance of IgG Fab Glycosylation in Immunity. *J. Immunol.* (2016) 196:1435-1441.
Wang, L. X. et al. Chemical and chemoenzymatic synthesis of glycoproteins for deciphering functions. *Chem. Biol.* (2014) 21:51-66.
Wang, L. X. et al. Binding of high-mannose-type oligosaccharides and synthetic oligomannose clusters to human antibody 2G12: implications for HIV-1 vaccine design. *Chem. Biol.* (2004) 11:127-134.
Washburn, N. et al. Controlled tetra-Fc sialylation of IVIg results in a drug candidate with consistent enhanced anti-inflammatory activity. *Proc. Natl. Acad. Sci. USA* (2015) 112:E1297-1306.
Wei, Y. et al. Glycoengineering of human IgG1-Fc through combined yeast expression and in vitro chemoenzymatic glycosylation. *Biochemistry* (2008) 47:10294-10304.
Yamane-Ohnuki, N. Establishment of FUT8 knockout Chinese hamster ovary cells: an ideal host cell line for producing completely defucosylated antibodies with enhanced antibody-dependent cellular cytotoxicity. *Biotechnol. Bioeng.* (2004) 87: 614-622.
Takashima, A. et al. Glycoengineered Trastuzumab with Homogeneous Glycan (5)-Transglycosylation Activity of Endo-S2 Mutants, Abstracts of the 34th Annual Meeting of the Japanese Society of Carbohydrate Research, Jul. 1, 2015, p. 171,P-015.
Takashima, A. et al. Analysis of Enzymatic Properties of Endo-S2 Mutants, Abstracts of the Joint Meeting of the 38th Annual Meeting of the Molecular Biology Society of Japan and the 88th Annual Meeting of the Japanese Biochemical Society, Dec. 3, 2015, 3P0283 (4T13L-12).

(56) References Cited

OTHER PUBLICATIONS

Japanese Office Action, corresponding to Japanese Patent Application No. 2018-537508, dated Oct. 13, 2020.
Yu, H. et al. Highly efficient chemoenzymatic synthesis of naturally occurring and extremely flexible donor-substrate specificity. *Angew. Chem. Int. Ed.* (2006) 45: 3938-3944.
Zhou, Q. Development of a simple and rapid method for producing non-fucosylated oligomannose containing antibodies with increased effector function. *Biotechnol. Bioeng.* (2008) 99:652-665.
Zou, G. et al. Chemoenzymatic synthesis and Fcgamma receptor binding of homogeneous glycoforms of antibody Fc domain. Presence of a bisecting sugar moiety enhances the affinity of Fc to FcgammaIIIa receptor. *J. Am. Chem. Soc.* (2011) 133:18975-18991.
Bhattacharya R., Impact of genetice variation on three dimension (2017) PLOS ONE 12(3) 1-22.
ACI61688.1, McShan et al., GenBank (2008).
Japanese Office Action, corresponding to Japanese Patent Application No. 2021-172794, dated Oct. 28, 2022 (English Translation).

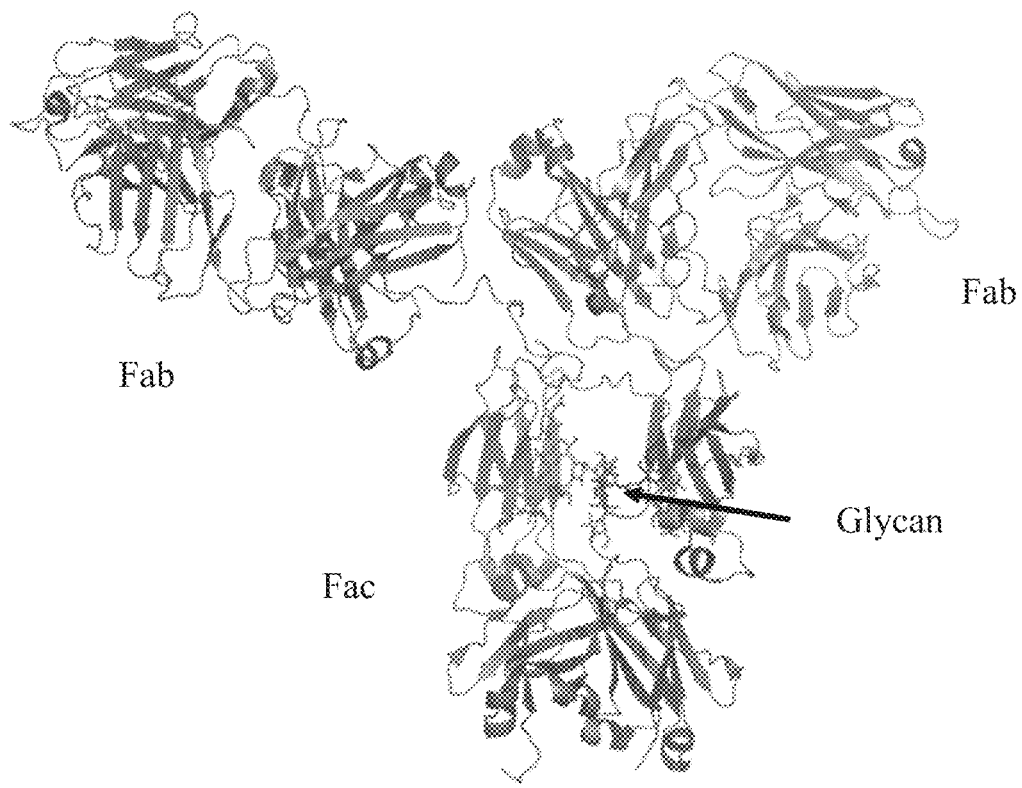
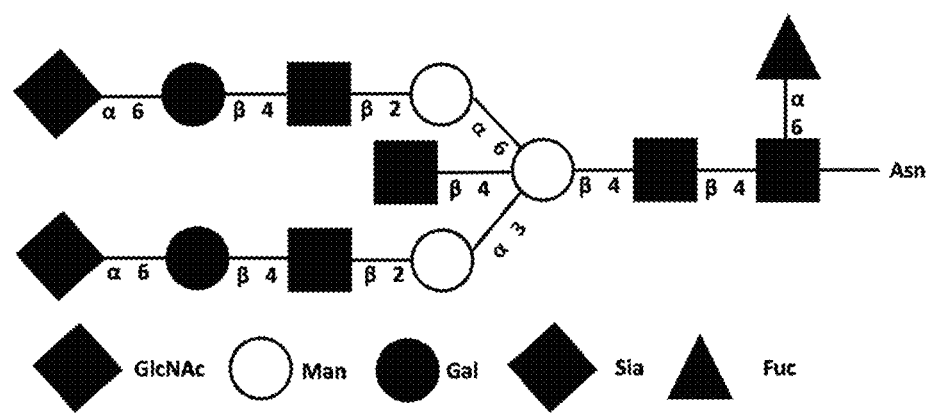
Figure 1

```
Endo S2  WHDRASTGIDGKQQHPENTMAEVPKEVDILFVFHDHTASDSFFWSELKDSYVHKLHQQGT  133
Endo S   WHDKTSDPT---EKDKVNSMGELPKEVDLAFIFHDWTKDYSLFWKELATKHVEKLNKQGT  177
         ***::*:*    *:** ***:***:**:***:*** **:***:*:***:*::**::**

Endo S2  ALVQTIGVNELNGR------TGLSKDYPDTPEGNKALPAARIVKAFVTDRGVDGLDIDIE  188
Endo S   RVIRTIPWRFLAGGDNSGIAEDTSKYENTPEGNKALAKAIVDEYVYKYNLDGLDVDVE   237
         ::::**  ::* *        :. ** :**********.**:*::* ::*:*****:*

Endo S2  FTNKRTPEE----DARALNVFKEIAQLIGKNGSDKSKLLINDTTLSVENNPIFKGIAEDL  244
Endo S   SIPKVDKKEDTAGVERSIQVFEEIGKLIGPKGVDKSRLFIMDSTYMADKNPLIERGAPYI  297
         .. :..::*    . **:**:**.:**:.*.***:*:*:*:* .:::**:*:.*. :
```

Figure 2

SEQUENCE LISTING

```
<160> NUMBER OF SEQ ID NOS: 24

<210> SEQ ID NO 1
<211> LENGTH: 843
<212> TYPE: PRT
<213> ORGANISM: Streptococcus pyogenes

<400> SEQUENCE: 1

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asp Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
```

```
            260                 265                 270
Asn Tyr Ile Asp Ala Ser Gln Phe Met Ile Gly Phe Ser Phe Phe Glu
            275                 280                 285
Glu Ser Ala Ser Lys Gly Asn Leu Trp Phe Asp Val Asn Glu Tyr Asp
            290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
                340                 345                 350
Tyr Lys Asn Arg Thr Ser Thr Asn Leu Gln Arg His Glu Val Asp Asn
                355                 360                 365
Ile Ser His Thr Asp Tyr Thr Val Ser Arg Lys Leu Lys Thr Leu Met
            370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
                420                 425                 430
Gln Asn Leu Lys Gly Leu Glu Lys Leu Ser Lys Leu Gln Lys Leu Glu
            435                 440                 445
Leu Arg Gln Leu Ser Asn Val Lys Glu Ile Thr Pro Glu Leu Leu Pro
            450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
                500                 505                 510
Asn Ser Leu Asp Leu Ser Glu Lys Ser Glu Asp Arg Lys Leu Leu Met
            515                 520                 525
Thr Leu Met Glu Gln Val Ser Asn His Gln Lys Ile Thr Val Lys Asn
            530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
                580                 585                 590
Gly Asp Glu Glu Ala Phe Ala Ile Tyr Lys Glu Gly Ala Val Asp Gly
                595                 600                 605
Arg Gln Tyr Val Ser Lys Asp Tyr Thr Tyr Glu Ala Phe Arg Lys Asp
            610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
                645                 650                 655
Val Ser Asp Gly Glu Lys Val Val His His Met Lys Leu Asn Ile Gly
                660                 665                 670
Ser Gly Ala Ile Met Met Glu Asn Leu Ala Lys Gly Ala Lys Val Ile
            675                 680                 685
```

-continued

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Lys Asp
        835                 840

<210> SEQ ID NO 2
<211> LENGTH: 843
<212> TYPE: PRT
<213> ORGANISM: Artificial Sequence
<220> FEATURE:
<223> OTHER INFORMATION: Synthetic Construct

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Ala Ile Glu His Glu Phe Thr Asn Lys
            180                 185                 190

Arg Thr Pro Glu Glu Asp Ala Arg Ala Leu Asn Val Phe Lys Glu Ile
        195                 200                 205

```
Ala Gln Leu Ile Gly Lys Asn Gly Ser Asp Lys Ser Lys Leu Leu Ile
    210                 215                 220
Met Asp Thr Thr Leu Ser Val Glu Asn Asn Pro Ile Phe Lys Gly Ile
225                 230                 235                 240
Ala Glu Asp Leu Asp Tyr Leu Leu Arg Gln Tyr Tyr Gly Ser Gln Gly
                245                 250                 255
Gly Glu Ala Glu Val Asp Thr Ile Asn Ser Asp Trp Asn Gln Tyr Gln
            260                 265                 270
Asn Tyr Ile Asp Ala Ser Gln Phe Met Ile Gly Phe Ser Phe Phe Glu
        275                 280                 285
Glu Ser Ala Ser Lys Gly Asn Leu Trp Phe Asp Val Asn Glu Tyr Asp
    290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
            340                 345                 350
Tyr Lys Asn Arg Thr Ser Thr Asn Leu Gln Arg His Glu Val Asp Asn
        355                 360                 365
Ile Ser His Thr Asp Tyr Thr Val Ser Arg Lys Leu Lys Thr Leu Met
    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
            420                 425                 430
Gln Asn Leu Lys Gly Leu Glu Lys Leu Ser Leu Gln Lys Leu Glu
        435                 440                 445
Leu Arg Gln Leu Ser Asn Val Lys Glu Ile Thr Pro Glu Leu Leu Pro
    450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
        515                 520                 525
Thr Leu Met Glu Gln Val Ser Asn His Gln Lys Ile Thr Val Lys Asn
    530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
```

```
Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
            645                 650                 655

Val Ser Asp Gly Glu Lys Val Val His His Met Lys Leu Asn Ile Gly
        660                 665                 670

Ser Gly Ala Ile Met Met Glu Asn Leu Ala Lys Gly Ala Lys Val Ile
    675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 3
<211> LENGTH: 843
<212> TYPE: PRT
<213> ORGANISM: Artificial Sequence
<220> FEATURE:
<223> OTHER INFORMATION: Synthetic Construct

<400> SEQUENCE: 3

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
            85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140
```

```
Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Asn Ile Glu His Glu Phe Thr Asn Lys
                180                 185                 190

Arg Thr Pro Glu Glu Asp Ala Arg Ala Leu Asn Val Phe Lys Glu Ile
                195                 200                 205

Ala Gln Leu Ile Gly Lys Asn Gly Ser Asp Lys Ser Lys Leu Leu Ile
                210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Glu
                275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
                355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
                435                 440                 445

Leu Arg Gln Leu Ser Asn Val Lys Glu Ile Thr Pro Glu Leu Leu Pro
                450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
                515                 520                 525

Thr Leu Met Glu Gln Val Ser Asn His Gln Lys Ile Thr Val Lys Asn
                530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
```

```
            565                 570                 575
Leu Thr Asp Phe Val Phe Gly Thr Val Thr Lys Arg Asn Thr Phe Ile
            580                 585                 590

Gly Asp Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
        820                 825                 830

Leu Ser Asn Asp Val Ala Asn Thr Leu Lys Asp
        835                 840

<210> SEQ ID NO 4
<211> LENGTH: 843
<212> TYPE: PRT
<213> ORGANISM: Artificial Sequence
<220> FEATURE:
<223> OTHER INFORMATION: Synthetic Construct

<400> SEQUENCE: 4

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
```

```
                    85                  90                  95
Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Gln Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
        210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510
```

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
            530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
            565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
            610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
            645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
            725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
            805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
            835                 840

<210> SEQ ID NO 5
<211> LENGTH: 843
<212> TYPE: PRT
<213> ORGANISM: Artificial Sequence
<220> FEATURE:
<223> OTHER INFORMATION: Synthetic Construct

<400> SEQUENCE: 5

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

```
Thr Val Lys Ala Glu Lys Thr Val Gln Thr Gly Lys Thr Asp Gln
        35                  40                  45

Gln Val Gly Ala Lys Leu Val Gln Glu Ile Arg Glu Gly Lys Arg Gly
50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Arg Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
        210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
        370                 375                 380

Thr Glu Asp Lys Arg Tyr Asp Val Ile Asp Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445
```

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 6
<211> LENGTH: 843
<212> TYPE: PRT

<213> ORGANISM: Artificial Sequence
<220> FEATURE:
<223> OTHER INFORMATION: Synthetic Construct

<400> SEQUENCE: 6

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp Thr Ala Ser
            100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Cys Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
```

```
            385                 390                 395                 400

Pro Ala Leu Arg Glu Gln Ile Ile Gln Gln Val Gly Gln Tyr Lys Gly
                    405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
        450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                    485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
        530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                    565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                    645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                    725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
        770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                    805                 810                 815
```

Ser Ser Tyr Tyr Pro Gln Tyr Thr Glu Leu Gln Ile Leu Gly Gln Arg
                820                 825                 830

Leu Ser Asn Asp Val Ala Asn Thr Leu Lys Asp
        835                 840

<210> SEQ ID NO 7
<211> LENGTH: 843
<212> TYPE: PRT
<213> ORGANISM: Artificial Sequence
<220> FEATURE:
<223> OTHER INFORMATION: Synthetic Construct

<400> SEQUENCE: 7

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ala Ile Val Lys Ala Phe Val Thr Asp Arg
                165                 170                 175

Gly Val Asp Gly Leu Asp Ile Met Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

```
Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
                645                 650                 655

Val Ser Asp Gly Glu Lys Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750
```

```
Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Lys Asp
        835                 840
```

<210> SEQ ID NO 8
<211> LENGTH: 843
<212> TYPE: PRT
<213> ORGANISM: Artificial Sequence
<220> FEATURE:
<223> OTHER INFORMATION: Synthetic Construct

<400> SEQUENCE: 8

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65              70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Glu Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270
```

-continued

```
Asn Tyr Ile Asp Ala Ser Gln Phe Met Ile Gly Phe Ser Phe Glu
            275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
```

```
                    690                 695                 700
Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                    725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
                755                 760                 765

Asp Ile Lys Asn Arg Lys Glu Tyr Leu Ser Asn Asp Glu Asn Trp Thr
            770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                    805                 810                 815

Ser Ser Tyr Tyr Pro Gln Tyr Thr Glu Leu Gln Ile Leu Gly Gln Arg
                820                 825                 830

Leu Ser Asn Asp Val Ala Asn Thr Leu Lys Asp
                835                 840
```

<210> SEQ ID NO 9
<211> LENGTH: 843
<212> TYPE: PRT
<213> ORGANISM: Artificial Sequence
<220> FEATURE:
<223> OTHER INFORMATION: Synthetic Construct

<400> SEQUENCE: 9

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45

Gln Val Gly Ala Lys Leu Val Gln Glu Ile Arg Glu Gly Lys Arg Gly
        50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ala Ile Val Lys Ala Phe Val Thr Asp Arg
                165                 170                 175

Gly Val Asp Gly Leu Asp Ile Gly Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
```

```
            210                 215                 220
Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                    245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Phe Glu
            275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                    325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
            355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                    405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                    485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                    565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640
```

```
Val Thr Ser Lys Val Thr Ala Thr Thr Asp Glu Thr Tyr Leu Val Asp
            645                 650                 655

Val Ser Asp Gly Glu Lys Val Val His His Met Lys Leu Asn Ile Gly
        660                 665                 670

Ser Gly Ala Ile Met Met Glu Asn Leu Ala Lys Gly Ala Lys Val Ile
    675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 10
<211> LENGTH: 843
<212> TYPE: PRT
<213> ORGANISM: Artificial Sequence
<220> FEATURE:
<223> OTHER INFORMATION: Synthetic Construct

<400> SEQUENCE: 10

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160
```

```
Asn Lys Ala Leu Ala Ala Ile Val Lys Ala Phe Val Thr Asp Arg
            165                 170                 175

Gly Val Asp Gly Leu Asp Ile His Ile Glu His Glu Phe Thr Asn Lys
        180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
        260                 265                 270

Asn Tyr Ile Asp Ala Ser Gln Phe Met Ile Gly Phe Ser Phe Phe Glu
    275                 280                 285

Glu Ser Ala Ser Lys Gly Asn Leu Trp Phe Asp Val Asn Glu Tyr Asp
        290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
            325                 330                 335

Phe Ser Tyr Ala Ile Asp Arg Asp Gly Val Ala His Val Pro Ser Thr
        340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415

Asp Leu Glu Arg Tyr Asn Lys Thr Leu Val Leu Thr Gly Asp Lys Ile
        420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
        500                 505                 510

Asn Ser Leu Asp Leu Ser Glu Lys Ser Glu Asp Arg Lys Leu Leu Met
    515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
            565                 570                 575
```

```
Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
        690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 11
<211> LENGTH: 843
<212> TYPE: PRT
<213> ORGANISM: Artificial Sequence
<220> FEATURE:
<223> OTHER INFORMATION: Synthetic Construct

<400> SEQUENCE: 11

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95
```

-continued

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
        130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
        210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Glu
        275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
        370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
        435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met

```
            515                 520                 525
Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
    610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
    770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 12
<211> LENGTH: 843
<212> TYPE: PRT
<213> ORGANISM: Artificial Sequence
<220> FEATURE:
<223> OTHER INFORMATION: Synthetic Construct

<400> SEQUENCE: 12

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
```

```
            35                  40                  45
Gln Val Gly Ala Lys Leu Val Gln Glu Ile Arg Glu Gly Lys Arg Gly
 50                  55                  60
Pro Leu Tyr Ala Gly Tyr Phe Arg Thr Trp His Asp Arg Ala Ser Thr
 65                  70                  75                  80
Gly Ile Asp Gly Lys Gln His Pro Glu Asn Thr Met Ala Glu Val
                     85                  90                  95
Pro Lys Glu Val Asp Ile Leu Phe Val Phe His Asp His Thr Ala Ser
                    100                 105                 110
Asp Ser Pro Phe Trp Ser Glu Leu Lys Asp Ser Tyr Val His Lys Leu
                    115                 120                 125
His Gln Gln Gly Thr Ala Leu Val Gln Thr Ile Gly Val Asn Glu Leu
                    130                 135                 140
Asn Gly Arg Thr Gly Leu Ser Lys Asp Tyr Pro Asp Thr Pro Glu Gly
145                 150                 155                 160
Asn Lys Ala Leu Ala Ala Ile Val Lys Ala Phe Val Thr Asp Arg
                    165                 170                 175
Gly Val Asp Gly Leu Asp Ile Leu Ile Glu His Glu Phe Thr Asn Lys
                    180                 185                 190
Arg Thr Pro Glu Glu Asp Ala Arg Ala Leu Asn Val Phe Lys Glu Ile
                    195                 200                 205
Ala Gln Leu Ile Gly Lys Asn Gly Ser Asp Lys Ser Lys Leu Leu Ile
210                 215                 220
Met Asp Thr Thr Leu Ser Val Glu Asn Asn Pro Ile Phe Lys Gly Ile
225                 230                 235                 240
Ala Glu Asp Leu Asp Tyr Leu Leu Arg Gln Tyr Tyr Gly Ser Gln Gly
                    245                 250                 255
Gly Glu Ala Glu Val Asp Thr Ile Asn Ser Asp Trp Asn Gln Tyr Gln
                    260                 265                 270
Asn Tyr Ile Asp Ala Ser Gln Phe Met Ile Gly Phe Ser Phe Phe Glu
                    275                 280                 285
Glu Ser Ala Ser Lys Gly Asn Leu Trp Phe Asp Val Asn Glu Tyr Asp
290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                    325                 330                 335
Phe Ser Tyr Ala Ile Asp Arg Asp Gly Val Ala His Val Pro Ser Thr
                    340                 345                 350
Tyr Lys Asn Arg Thr Ser Thr Asn Leu Gln Arg His Glu Val Asp Asn
                    355                 360                 365
Ile Ser His Thr Asp Tyr Thr Val Ser Arg Lys Leu Lys Thr Leu Met
                    370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Val Gly Gln Tyr Lys Gly
                    405                 410                 415
Asp Leu Glu Arg Tyr Asn Lys Thr Leu Val Leu Thr Gly Asp Lys Ile
                    420                 425                 430
Gln Asn Leu Lys Gly Leu Glu Lys Leu Ser Leu Gln Lys Leu Glu
                    435                 440                 445
Leu Arg Gln Leu Ser Asn Val Lys Glu Ile Thr Pro Glu Leu Leu Pro
450                 455                 460
```

```
Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
            515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
            835                 840
```

<210> SEQ ID NO 13
<211> LENGTH: 843
<212> TYPE: PRT
<213> ORGANISM: Artificial Sequence
<220> FEATURE:

<223> OTHER INFORMATION: Synthetic Construct

<400> SEQUENCE: 13

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Lys Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400
```

```
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
        420                 425                 430
Gln Asn Leu Lys Gly Leu Glu Lys Leu Ser Lys Leu Gln Lys Leu Glu
            435                 440                 445
Leu Arg Gln Leu Ser Asn Val Lys Glu Ile Thr Pro Glu Leu Leu Pro
    450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
        515                 520                 525
Thr Leu Met Glu Gln Val Ser Asn His Gln Lys Ile Thr Val Lys Asn
    530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
                645                 650                 655
Val Ser Asp Gly Glu Lys Val Val His His Met Lys Leu Asn Ile Gly
            660                 665                 670
Ser Gly Ala Ile Met Met Glu Asn Leu Ala Lys Gly Ala Lys Val Ile
        675                 680                 685
Gly Thr Ser Gly Asp Phe Glu Gln Ala Lys Lys Ile Phe Asp Gly Glu
    690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
                725                 730                 735
Glu Thr Asn Thr Glu Ile Lys Thr Asp Ser Ser Leu Asn Val Ala Lys
            740                 745                 750
Gly Arg Leu Gln Ile Leu Lys Asp Thr Thr Ile Asp Leu Glu Lys Met
        755                 760                 765
Asp Ile Lys Asn Arg Lys Glu Tyr Leu Ser Asn Asp Glu Asn Trp Thr
    770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
```

Leu Ser Asn Asp Val Ala Asn Thr Leu Lys Asp
            835                 840

<210> SEQ ID NO 14
<211> LENGTH: 843
<212> TYPE: PRT
<213> ORGANISM: Artificial Sequence
<220> FEATURE:
<223> OTHER INFORMATION: Synthetic Construct

<400> SEQUENCE: 14

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Phe Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr

```
                340             345             350
Tyr Lys Asn Arg Thr Ser Thr Asn Leu Gln Arg His Glu Val Asp Asn
            355                 360             365
Ile Ser His Thr Asp Tyr Thr Val Ser Arg Lys Leu Lys Thr Leu Met
        370                 375             380
Thr Glu Asp Lys Arg Tyr Asp Val Ile Asp Gln Lys Asp Ile Pro Asp
385                 390             395                 400
Pro Ala Leu Arg Glu Gln Ile Ile Gln Val Gly Gln Tyr Lys Gly
                405             410             415
Asp Leu Glu Arg Tyr Asn Lys Thr Leu Val Leu Thr Gly Asp Lys Ile
            420             425             430
Gln Asn Leu Lys Gly Leu Glu Lys Leu Ser Lys Leu Gln Lys Leu Glu
        435             440             445
Leu Arg Gln Leu Ser Asn Val Lys Glu Ile Thr Pro Glu Leu Leu Pro
    450             455             460
Glu Ser Met Lys Lys Asp Ala Glu Leu Val Met Val Gly Met Thr Gly
465             470             475             480
Leu Glu Lys Leu Asn Leu Ser Gly Leu Asn Arg Gln Thr Leu Asp Gly
            485             490             495
Ile Asp Val Asn Ser Ile Thr His Leu Thr Ser Phe Asp Ile Ser His
            500             505             510
Asn Ser Leu Asp Leu Ser Glu Lys Ser Glu Asp Arg Lys Leu Leu Met
            515             520             525
Thr Leu Met Glu Gln Val Ser Asn His Gln Lys Ile Thr Val Lys Asn
        530             535             540
Thr Ala Phe Glu Asn Gln Lys Pro Lys Gly Tyr Tyr Pro Gln Thr Tyr
545             550             555             560
Asp Thr Lys Glu Gly His Tyr Asp Val Asp Asn Ala Glu His Asp Ile
            565             570             575
Leu Thr Asp Phe Val Phe Gly Thr Val Thr Lys Arg Asn Thr Phe Ile
            580             585             590
Gly Asp Glu Glu Ala Phe Ala Ile Tyr Lys Glu Gly Ala Val Asp Gly
            595             600             605
Arg Gln Tyr Val Ser Lys Asp Tyr Thr Tyr Glu Ala Phe Arg Lys Asp
        610             615             620
Tyr Lys Gly Tyr Lys Val His Leu Thr Ala Ser Asn Leu Gly Glu Thr
625             630             635             640
Val Thr Ser Lys Val Thr Ala Thr Thr Asp Glu Thr Tyr Leu Val Asp
            645             650             655
Val Ser Asp Gly Glu Lys Val Val His His Met Lys Leu Asn Ile Gly
            660             665             670
Ser Gly Ala Ile Met Met Glu Asn Leu Ala Lys Gly Ala Lys Val Ile
        675             680             685
Gly Thr Ser Gly Asp Phe Glu Gln Ala Lys Lys Ile Phe Asp Gly Glu
        690             695             700
Lys Ser Asp Arg Phe Phe Thr Trp Gly Gln Thr Asn Trp Ile Ala Phe
705             710             715             720
Asp Leu Gly Glu Ile Asn Leu Ala Lys Glu Trp Arg Leu Phe Asn Ala
            725             730             735
Glu Thr Asn Thr Glu Ile Lys Thr Asp Ser Ser Leu Asn Val Ala Lys
        740             745             750
Gly Arg Leu Gln Ile Leu Lys Asp Thr Thr Ile Asp Leu Glu Lys Met
    755             760             765
```

```
Asp Ile Lys Asn Arg Lys Glu Tyr Leu Ser Asn Asp Glu Asn Trp Thr
            770                 775                 780
Asp Val Ala Gln Met Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
            820                 825                 830
Leu Ser Asn Asp Val Ala Asn Thr Leu Lys Asp
            835                 840

<210> SEQ ID NO 15
<211> LENGTH: 843
<212> TYPE: PRT
<213> ORGANISM: Artificial Sequence
<220> FEATURE:
<223> OTHER INFORMATION: Synthetic Construct

<400> SEQUENCE: 15

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Thr Gly Lys Thr Asp Gln
            35                  40                  45
Gln Val Gly Ala Lys Leu Val Gln Glu Ile Arg Glu Gly Lys Arg Gly
        50                  55                  60
Pro Leu Tyr Ala Gly Tyr Phe Arg Thr Trp His Asp Arg Ala Ser Thr
65                  70                  75                  80
Gly Ile Asp Gly Lys Gln Gln His Pro Glu Asn Thr Met Ala Glu Val
                85                  90                  95
Pro Lys Glu Val Asp Ile Leu Phe Val Phe His Asp His Thr Ala Ser
            100                 105                 110
Asp Ser Pro Phe Trp Ser Glu Leu Lys Asp Ser Tyr Val His Lys Leu
        115                 120                 125
His Gln Gln Gly Thr Ala Leu Val Gln Thr Ile Gly Val Asn Glu Leu
    130                 135                 140
Asn Gly Arg Thr Gly Leu Ser Lys Asp Tyr Pro Asp Thr Pro Glu Gly
145                 150                 155                 160
Asn Lys Ala Leu Ala Ala Ala Ile Val Lys Ala Phe Val Thr Asp Arg
                165                 170                 175
Gly Val Asp Gly Leu Asp Ile Pro Ile Glu His Glu Phe Thr Asn Lys
            180                 185                 190
Arg Thr Pro Glu Glu Asp Ala Arg Ala Leu Asn Val Phe Lys Glu Ile
        195                 200                 205
Ala Gln Leu Ile Gly Lys Asn Gly Ser Asp Lys Ser Lys Leu Leu Ile
    210                 215                 220
Met Asp Thr Thr Leu Ser Val Glu Asn Asn Pro Ile Phe Lys Gly Ile
225                 230                 235                 240
Ala Glu Asp Leu Asp Tyr Leu Arg Gln Tyr Tyr Gly Ser Gln Gly
                245                 250                 255
Gly Glu Ala Glu Val Asp Thr Ile Asn Ser Asp Trp Asn Gln Tyr Gln
            260                 265                 270
Asn Tyr Ile Asp Ala Ser Gln Phe Met Ile Gly Phe Ser Phe Phe Glu
        275                 280                 285
```

-continued

```
Glu Ser Ala Ser Lys Gly Asn Leu Trp Phe Asp Val Asn Glu Tyr Asp
290                 295                 300
Pro Asn Asn Pro Glu Lys Gly Lys Asp Ile Glu Gly Thr Arg Ala Lys
305                 310                 315                 320
Lys Tyr Ala Glu Trp Gln Pro Ser Thr Gly Gly Leu Lys Ala Gly Ile
                325                 330                 335
Phe Ser Tyr Ala Ile Asp Arg Asp Gly Val Ala His Val Pro Ser Thr
                340                 345                 350
Tyr Lys Asn Arg Thr Ser Thr Asn Leu Gln Arg His Glu Val Asp Asn
                355                 360                 365
Ile Ser His Thr Asp Tyr Thr Val Ser Arg Lys Leu Lys Thr Leu Met
370                 375                 380
Thr Glu Asp Lys Arg Tyr Asp Val Ile Asp Gln Lys Asp Ile Pro Asp
385                 390                 395                 400
Pro Ala Leu Arg Glu Gln Ile Ile Gln Gln Val Gly Gln Tyr Lys Gly
                405                 410                 415
Asp Leu Glu Arg Tyr Asn Lys Thr Leu Val Leu Thr Gly Asp Lys Ile
                420                 425                 430
Gln Asn Leu Lys Gly Leu Glu Lys Leu Ser Lys Leu Gln Lys Leu Glu
                435                 440                 445
Leu Arg Gln Leu Ser Asn Val Lys Glu Ile Thr Pro Glu Leu Leu Pro
450                 455                 460
Glu Ser Met Lys Lys Asp Ala Glu Leu Val Met Val Gly Met Thr Gly
465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
                500                 505                 510
Asn Ser Leu Asp Leu Ser Glu Lys Ser Glu Asp Arg Lys Leu Leu Met
                515                 520                 525
Thr Leu Met Glu Gln Val Ser Asn His Gln Lys Ile Thr Val Lys Asn
530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
                580                 585                 590
Gly Asp Glu Glu Ala Phe Ala Ile Tyr Lys Gly Ala Val Asp Gly
                595                 600                 605
Arg Gln Tyr Val Ser Lys Asp Tyr Thr Tyr Glu Ala Phe Arg Lys Asp
610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Asp Glu Thr Tyr Leu Val Asp
                645                 650                 655
Val Ser Asp Gly Glu Lys Val Val His His Met Lys Leu Asn Ile Gly
                660                 665                 670
Ser Gly Ala Ile Met Met Glu Asn Leu Ala Lys Gly Ala Lys Val Ile
                675                 680                 685
Gly Thr Ser Gly Asp Phe Glu Gln Ala Lys Lys Ile Phe Asp Gly Glu
690                 695                 700
```

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
            725                 730                 735

Glu Thr Asn Thr Glu Ile Lys Thr Asp Ser Ser Leu Asn Val Ala Lys
        740                 745                 750

Gly Arg Leu Gln Ile Leu Lys Asp Thr Thr Ile Asp Leu Glu Lys Met
    755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
            805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
            835                 840

<210> SEQ ID NO 16
<211> LENGTH: 843
<212> TYPE: PRT
<213> ORGANISM: Artificial Sequence
<220> FEATURE:
<223> OTHER INFORMATION: Synthetic Construct

<400> SEQUENCE: 16

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Ser Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

```
Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
        260                 265                 270

Asn Tyr Ile Asp Ala Ser Gln Phe Met Ile Gly Phe Ser Phe Phe Glu
    275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
            325                 330                 335

Phe Ser Tyr Ala Ile Asp Arg Asp Gly Val Ala His Val Pro Ser Thr
        340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415

Asp Leu Glu Arg Tyr Asn Lys Thr Leu Val Leu Thr Gly Asp Lys Ile
        420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
            485                 490                 495

Ile Asp Val Asn Ser Ile Thr His Leu Thr Ser Phe Asp Ile Ser His
        500                 505                 510

Asn Ser Leu Asp Leu Ser Glu Lys Ser Glu Asp Arg Lys Leu Leu Met
    515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
            565                 570                 575

Leu Thr Asp Phe Val Phe Gly Thr Val Thr Lys Arg Asn Thr Phe Ile
        580                 585                 590

Gly Asp Glu Glu Ala Phe Ala Ile Tyr Lys Glu Gly Ala Val Asp Gly
    595                 600                 605

Arg Gln Tyr Val Ser Lys Asp Tyr Thr Tyr Glu Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
```

645                 650                 655
Val Ser Asp Gly Glu Lys Val Val His His Met Lys Leu Asn Ile Gly
                660                 665                 670
Ser Gly Ala Ile Met Met Glu Asn Leu Ala Lys Gly Ala Lys Val Ile
                675                 680                 685
Gly Thr Ser Gly Asp Phe Glu Gln Ala Lys Lys Ile Phe Asp Gly Glu
                690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
                725                 730                 735
Glu Thr Asn Thr Glu Ile Lys Thr Asp Ser Ser Leu Asn Val Ala Lys
                740                 745                 750
Gly Arg Leu Gln Ile Leu Lys Asp Thr Thr Ile Asp Leu Glu Lys Met
                755                 760                 765
Asp Ile Lys Asn Arg Lys Glu Tyr Leu Ser Asn Asp Glu Asn Trp Thr
                770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
                820                 825                 830
Leu Ser Asn Asp Val Ala Asn Thr Leu Lys Asp
            835                 840

<210> SEQ ID NO 17
<211> LENGTH: 843
<212> TYPE: PRT
<213> ORGANISM: Artificial Sequence
<220> FEATURE:
<223> OTHER INFORMATION: Synthetic Construct

<400> SEQUENCE: 17

Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Thr Gly Lys Thr Asp Gln
                35                  40                  45
Gln Val Gly Ala Lys Leu Val Gln Glu Ile Arg Glu Gly Lys Arg Gly
            50                  55                  60
Pro Leu Tyr Ala Gly Tyr Phe Arg Thr Trp His Asp Arg Ala Ser Thr
65                  70                  75                  80
Gly Ile Asp Gly Lys Gln Gln His Pro Glu Asn Thr Met Ala Glu Val
                85                  90                  95
Pro Lys Glu Val Asp Ile Leu Phe Val Phe His Asp His Thr Ala Ser
                100                 105                 110
Asp Ser Pro Phe Trp Ser Glu Leu Lys Asp Ser Tyr Val His Lys Leu
                115                 120                 125
His Gln Gln Gly Thr Ala Leu Val Gln Thr Ile Gly Val Asn Glu Leu
            130                 135                 140
Asn Gly Arg Thr Gly Leu Ser Lys Asp Tyr Pro Asp Thr Pro Glu Gly
145                 150                 155                 160
Asn Lys Ala Leu Ala Ala Ala Ile Val Lys Ala Phe Val Thr Asp Arg

```
                    165                 170                 175
Gly Val Asp Gly Leu Asp Ile Thr Ile Glu His Glu Phe Thr Asn Lys
                180                 185                 190

Arg Thr Pro Glu Glu Asp Ala Arg Ala Leu Asn Val Phe Lys Glu Ile
                195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Glu
                275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
                355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
    515                 520                 525

Thr Leu Met Glu Gln Val Ser Asn His Gln Lys Ile Thr Val Lys Asn
    530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590
```

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Glu Ala Phe Arg Lys Asp
        610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
    690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
    770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
        835                 840

<210> SEQ ID NO 18
<211> LENGTH: 843
<212> TYPE: PRT
<213> ORGANISM: Artificial Sequence
<220> FEATURE:
<223> OTHER INFORMATION: Synthetic Construct

<400> SEQUENCE: 18

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
            100                 105                 110

```
Asp Ser Pro Phe Trp Ser Glu Leu Lys Asp Ser Tyr Val His Lys Leu
        115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Trp Ile Glu His Glu Phe Thr Asn Lys
                180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
                260                 265                 270

Asn Tyr Ile Asp Ala Ser Gln Phe Met Ile Gly Phe Ser Phe Phe Glu
    275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
                340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
                405                 410                 415

Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
    450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
                500                 505                 510

Asn Ser Leu Asp Leu Ser Glu Lys Ser Glu Asp Arg Lys Leu Leu Met
    515                 520                 525
```

```
Thr Leu Met Glu Gln Val Ser Asn His Gln Lys Ile Thr Val Lys Asn
        530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
                580                 585                 590

Gly Asp Glu Glu Ala Phe Ala Ile Tyr Lys Glu Gly Ala Val Asp Gly
            595                 600                 605

Arg Gln Tyr Val Ser Lys Asp Tyr Thr Tyr Gln Ala Phe Arg Lys Asp
610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
                660                 665                 670

Ser Gly Ala Ile Met Met Glu Asn Leu Ala Lys Gly Ala Lys Val Ile
            675                 680                 685

Gly Thr Ser Gly Asp Phe Glu Gln Ala Lys Lys Ile Phe Asp Gly Glu
690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
                740                 745                 750

Gly Arg Leu Gln Ile Leu Lys Asp Thr Thr Ile Asp Leu Glu Lys Met
            755                 760                 765

Asp Ile Lys Asn Arg Lys Glu Tyr Leu Ser Asn Asp Glu Asn Trp Thr
770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830

Leu Ser Asn Asp Val Ala Asn Thr Leu Lys Asp
            835                 840

<210> SEQ ID NO 19
<211> LENGTH: 843
<212> TYPE: PRT
<213> ORGANISM: Artificial Sequence
<220> FEATURE:
<223> OTHER INFORMATION: Synthetic Construct

<400> SEQUENCE: 19

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Thr Gly Lys Thr Asp Gln
            35                  40                  45
```

```
Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp His Thr Ala Ser
                100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Tyr Ile Glu His Glu Phe Thr Asn Lys
                180                 185                 190

Arg Thr Pro Glu Glu Asp Ala Arg Ala Leu Asn Val Phe Lys Glu Ile
            195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Asn Pro Ile Phe Lys Gly Ile
225                 230                 235                 240

Ala Glu Asp Leu Asp Tyr Leu Leu Arg Gln Tyr Tyr Gly Ser Gln Gly
                245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
    275                 280                 285

Glu Ser Ala Ser Lys Gly Asn Leu Trp Phe Asp Val Asn Glu Tyr Asp
290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Gly Leu Lys Ala Gly Ile
                325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
    355                 360                 365

Ile Ser His Thr Asp Tyr Thr Val Ser Arg Lys Leu Lys Thr Leu Met
370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Val Gly Gln Tyr Lys Gly
                405                 410                 415

Asp Leu Glu Arg Tyr Asn Lys Thr Leu Val Leu Thr Gly Asp Lys Ile
            420                 425                 430

Gln Asn Leu Lys Gly Leu Glu Lys Leu Ser Lys Leu Gln Lys Leu Glu
    435                 440                 445

Leu Arg Gln Leu Ser Asn Val Lys Glu Ile Thr Pro Glu Leu Leu Pro
450                 455                 460

Glu Ser Met Lys Lys Asp Ala Glu Leu Val Met Val Gly Met Thr Gly
```

```
            465                 470                 475                 480
Leu Glu Lys Leu Asn Leu Ser Gly Leu Asn Arg Gln Thr Leu Asp Gly
                485                 490                 495
Ile Asp Val Asn Ser Ile Thr His Leu Thr Ser Phe Asp Ile Ser His
            500                 505                 510
Asn Ser Leu Asp Leu Ser Glu Lys Ser Glu Asp Arg Lys Leu Leu Met
            515                 520                 525
Thr Leu Met Glu Gln Val Ser Asn His Gln Lys Ile Thr Val Lys Asn
        530                 535                 540
Thr Ala Phe Glu Asn Gln Lys Pro Lys Gly Tyr Tyr Pro Gln Thr Tyr
545                 550                 555                 560
Asp Thr Lys Glu Gly His Tyr Asp Val Asp Asn Ala Glu His Asp Ile
                565                 570                 575
Leu Thr Asp Phe Val Phe Gly Thr Val Thr Lys Arg Asn Thr Phe Ile
            580                 585                 590
Gly Asp Glu Glu Ala Phe Ala Ile Tyr Lys Glu Gly Ala Val Asp Gly
        595                 600                 605
Arg Gln Tyr Val Ser Lys Asp Tyr Thr Tyr Glu Ala Phe Arg Lys Asp
    610                 615                 620
Tyr Lys Gly Tyr Lys Val His Leu Thr Ala Ser Asn Leu Gly Glu Thr
625                 630                 635                 640
Val Thr Ser Lys Val Thr Ala Thr Thr Asp Glu Thr Tyr Leu Val Asp
                645                 650                 655
Val Ser Asp Gly Glu Lys Val Val His His Met Lys Leu Asn Ile Gly
            660                 665                 670
Ser Gly Ala Ile Met Met Glu Asn Leu Ala Lys Gly Ala Lys Val Ile
        675                 680                 685
Gly Thr Ser Gly Asp Phe Glu Gln Ala Lys Lys Ile Phe Asp Gly Glu
    690                 695                 700
Lys Ser Asp Arg Phe Phe Thr Trp Gly Gln Thr Asn Trp Ile Ala Phe
705                 710                 715                 720
Asp Leu Gly Glu Ile Asn Leu Ala Lys Glu Trp Arg Leu Phe Asn Ala
                725                 730                 735
Glu Thr Asn Thr Glu Ile Lys Thr Asp Ser Ser Leu Asn Val Ala Lys
            740                 745                 750
Gly Arg Leu Gln Ile Leu Lys Asp Thr Thr Ile Asp Leu Glu Lys Met
        755                 760                 765
Asp Ile Lys Asn Arg Lys Glu Tyr Leu Ser Asn Asp Glu Asn Trp Thr
    770                 775                 780
Asp Val Ala Gln Met Asp Asp Ala Lys Ala Ile Phe Asn Ser Lys Leu
785                 790                 795                 800
Ser Asn Val Leu Ser Arg Tyr Trp Arg Phe Cys Val Asp Gly Gly Ala
                805                 810                 815
Ser Ser Tyr Tyr Pro Gln Tyr Thr Glu Leu Gln Ile Leu Gly Gln Arg
            820                 825                 830
Leu Ser Asn Asp Val Ala Asn Thr Leu Lys Asp
        835                 840

<210> SEQ ID NO 20
<211> LENGTH: 843
<212> TYPE: PRT
<213> ORGANISM: Artificial Sequence
<220> FEATURE:
<223> OTHER INFORMATION: Synthetic Construct
```

<400> SEQUENCE: 20

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Thr Gly Lys Thr Asp Gln
        35                  40                  45

Gln Val Gly Ala Lys Leu Val Gln Glu Ile Arg Glu Gly Lys Arg Gly
    50                  55                  60

Pro Leu Tyr Ala Gly Tyr Phe Arg Thr Trp His Asp Arg Ala Ser Thr
65                  70                  75                  80

Gly Ile Asp Gly Lys Gln Gln His Pro Glu Asn Thr Met Ala Glu Val
                85                  90                  95

Pro Lys Glu Val Asp Ile Leu Phe Val Phe His Asp Thr Ala Ser
            100                 105                 110

Asp Ser Pro Phe Trp Ser Glu Leu Lys Asp Ser Tyr Val His Lys Leu
            115                 120                 125

His Gln Gln Gly Thr Ala Leu Val Gln Thr Ile Gly Val Asn Glu Leu
    130                 135                 140

Asn Gly Arg Thr Gly Leu Ser Lys Asp Tyr Pro Asp Thr Pro Glu Gly
145                 150                 155                 160

Asn Lys Ala Leu Ala Ala Ile Val Lys Ala Phe Val Thr Asp Arg
                165                 170                 175

Gly Val Asp Gly Leu Asp Ile Val Ile Glu His Glu Phe Thr Asn Lys
            180                 185                 190

Arg Thr Pro Glu Glu Asp Ala Arg Ala Leu Asn Val Phe Lys Glu Ile
        195                 200                 205

Ala Gln Leu Ile Gly Lys Asn Gly Ser Asp Lys Ser Lys Leu Leu Ile
    210                 215                 220

Met Asp Thr Thr Leu Ser Val Glu Asn Pro Ile Phe Lys Gly Ile
225                 230                 235                 240

Ala Glu Asp Leu Asp Tyr Leu Leu Arg Gln Tyr Tyr Gly Ser Gln Gly
            245                 250                 255

Gly Glu Ala Glu Val Asp Thr Ile Asn Ser Asp Trp Asn Gln Tyr Gln
            260                 265                 270

Asn Tyr Ile Asp Ala Ser Gln Phe Met Ile Gly Phe Ser Phe Phe Glu
        275                 280                 285

Glu Ser Ala Ser Lys Gly Asn Leu Trp Phe Asp Val Asn Glu Tyr Asp
    290                 295                 300

Pro Asn Asn Pro Glu Lys Gly Lys Asp Ile Glu Gly Thr Arg Ala Lys
305                 310                 315                 320

Lys Tyr Ala Glu Trp Gln Pro Ser Thr Gly Leu Lys Ala Gly Ile
            325                 330                 335

Phe Ser Tyr Ala Ile Asp Arg Asp Gly Val Ala His Val Pro Ser Thr
            340                 345                 350

Tyr Lys Asn Arg Thr Ser Thr Asn Leu Gln Arg His Glu Val Asp Asn
        355                 360                 365

Ile Ser His Thr Asp Tyr Thr Val Ser Arg Lys Leu Lys Thr Leu Met
    370                 375                 380

Thr Glu Asp Lys Arg Tyr Asp Val Ile Asp Gln Lys Asp Ile Pro Asp
385                 390                 395                 400

Pro Ala Leu Arg Glu Gln Ile Ile Gln Gln Val Gly Gln Tyr Lys Gly
            405                 410                 415
```

```
Asp Leu Glu Arg Tyr Asn Lys Thr Leu Val Leu Thr Gly Asp Lys Ile
                420                 425                 430

Gln Asn Leu Lys Gly Leu Glu Lys Leu Ser Lys Leu Gln Lys Leu Glu
            435                 440                 445

Leu Arg Gln Leu Ser Asn Val Lys Glu Ile Thr Pro Glu Leu Leu Pro
        450                 455                 460

Glu Ser Met Lys Lys Asp Ala Glu Leu Val Met Val Gly Met Thr Gly
465                 470                 475                 480

Leu Glu Lys Leu Asn Leu Ser Gly Leu Asn Arg Gln Thr Leu Asp Gly
                485                 490                 495

Ile Asp Val Asn Ser Ile Thr His Leu Thr Ser Phe Asp Ile Ser His
            500                 505                 510

Asn Ser Leu Asp Leu Ser Glu Lys Ser Glu Asp Arg Lys Leu Leu Met
        515                 520                 525

Thr Leu Met Glu Gln Val Ser Asn His Gln Lys Ile Thr Val Lys Asn
530                 535                 540

Thr Ala Phe Glu Asn Gln Lys Pro Lys Gly Tyr Tyr Pro Gln Thr Tyr
545                 550                 555                 560

Asp Thr Lys Glu Gly His Tyr Asp Val Asp Asn Ala Glu His Asp Ile
                565                 570                 575

Leu Thr Asp Phe Val Phe Gly Thr Val Thr Lys Arg Asn Thr Phe Ile
            580                 585                 590

Gly Asp Glu Glu Ala Phe Ala Ile Tyr Lys Glu Gly Ala Val Asp Gly
        595                 600                 605

Arg Gln Tyr Val Ser Lys Asp Tyr Thr Tyr Glu Ala Phe Arg Lys Asp
            610                 615                 620

Tyr Lys Gly Tyr Lys Val His Leu Thr Ala Ser Asn Leu Gly Glu Thr
625                 630                 635                 640

Val Thr Ser Lys Val Thr Ala Thr Thr Asp Glu Thr Tyr Leu Val Asp
                645                 650                 655

Val Ser Asp Gly Glu Lys Val Val His His Met Lys Leu Asn Ile Gly
            660                 665                 670

Ser Gly Ala Ile Met Met Glu Asn Leu Ala Lys Gly Ala Lys Val Ile
        675                 680                 685

Gly Thr Ser Gly Asp Phe Glu Gln Ala Lys Lys Ile Phe Asp Gly Glu
            690                 695                 700

Lys Ser Asp Arg Phe Phe Thr Trp Gly Gln Thr Asn Trp Ile Ala Phe
705                 710                 715                 720

Asp Leu Gly Glu Ile Asn Leu Ala Lys Glu Trp Arg Leu Phe Asn Ala
                725                 730                 735

Glu Thr Asn Thr Glu Ile Lys Thr Asp Ser Ser Leu Asn Val Ala Lys
            740                 745                 750

Gly Arg Leu Gln Ile Leu Lys Asp Thr Thr Ile Asp Leu Glu Lys Met
        755                 760                 765

Asp Ile Lys Asn Arg Lys Glu Tyr Leu Ser Asn Asp Glu Asn Trp Thr
            770                 775                 780

Asp Val Ala Gln Met Asp Asp Ala Lys Ala Ile Phe Asn Ser Lys Leu
785                 790                 795                 800

Ser Asn Val Leu Ser Arg Tyr Trp Arg Phe Cys Val Asp Gly Gly Ala
                805                 810                 815

Ser Ser Tyr Tyr Pro Gln Tyr Thr Glu Leu Gln Ile Leu Gly Gln Arg
            820                 825                 830
```

-continued

```
Leu Ser Asn Asp Val Ala Asn Thr Leu Lys Asp
        835                 840

<210> SEQ ID NO 21
<211> LENGTH: 995
<212> TYPE: PRT
<213> ORGANISM: Streptococcus pyogenes

<400> SEQUENCE: 21

Met Asp Lys His Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
                35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
        210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
                260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
        290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
        355                 360                 365
```

-continued

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
    515                 520                 525

Pro Gly Lys Asp Thr Leu Glu Thr Val Leu Glu Thr Tyr Lys Lys Asp
530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Ser Gly Phe Asp Arg Glu
                565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
    675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
    755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 22
<211> LENGTH: 231
<212> TYPE: PRT
<213> ORGANISM: Artificial Sequence
<220> FEATURE:
<223> OTHER INFORMATION: Synthetic Construct

<400> SEQUENCE: 22

Leu Gly Ser Gly Lys Ile Leu His Asn Gln Asn Val Asn Ser Trp Gly
1               5                   10                  15

Pro Ile Thr Val Thr Pro Thr Thr Asp Gly Glu Thr Arg Phe Asp
                20                  25                  30

Gly Gln Ile Ile Val Gln Met Glu Asn Asp Pro Val Ala Lys Ala
            35                  40                  45

Ala Ala Asn Leu Ala Gly Lys His Ala Glu Ser Ser Val Val Val Gln
50                  55                  60

Leu Asp Ser Asp Gly Asn Tyr Arg Val Tyr Gly Asp Pro Ser Lys
65                  70                  75              80

Leu Asp Gly Lys Leu Arg Trp Gln Leu Val Gly His Gly Arg Asp His
                85                  90                  95

Ser Glu Thr Asn Asn Thr Arg Leu Ser Gly Tyr Ser Ala Asp Glu Leu
            100                 105                 110

Ala Val Lys Leu Ala Lys Phe Gln Gln Ser Phe Asn Gln Ala Glu Asn
        115                 120                 125

Ile Asn Asn Lys Pro Asp His Ile Ser Ile Val Gly Cys Ser Leu Val
    130                 135                 140

```
Ser Asp Asp Lys Gln Lys Gly Phe Gly His Gln Phe Ile Asn Ala Met
145                 150                 155                 160

Asp Ala Asn Gly Leu Arg Val Asp Val Ser Val Arg Ser Ser Glu Leu
                165                 170                 175

Ala Val Asp Glu Ala Gly Arg Lys His Thr Lys Asp Ala Asn Gly Asp
            180                 185                 190

Trp Val Gln Lys Ala Glu Asn Asn Lys Val Ser Leu Ser Trp Asp Ala
        195                 200                 205

Gln Leu Glu Gly Gly Ser Gly Gly Ser Gly Asn Ser Gly His His His
    210                 215                 220

His His His His His His His
225                 230

<210> SEQ ID NO 23
<211> LENGTH: 52
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(21)
<223> OTHER INFORMATION: n is a, c, g, or t

<400> SEQUENCE: 23
cgtaaattcg tgctcaatnn naatatctag tccatcgaca ccacgatcag tt          52

<210> SEQ ID NO 24
<211> LENGTH: 52
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (32)..(34)
<223> OTHER INFORMATION: n is a, c, g, or t

<400> SEQUENCE: 24
aactgatcgt ggtgtcgatg gactagatat tnnnattgag cacgaattta cg          52
```

ENDO-S2 MUTANTS AS GLYCOSYNTHASES, METHOD OF MAKING AND USE FOR GLYCOENGINEERING OF GLYCOPROTEINS

CROSS REFERENCE TO RELATED APPLICATION

The present application is a continuation application of co-pending U.S. patent application Ser. No. 16/069,216, filed on Jul. 11, 2018 and now U.S. patent Ser. No. 11,008,601, which in turn claims priority of International Patent Application No. PCT/US2017/013734 filed on Jan. 17, 2017 and further claims priority to U.S. Provisional Patent Application No. 62/279,087 filed on Jan. 15, 2016, the contents of which is hereby incorporated by reference herein for all purposes.

GOVERNMENT RIGHTS IN INVENTION

This invention was made with government support under R01 GM096973 and R01 GM080374 awarded by the National Institutes of Health. The government has certain rights in the invention.

BACKGROUND OF THE INVENTION

Field of the Invention

The invention relates to glycoprotein synthesis, and more particularly, to the use of a recombinant mutants Endo S2, an Endo-β-N-acetylglucosminidase from the strain NZ131 of serotype M49 of *Streptococcus pyogenes*, that possesses transglycosylation activity and limited hydrolyzing activity thereby providing for efficient glycosylation remodeling of antibodies.

Description of the Related Art

Monoclonal antibodies (mAbs) represent a major class of therapeutic proteins used for the treatment of cancers, inflammatory disorders, and infectious diseases [1-3]. Compelling experimental data have shown that glycosylation can have profound impacts on the stability, biological functions, and overall therapeutic efficacy of antibodies [4-7]. For example, core-fucosylation of Fc glycans could significantly reduce the antibody-dependent cellular cytotoxicity (ADCC), and antibodies with low content of core fucosylation have shown improved therapeutic efficacy in anti-cancer therapy [8,9]. On the other hand, it has been reported that the terminal α-2,6-sialylated Fc glycoform, a minor component in the intravenous immunoglobulin (IVIG), is responsible for the anti-inflammatory activity of IVIG as demonstrated in animal models [10-13]. However, natural and recombinant antibodies are usually produced as heterogeneous glycoforms that are difficult to separate for further probing the structure-activity relationships of antibodies. Moreover, for a majority of anti-cancer mAbs on the market that rely on ADCC as a major mechanism of the therapeutic efficacy, the most active non-fucosylated glycoforms are usually present as minor fractions among the heterogeneous mixtures [8,9]. Thus, methods that can lead to the production of structural well defined, homogeneous glycoforms of antibodies are highly desirable for both functional studies and for the development of better antibody-based therapeutics. In parallel to the attempt to control glycosylation through host glycosylation pathway engineering [14-20], a chemoenzymatic glycosylation remodeling method, which involves endoglycosidase-catalyzed deglycosylation and subsequent transglycosylation of intact antibodies, has been emerging as a promising approach to obtain homogeneous antibody glycoforms [21]. It has been shown that the Fc glycans of recombinant IgG-Fc domain could be remodeled through the enzymatic deglycosylation-transglycosylation steps under the catalysis of an appropriate endoglycosidase, including Endo-A and Endo-D, without the need of denaturing the proteins [22-24]. In 2012, the first example of glycosylation remodeling of an intact therapeutic monoclonal antibody and IVIG, which was enabled by the discovery of glycosynthase mutants of Endo-S, an endoglycosidase from *Streptococcus pyogenes* [25]. In this approach, the heterogeneous Fc glycans of a monoclonal antibody such as rituximab are removed by Endo S catalyzed deglycosylation to yield the antibody protein backbone carrying only the α1,6-fucosylated GlcNAc acceptor at the glycosylation site. Then a desired N-glycan is transferred to the GlcNAc acceptor by an Endo-S glycosynthase mutant (Endo S-D233A or D233Q) in a site- and stereo-specific manner to reconstitute a homogeneous glycoform of the antibody. The Endo-S glycosynthase mutants have been used by several research groups for the synthesis of different homogeneous glycoforms of antibodies for structural and functional studies [26-31]. While the Endo-S glycosynthases were able to transfer biantennary complex type and modified Man3GlcNAc core, these mutants showed only marginal activity in transferring high-mannose type N-glycans. More recently, glycosynthase mutants from Endo-F3 have been generated, another GH18 family endoglycosidase [32]. It was found that the Endo-F3 glycosynthases, such as the D165A mutant, was able to transfer triantennary N-glycan to Fc domain of intact antibody, but they required α1,6-fucosylated GlcNAc moiety as the acceptor for transglycosylation and were unable to transfer to non-fucosylated GlcNAc acceptors. These studies have demonstrated that the glycosynthases so far available still have limitations due to substrate specificity and also vary in transglycosylation efficiency.

With an understanding of the shortcomings of other mutants, an effort to expand the scope of the glycosylation remodeling strategy, is described herein wherein attention is turned to Endo-S2, an endoglycosidase from *Streptococcus pyogenes* of serotype M49 [33,34]. Endo-S2 shows only 37% sequence identity to Endo-S from the same bacteria and demonstrates a broader glycan substrate specificity in Fc deglycosylation than Endo-S [34]. Data implicated that the wild type Endo-S2 can hydrolyze various types of N-glycans from antibody Fc domains than Endo-S. But it has been unknown whether Endo-S2 possesses transglycosylation activity and, if yes, whether Endo-S2 glycosynthases can be generated by site-directed mutagenesis.

Thus, it would be advantageous to evaluate whether efficient glycosynthases could be generated from Endo-S2 and whether they would potentially have broader substrate specificity in transglycosylation than those previously reported.

SUMMARY OF THE INVENTION

The present invention provides for recombinant Endo-S2 mutants (named Endo-S2 glycosynthases) that exhibit reduced hydrolysis activity and increased transglycosylation activity for the synthesis of glycoproteins wherein a desired sugar chain is added to a fucosylated or nonfucosylated GlcNAc-IgG acceptor. As such, the present invention allows for the synthesis and remodeling of therapeutic antibodies thereby providing for certain biological activities, such as, prolonged half-life time in vivo, less immunogenicity, enhanced in vivo activity, increased targeting ability, and/or ability to deliver a therapeutic agent. The mutant Endo-S2 glycosynthases of the present enable the glycosylation remodeling of therapeutic antibodies and Fc fragments thereof with increase number of diverse glycans such as high-mannose type and hybrid type glycans that cannot be achieved by the previously disclosed Endo-S mutants.

In one aspect, the present invention provides for transglycosylation activity of mutants of an endo-β-N-acetylglucosaminidase of strain NZ131 of serotype M49 of *Streptococcus pyogenes* (Endo-S2) (SEQ ID NO: 1), wherein the mutants have at least 85% homology thereto and exhibit transglycosylation activity on both fucosylated and nonfucosylated GlcNAc-IgG acceptors, wherein the endoglycosidases enable the transfer of an oligosaccharide (in the form of an activated sugar oxazoline) en bloc to a fucosylated or nonfucosylated GlcNAc-IgG to form a new glycoform of IgG.

In another aspect, the present invention provides for Endo-S2 mutant proteins that show remarkably enhanced transglycosylation efficiency and diminished or abrogated product hydrolytic activity relative to the wild type Endo S2. Mutants preferably include site-specific mutations including a mutation at Asp-184. The mutant proteins include, but are not limited to, D184A (SEQ ID NO: 2), D184N (SEQ ID NO: 3), D184Q (SEQ ID NO: 4), D184R (SEQ ID NO: 5), D184C (SEQ ID NO: 6), D184M (SEQ ID NO: 7), D184E (SEQ ID NO: 8), D184G (SEQ ID NO: 9), D184H (SEQ ID NO: 10), D184I (SEQ ID NO: 11), D184L (SEQ ID NO: 12), D184K (SEQ ID NO: 13), D184F (SEQ ID NO: 14), D184P (SEQ ID NO: 15), D184S(SEQ ID NO: 16), D184T (SEQ ID NO. 17); D184W (SEQ ID NO: 18), D184Y(SEQ ID NO: 19), D184V (SEQ ID NO: 20) or fragments thereof that include the catalytic domain and exhibit increased transglycosylation and reduced hydrolysis related to the wild type Endo-S2 protein. Preferably the mutant proteins include D184M (SEQ ID NO: 7), D184E (SEQ ID NO: 8) and D184Q (SEQ ID NO: 4).

Notably any Endo-S2 fragments and domains that carry a mutation at the D184 site are included in the present invention wherein any such domains and fragments may be fused to other proteins including, but not limited to, CPD, Fc, MBP, etc. The catalytic domain and the specific site of mutation are critical for the enzymatic activity, and thus, other sites on the enzyme may be modified or truncated, such as a terminus without affect much of the glycosynthase activity In a further aspect, the present invention provides for a chemoenzymatic method for the preparation of a homogeneous fucosylated or nonfucosylated glycoforms of IgG antibodies, comprising:
a. providing an acceptor selected from the group consisting of a core fucosylated GlcNAc-IgG and nonfucosylated GlcNAc-IgG or corresponding IgG-Fc fragments; and
b. reacting the acceptor with a donor substrate including an activated oligosaccharide moiety, in the presence of a *S. pyogenes* Endo-S2 Asp-184 mutant protein or fragment thereof that includes the catalytic domain and exhibits increased transglycosylation and reduced hydrolytic activity relative to the wild type Endo-S2 enzyme to transfer the activated oligosaccharide moiety to the acceptor and yield the homogeneous fucosylated or nonfucosylated glycoprotein.

In a still further aspect, the present invention provides a method for preparing a core-fucosylated IgG or IgG-Fc fragment having a predetermined oligosaccharide moiety, comprising:
a. providing a core-fucosylated acceptor protein comprising an asparagine-linked core-fucosylated N-acetylglucosamine (GlcNAc) residue; and
b. enzymatically reacting the core-fucosylated acceptor protein with an activated oligosaccharide donor in the presence of a Endoglycosidase-S2 D184 mutant protein or fragment thereof that includes the catalytic domain and exhibits increased transglycosylation and reduced hydrolytic activity relative to the wild type Endo-S2 enzyme, wherein the activated oligosaccharide donor carries an oligosaccharide moiety comprising a predetermined number and type of sugar residues, wherein the oligosaccharide moiety is covalently linked to the acceptor protein, thereby preparing the core-fucosylated IgG or IgG-Fc fragment having the predetermined oligosaccharide moiety.

In yet another aspect, the present invention provides for an activated oligosaccharide moiety, such as glycan or oligosaccharide oxazoline, glycosyl fluoride, glycosyl azide or an aryl glycoside, as a donor substrate for the synthesis of homogeneous core-fucosylated glycoproteins or nonfucosylated glycoproteins. Preferably the activated oligosaccharide moiety is an oligosaccharide oxazoline.

In a further aspect, the present invention relates to a chemoenzymatic method for the preparation of a homogeneous fucosylated or nonfucosylated glycoprotein, said method comprising:
a. providing an acceptor selected from core fucosylated or nonfucosylated GlcNAc-IgG or IgG-Fc fragments; and
b. reacting the acceptor with a donor substrate in the presence a *S. pyogenes* Endo-S Asp-184 mutant protein or fragment thereof that includes the catalytic domain and exhibits increased transglycosylation and reduced hydrolytic activity relative to the wild type Endo-S2 enzyme, wherein the donor substrate comprises a predetermined oligosaccharide component with a defined number and type of sugar residues and specific linkage types, thereby providing the homogeneous fucosylated or nonfucosylated glycoprotein.

Notably the *S. pyogenes* Endo-S Asp-184 mutant protein or fragment thereof can include additional mutations in the amino acid residues but importantly carries a D184 mutation.

In one embodiment, the fucosylated GlcNAc containing protein is an alpha-1-6-fucosyl-GlcNAc-protein.

In another aspect, the present invention relates to a method of IgG or IgG-Fc glycoprotein remodeling with an oligosaccharide having a predetermined oligosaccharide component with a defined number and type of sugar residues and with specific linkage types, the method comprising:
a. providing a fucosylated glycoprotein substrate comprising Fc N-glycans;
b. treating the fucosylated glycoprotein substrate with an endo-enzyme to hydrolyze the bond between the two core GlcNAc residues in the N-glycans to yield a core-fucosylated or nonfucosylated GlcNAc-IgG or IgG-Fc fragments; and
c. attaching the oligosaccharide to the Asn-linked GlcNAc moiety in the presence of an Endo-S2 mutant having an amino acid sequence selected from the group consisting of SEQ ID NO: 2 to SEQ ID NO: 20 or fragment thereof that includes the catalytic domain and exhibits increased transglycosylation and reduced hydrolytic activity relative to the wild type Endo-S2 enzyme (SEQ ID NO: 1), thereby adding a predetermined the oligosaccharide component.

In a further aspect, the present invention relates to a method of fucosylated or nonfucosylated IgG or IgG-Fc fragment remodeling with an oligosaccharide having a predetermined oligosaccharide component with a defined number and type of sugar residues and with specific linkage types, the method comprising:

a. providing a fucosylated or nonfucosylated GlcNAc-IgG or IgG-Fc fragments obtained from natural or recombined sources carrying heterogeneous N-glycans;

b. treating the natural or recombinant IgG or IgG-Fc fragment with an endo-enzyme (a wild type endoglycosidase or a mutant endoglycosidase with efficient hydrolytic activity) to hydrolyze the bond between the two GlcNAc residues positioned closest to the peptide domain thereby forming a deglycosylated protein carrying the core fucosylated or nonfucosylated GlcNAc-IgG or a IgG-Fc fragment; and c. attaching the pre-determined oligosaccharide to the GlcNAc residue to reconstitute the natural beta-1,4-glycosidic bond through transglycosylation with a *S. pyogenes* Endo-S2 Asp-184 mutant enzyme or fragment thereof that includes the catalytic domain and exhibits increased transglycosylation and reduced hydrolytic activity relative to the wild type Endo-S2 enzyme, thereby adding a predetermined the oligosaccharide component.

Applicable oligosaccharide oxazolines include, but not limited to, high-mannose type, hybrid type, sialoglycan oxazoline and complex type N-glycan, as well as their selectively modified derivatives such as those with specific tags. Preferably, di-, tri-, tetra-, penta-, hexyl-, hepta-, octyl-, nona-, deca-, or undeca-saccharide oxazolines are utilized as donor substrates for a highly efficient chemoenzymatic synthesis of homogeneous core fucosylated or nonfucosylated IgG antibodies and IgG-Fc fragments.

In yet another aspect, the present invention relates to a method of synthesis of a modified antibody or fragment thereof, the method comprising;

a. using a naturally existing IgG antibody or a recombinant antibody or Fc domains carrying Fc N-glycans as precursors;

b. Fc deglycosylating using an endoglycosidase such as a wild Endo-S2 to deglycosylate the Fc domain to form a GlcNAc-acceptor; wherein the GlcNAc moiety is positioned on the Fc region of the antibody and the GlcNAc moiety is either core fucosylated or nonfucosylated; and c. transglycosylating the GlcNAc moiety in the antibody with an oligosaccharide oxazoline or a sialoglycan oxazoline having a predetermined number of sugar residues under the catalysis of an enzyme selected from the group consisting of Endo-S2 mutants SEQ ID NO: 2 to SEQ ID NO: 20 or fragment thereof that includes the catalytic domain and exhibits increased transglycosylation and reduced hydrolytic activity relative to the wild type Endo-S2 enzyme to form the modified antibody with the predetermined number of saccharides.

In yet another aspect, the present invention provides a method of remodeling intravenous immunoglobulins (IVIG) exhibiting Fc-sialylated glycoforms, the method comprising:

a. providing an IVIG carrying Fc N-glycans;

b. Fc deglycosylating the Fc N-glycans using an endoglycosidase including Endo-S to form a GlcNAc-acceptors; wherein the GlcNAc-acceptors are positioned on the Fc region of the IVIG and the GlcNAc-acceptors are either fucosylated or nonfucosylated; and c. transglycosylating the GlcNAc-acceptors with sialoglycan oxazoline having a predetermined number of sugar residues under the catalysis of an enzyme selected from the group consisting of Endo-S2 mutants SEQ ID NO: 2 to SEQ ID NO: 20 or fragment thereof that includes the catalytic domain and exhibits increased transglycosylation and reduced hydrolytic activity relative to the wild type Endo-S2 enzyme to form a sialylated WIG.

Another aspect of the present invention provides for an IVIG preparation containing composition comprising at least 90% of homogeneous sialylated Fc glycoforms to increase anti-inflammatory activity, wherein the sialylated Fc glycoforms are synthesized using a *Streptococcus pyogenes* Endo-S2 Asp-184 mutant in combination with a GlcNAc moiety positioned on the Fc region of a deglycosylated IVIG and a sialoglycan oxazoline having a predetermined number of sugar residues.

In a still further aspect, the present invention relates to a method of synthesizing homogeneous core fucosylated or nonfucosylated IgG antibodies or IgG-Fc fragments, the method comprising:

a. providing a natural or recombinant IgG antibody or IgG-Fc fragment, wherein the recombinant IgG or IgG-Fc is produced from a typical protein expression system, including but not limited to yeast, insect, plant, and any mammalian expression system;

b. removing the N-glycans by an enzyme selected from the group consisting of Endo-H, Endo-A, Endo-S, Endo S2 (WT) and/or Endo-F3 to form a core fucosylated or nonfucosylated GlcNAc-containing protein;

c. providing a sugar oxazoline or sialoglycan oxazoline with a desired oligosaccharide component comprising a defined number and type of sugar residues in the chain; and d. enzymatically transglycosylating the fucosylated or nonfucosylated GlcNAc-containing protein with a sugar oxazoline having a desired number of sugar residues or sialoglycan oxazoline having a desired number of sugar and sialic acid residues, with an endoglycosidase selected from the group consisting of a *Streptococcus pyogenes* Endo-S2 Asp-184 mutant enzyme or fragment thereof that exhibits increased transglycosylation and reduced hydrolytic activity relative to the wild type Endo-S2 enzyme, thereby forming a homogeneous core fucosylated or nonfucosylated IgG antibody or IgG-Fc fragment having an extension of desired number of sugar residues and/or sialic acid.

It is envisioned that the oligosaccharide oxazoline or sialoglycan oxazoline having a predetermined oligosaccharide component with a defined number and type of sugar residues may further comprises an additional moiety or tag including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug or therapeutic agent having biological activity to treat a condition, the delivery device comprising: a remodeled IgG or IgG-Fc fragment having a predetermined sugar chain or sialoglycan and a therapeutic agent or drug attached to the terminal sugar residue or sialic acid.

The present invention envisions modifying monoclonal antibodies related to HIV including, but not limited to 17b, 48d, A32, C11, 2G12, F240, IgG1b12, 19e, X5, TNX-355 and F91, all of which are commercially available.

Further antibodies related to cancer or other diseases may also be remodeled for individual fit to certain receptors thereby increasing biological activity, the monoclonal antibodies may include, but are not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101 (Aphton), volociximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

A still further aspect of the invention relates to a method of remodeling an antibody which initially includes a heterogeneous sugar chain, the method comprising:
a. removing the heterogeneous sugar chain from the antibody with an endoglycosidase to leave a single fucosylated- or nonfucosylated-GlcNAc moiety attached to an original glycosylation site; and
b. transferring a core oligosaccharide or sialoglycan oxazoline with at least one tag to the fucosylated- or -nonfucosylated GlcNAc moiety by an endoglycosidase catalyzed transglycosylation to yield a tagged antibody, wherein the endoglycosidase is selected from the group consisting of Endo-S2 mutants SEQ ID NO: 2 to SEQ ID NO: 20 or fragment thereof that includes the catalytic domain and exhibits increased transglycosylation and reduced hydrolytic activity relative to the wild type Endo-S2 enzyme.

The tag moiety may include, but is not limited to, antigens, therapeutic drugs such as for cancer or HIV, toxins, fluorescent probes, biotin, PEG species, lipids, or nucleotides.

In yet another aspect, the present invention provides for Antibody-drug conjugates or ADCs wherein the antibody can be modified according to the present invention and are designed as a targeted therapy for the treatment of people with cancer. Specifically, an ADC contains two parts: a monoclonal antibody and a small amount of a highly potent cytotoxic drug, linked to the antibody. When the ADC's antibody binds with a particular receptor on the target cell's surface, the linkage breaks, and the ADC releases a lethal toxin into the cell. Specific monoclonal antibodies are described herein later and also possible cytotoxic drugs. Thus, the present invention provides for a modified antibody further comprising an additional moiety including, a therapeutic agent for treating cancer such as a chemokine and/or a cytokine thereby forming an Antibody-drug conjugate (ADC).

In another aspect, the present invention provides for a composition comprising at least one *Streptococcus pyogenes* Endo-S2 mutant selected from the group consisting of D184M (SEQ ID NO:7) and D184Q (SEQ ID No: 4).

In yet another aspect, the present invention provides a substantially homogeneous preparation of core fucosylated or nonfucosylated antibody or Fc fragment thereof having a predetermined oligosaccharide moiety, wherein the substantially homogeneous preparation is produced by any of the aforementioned methods. Also provided are compositions comprising such homogeneous preparations.

In another aspect, the present invention provides for a method of treatment using a remodeled antibody having a desired glycosylation state and/or sialylated form in an amount sufficient to modulate biological activity in the treated subject.

In a further aspect, the present invention provides for a kit including a least one *Streptococcus pyogenes* Endo-S2 mutant selected from the group consisting of SEQ ID NO: 2 to 20 and preferably D184M (SEQ ID NO:7), D184E (SEQ ID NO: 8) and D184Q (SEQ ID NO: 4).

Other aspects, features and embodiments of the invention will be more fully apparent from the ensuing disclosure and appended claims.

BRIEF DESCRIPTION OF THE FIGURES

FIG. 1 shows the structures of a typical IgG antibody and the Fc N-glycans. a) Alpha backbone structure of human IgG showing functional regions (PDB code 1HZH): b) The structure of a full-length bi-antennary complex type N-glycan attached to the Asn-297 in the Fc domain FIG. 2 shows the sequence alignment of Endo S2 (SEQ ID NO: 1) and Endo S (SEQ ID NO: 21). The aspartic acid residue (D233 of Endo-S and D184 of Endo-S2) critical for promoting oxazolinium ion formation in hydrolysis and the catalytic general acid/base residue (E235 of Endo-S and E186 of Endo-S2) are marked.

DETAILED DESCRIPTION OF THE INVENTION

Figure 3:
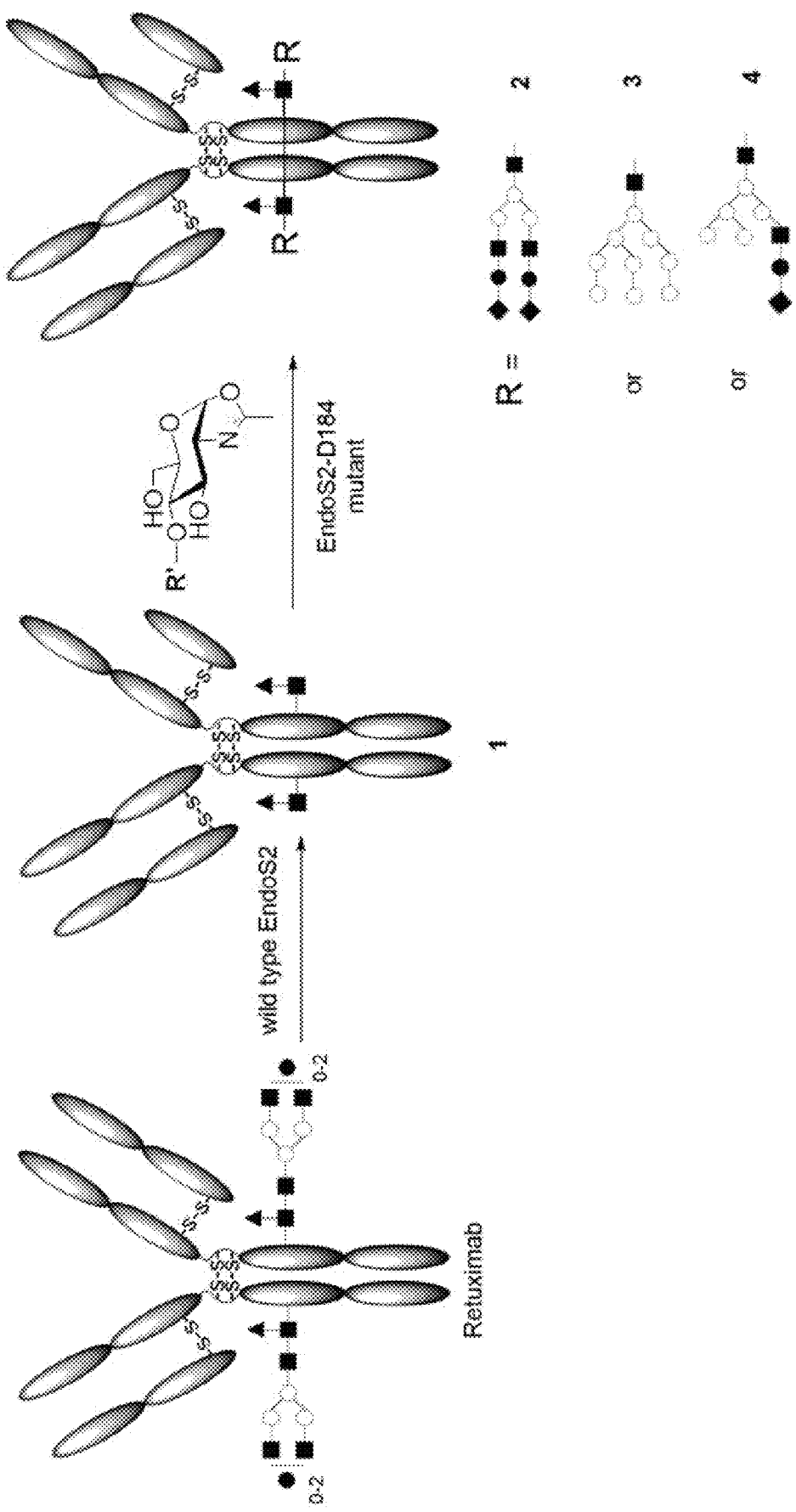
FIG. 3 shows the scheme for glycosylation remodeling of fucosylated rituximab to homogeneous complex, high mannose, and hybrid glycoforms.

The present invention provides for novel glycosynthase EndoS2 Asp 184 mutants that show remarkable transglycosylation efficiency capable of transferring complex, high mannose, and Hybrid type N-glycans from activated glycan oxazolines to deglycosylated intact antibodies without product hydrolysis. It has been found herein that the glycosynthase EndoS2 Asp 184 mutants acted efficiently on both core-fucosylated and nonfucosylated GlcNAc-Fc domain of intact antibodies to provide various defined IgG glycoforms. As described herein the Endo-S2 did possess potent transglycosylation activity, and the systematic site-directed mutagenesis led to the discovery of several glycosynthase mutants, including D184M and D184Q, that showed remarkable transglycosylation activity without apparent product hydrolysis activity. Moreover, it is shown herein that the Endo-S2 glycosynthases demonstrated remarkably relaxed substrate specificity, being capable of transferring three major types (complex, high-mannose, and hybrid type) of N-glycans for antibody glycosylation remodeling. Further, as further described herein, it was found that the Endo-S2 glycosynthase mutants were much more active in general than the Endo-S mutants for transglycosylation. A highly efficient glycosylation remodeling of two therapeutic monoclonal antibodies, rituximab and trastuzumab (Herceptin), is described. Further, antibodies and intravenous immunoglobulins were transformed into Fc fully sialylated glycoforms having increased anti-inflammatory activity. Still further, the present invention provides for a homogeneous nonfucosylated glycoform having increased ADCC activity with enhanced FcγIIIa receptor-binding activity and azido-tagged glycoforms that can be further transformed into other glycoforms.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

It is understood that aspects of the present invention described herein include "consisting" and/or "consisting essentially of" aspects.

Definitions

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or unoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core-fucosylated glycoproteins or nonfucosylated glycoproteins wherein the oligosaccharide component comprises at least 75%, more preferably at least 90%, and most preferably at least 95% of the same number and types of sugar residues.

As used herein, "protein" or "glycoprotein" is interchangeable with the terms peptide and glycopeptide.

As used herein, "homology" refers to amino acid sequence having substantial identity or similarity between two polypeptides and having at least 85%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

Antigens useful for attachment as a tag to a modified fucosylated or nonfucosylated glycoprotein of the present invention and more preferably an antibody or fragment thereof may be a foreign antigen, an endogenous antigen, fragments thereof, or variants having the same functional activity.

As used herein, "endogenous antigen" refers to a protein or part thereof that is naturally present in the recipient animal cell or tissue, such as a cellular protein, an immunoregulatory agent, or a therapeutic agent.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession #AF238278), Gag, Env (National Institute of Allergy and Infectious Disease HIV Repository Cat. #2433; GenBank accession #U39362), Tat (National Institute of Allergy and Infectious Disease HIV Repository Cat. #827; GenBank accession #M13137), Rev (National Institute of Allergy and Infectious Disease HIV Repository Cat. #2088; GenBank accession #L14572), Pol (National Institute of Allergy and Infectious Disease HIV Repository Cat. #238; GenBank accession #AJ237568) and T cell and B cell epitopes of gp120; the hepatitis B surface antigen (GenBank accession #AF043578); rotavirus antigens, such as VP4 (GenBank accession #AJ293721) and VP7 (GenBank accession #AY003871); influenza virus antigens, such as hemagglutinin (GenBank accession #AJ404627); nucleoprotein (GenBank accession #AJ289872); and herpes simplex virus antigens, such as thymidine kinase (GenBank accession #AB047378).

The bacterial pathogens, from which the bacterial antigens are derived, include but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also known as "SOD" and "p60") of *Listeria monocytogenes*; the urease of *Helicobacter pylori*, and the receptor-binding domain of lethal toxin and/or the protective antigen of *Bacillus anthrax*.

Example of antigens from biological weapons or pathogens include, but are not limited to, smallpox, anthrax, tularemia, plague, listeria, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC #: 30145); *Trypanosome* spp., such as *Trypanosoma cruzi* (ATCC #: 50797); *Giardia* spp., such as *Giardia intestinalis* (ATCC #: 30888D); *Boophilus* spp.; *Babesia* spp., such as *Babesia microti* (ATCC #: 30221); *Entamoeba* spp., such as *Entamoeba histolytica* (ATCC #: 30015); *Eimeria* spp., such as *Eimeria maxima* (ATCC #40357); *Leishmania* spp., (Taxonomy ID: 38568); *Schistosome* spp., such as *Schistosoma mansoni* (GenBank accession #AZ301495); *Brugia* spp., such as *Brugia malayi* (GenBank accession #BE352806); *Fascida* spp., such as *Fasciola hepatica* (GenBank accession #AF286903); *Dirofilaria* spp., such as *Dirofilaria immitis* (GenBank accession #AF008300); *Wuchereria* spp., such as *Wuchereria bancrofti* (GenBank accession #AF250996); and *Onchocerca* spp; such as *Onchocerca volvulus* (GenBank accession #BE588251).

Examples of parasite antigens include, but are not limited to, the pre-erythrocytic stage antigens of *Plasmodium* spp. such as the circumsporozoite antigen of *P. falciparum* (GenBank accession #M22982) *P vivax* (GenBank accession #M20670); the liver stage antigens of *Plasmodium* spp, such as the liver stage antigen 1 (as referred to as LSA-1; GenBank accession #AF086802); the merozoite stage antigens of *Plasmodium* spp; such as the merozoite surface antigen-1 (also referred to as MSA-1 or MSP-1; GenBank accession #AF199410); the surface antigens of *Entamoeba histolytica*, such as the galactose specific lectin (GenBank accession #M59850) or the serine rich *Entamoeba histolytica* protein; the surface proteins of *Leishmania* spp, such as 63 kDa glycoprotein (gp63) of *Leishmania major* (GenBank accession #Y00647 or the 46 kDa glycoprotein (gp46) of *Leishmania major*; paramyosin of *Brugia malayi* (GenBank accession #U77590; the triose-phosphate isomerase of *Schistosoma mansoni* (GenBank accession #W06781; the secreted globin-like protein of *Trichostrongylus colubriformis* (GenBank accession #M63263; the glutathione-S-transferases of *Fasciola hepatica* (GenBank accession #M77682; *Schistosoma bovis* (GenBank accession #M77682); *S. japonicum* (GenBank accession #U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession #M27160); tyrosinase-related protein (also referred to as TRP; GenBank accession #AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS β chain, which is useful in therapeutic vaccines against autoimmune encephalomyelitis (GenBank accession #D88762); glatamic acid decarboxylase, which is useful in therapeutic vaccines against insulin-dependent type 1 diabetes (GenBank accession #NM013445); thyrotropin receptor (TSHr), which is useful in therapeutic vaccines against Grave's disease (GenBank accession #NM000369) and tyrosinase-related protein 1, which is useful in therapeutic vaccines against vitiligo (GenBank accession #NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different fucosylated glycoproteins and nonfucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Fucosylated and nonfucosylated glycoproteins are important classes of biomolecules that play crucial roles in many biological events such as cell adhesion, tumor metastasis, pathogen infection, and immune response. As indicated previously herein, a major problem in structural and functional studies of fucosylated or nonfucosylated glycoproteins is their structural microheterogeneity. Natural and recombinant fucosylated or nonfucosylated glycoproteins are typically produced as a mixture of glycoforms that differ only in the structure of the pendent oligosaccharides.

The remodeled glycoproteins, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The fucosylated and nonfucosylated glycoproteins, produced according to the methods described herein, can be used for diagnosis and therapeutics. Approximately two-thirds of therapeutic proteins used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials and the Endo-S2 mutants of the present invention are able to transglycosylate fucosylated and nonfucosylated natural and recombinant glycoproteins without the negative aspects of hydrolysis.

The features and advantages of the present invention are more fully shown by the following non-limiting examples.

Examples

Generation of Endo-S2 Glycosynthase Mutants and their Use for Glycosylation Remodeling of Intact Monoclonal Antibody Rituximab Glycosynthases have been previously made from several GH85 endoglycosidases (ENGases), including EndoA, EndoM, EndoD and GH18 endoglycosidase EndoS, by site-directed mutagenesis of a key asparagine (Asn) in GH85 family or aspartic acid (Asp) residue in GH18 family responsible for promoting oxazolinium ion intermediate formation during hydrolysis. [36,38] Endo-S2 is an endoglycosidase belonging to the glycoside hydrolase family 18 (GH18) [33], which is in the same GH family as EndoS, EndoF1, EndoF2, and EndoF3 that were recently shown to have transglycosylation activity. Based on the assumption that EndoS2-catalyzed hydrolysis also proceeds by a substrate-assisted mechanism involving the formation of an oxazolinium ion intermediate, as demonstrated by other GH18 endoglycosidases such as EndoS, potential glycosynthases from Endo-S2 were created by identifying and mutating the residue responsible for promoting oxazolinium ion formation. Previous structural and mutagenesis studies on Endo-S have shown that an aspartic acid residue at position 233 (D233) is responsible for promoting oxazoline formation and that the E235 residue is the general acid/base for catalytic hydrolysis [47, 48]. Sequence alignment of EndoS2 with EndoS (FIG. 2) led to the identification of two key residues in EndoS for catalysis: the D184 residue (corresponding to D233 in EndoS) responsible for promoting oxazolinium ion formation and the E186 residue (equivalent to E235 of EndoS) as the general acid/base residue in glycan hydrolysis as shown in FIG. 2. Thus, on the assumption that the D184 is the critical residue that promotes oxazolinium ion intermediate formation in the hydrolysis via a substrate-assisted mechanism, nineteen specific mutants, D184A-Y (SEQ ID NO: 2-20) were generated by site-directed mutagenesis of Endo-S2 (SEQ ID NO:1). These mutants, as well as the wild-type EndoS2, were expressed in *Escherichia coli* in high yield (20-30 mg/L) as a CPD fusion protein and purified by Ni-NTA affinity chromatography.

Figure 4:
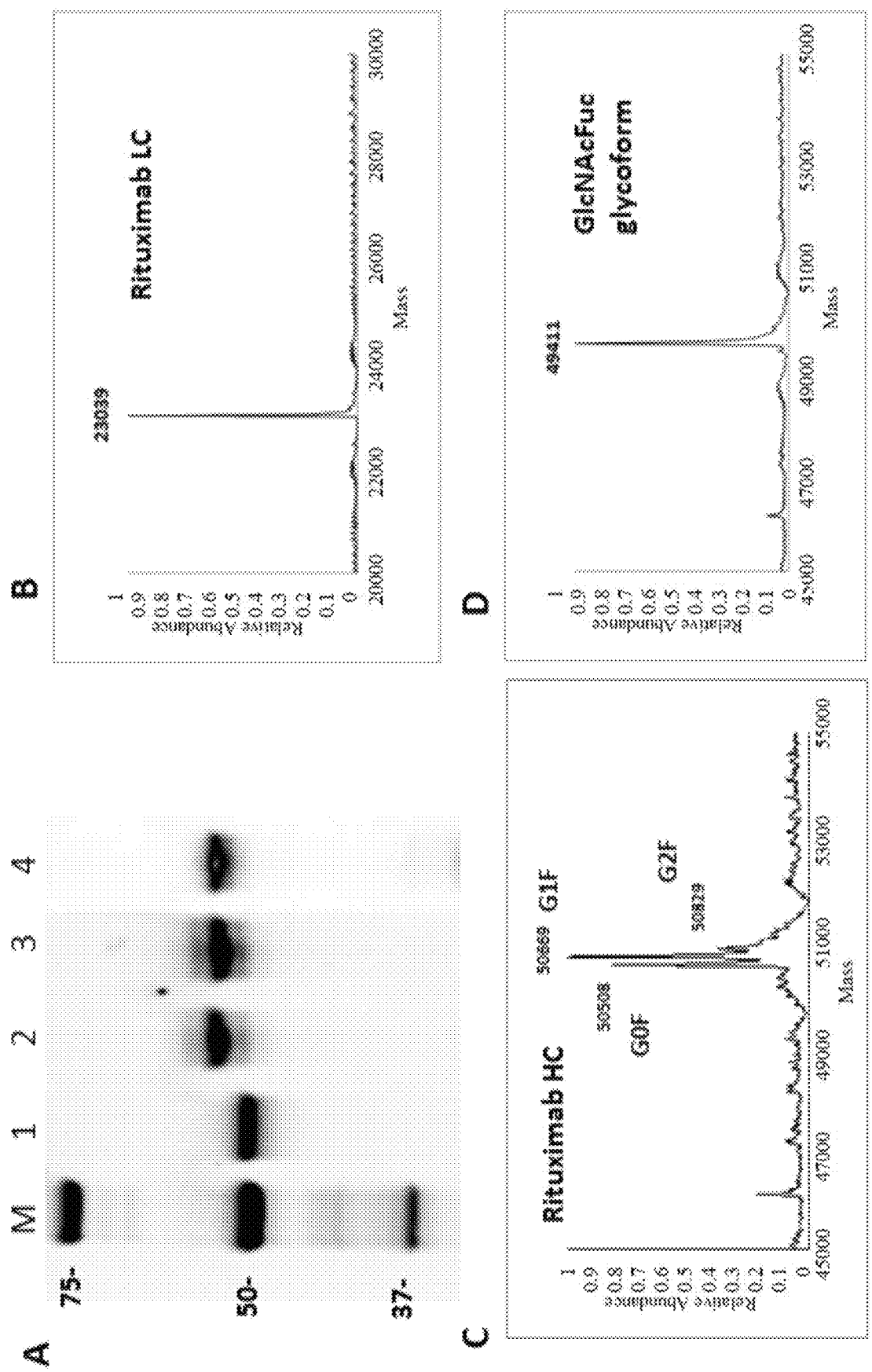
FIG. 4 shows the SDS-PAGE and ESI-MS analysis of the glycosylation remodeling of rituximab. (A) SDS-PAGE analysis: Lane 1, commercial rituximab; Lane 2, EndoS2 de-glycosylated rituximab (1); Lane 3, transglycosylation product of complex glycoform (5) from the EndoS2-D184Q catalyzed reaction between (1) and sialo complex glycan oxazoline (2); Lane 4, transglycosylation product of Man9GlcNAc (6) from the EndoS2-D184A catalyzed reaction of (1) and (3); lane 5, the transglycosylation product of sialo hybrid glycoform (7) from the EndoS2-D184A catalyzed reaction between the deglycosylated rituximab (1) and hybrid glycan oxazoline (4); (B) ESI-MS (after deconvolution) of the light chain of the commercial rituximab; (C) ESI-MS (after deconvolution) of the heavy chain of the commercial rituximab; (D) ESI-MS of the de-glycosylated rituximab (1). (E) ESI-MS of the transglycosylation complex type product (5). (F) ESI-MS of the transglycosylation Man9 product (6). (G) ESI-MS of the transglycosylation sialo hybrid type product (7).
Figure 4:
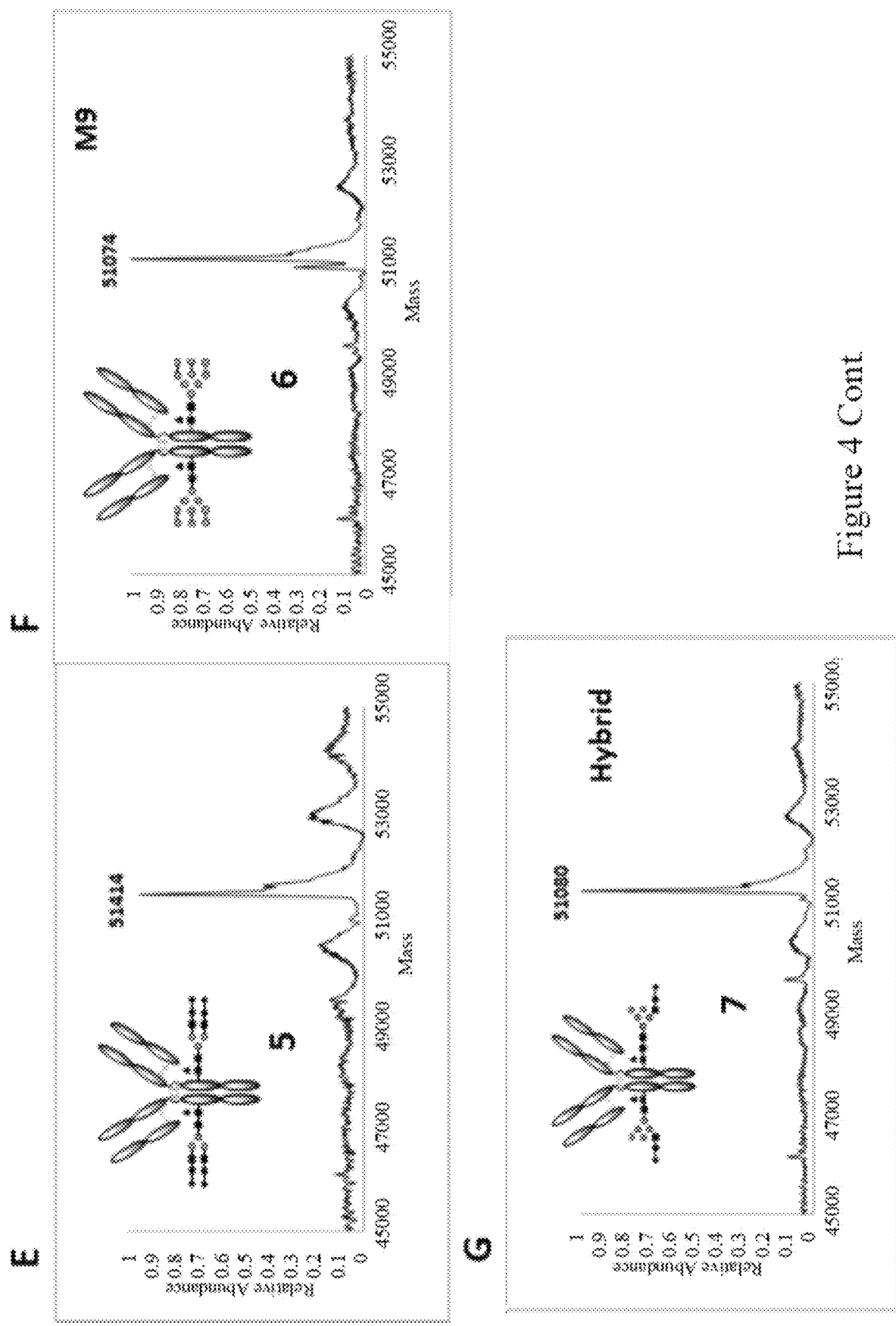

Rituximab, a therapeutic monoclonal antibody, was used as a model mAb to examine the deglycosylation activity and potential transglycosylation activity of the enzymes. The major Fc glycans of commercial rituximab are core-fucosylated biantennary complex type oligosaccharides carrying 0-2 galactose moieties named G0F, G1F, and G2F glycoforms, respectively, as revealed in FIG. 4C. Treatment of rituximab with the EndoS2-CPD fusion protein (here, referred as wild-type EndoS2 or EndoS2) resulted in a rapid deglycosylation to give the deglycosylated rituximab that bears the fucosylated GlcNAc disaccharide moiety (Fucα1, 6GlcNAc) at the glycosylation sites (N297). These results confirm the remarkable Fc glycan-hydrolyzing activity of the wild-type EndoS2 on intact IgG, implicating its usefulness in the first step for glycosylation remodeling of mAbs. The transglycosylation potential of Endo-S2 mutants were then examined using the deglycosylated rituximab as the acceptor and the complex, high mannose, and hybrid glycan oxazolines as the donor substrates, as depicted in FIG. 3. The glycosylation remodeling process was monitored by sodium dodecylsulfate polyacrylamide gel electrophoresis (SDS-PAGE) and liquid chromatography mass spectrometry (LC-MS) analysis, as shown in FIG. 4. The heavy chain and light chain of rituximab appeared at approximately 50 KDa and approximately 25 KDa, respectively, under reducing conditions (lane 1, in FIG. 4A). After deglycosylation with wild-type EndoS2, the heavy chain appeared as a single band at approximately 48 KDa, suggesting the removal of the two N-glycans (each from a heavy chain) in rituximab (lane 2, in FIG. 4A). Incubation of the deglycosylated rituximab (1) and the sialo complex type glycan oxazoline (2)(donor/acceptor, 20:1, molar ratio) with mutant EndoS2-D184Q gave a transglycosylation product (5), FIG. 4E), the heavy chain of which appeared as a single band that was about 2 KDa larger than that of the deglycosylated rituximab (1) (FIG. 4A, lane 3). This result suggests that a new N-glycan was attached to each of the Fc heavy chains. Interestingly, an essentially quantitative transglycosylation for the Fc domain of the intact antibody was achieved within 1 h incubation.

The transglycosylation was further characterized by LC-MS analysis. The heavy chain and light chain of rituximab were separated under a LC-MS condition. Deconvolution of the light chain MS data gave a mass of 23 039 (FIG. 4B), which was consistent with the calculated mass of rituximab light chain (M=23 042 Da). [47] Deconvolution of the MS data of the heavy chain gave three distinct m/z species, 50508, 50669, and 50829, as shown in FIG. 4C, which were in good agreement with the theoretical mass of heavy chain glycoforms: G0F, M=50 515 Da; GIF, M=50 677 Da; and G2F, M=50 839 Da; respectively.[47] The deconvoluted electron spray ionization mass spectrometry (ESI-MS) of the heavy chain of the deglycosylated rituximab (1) showed a single species at 49 411, as shown in graph c in FIG. 4D, which matched well with a heavy chain carrying a Fucα1, 6GlcNAc disaccharide moiety (calculated, M=49 420 Da). After glycosylation remodeling, a single peak at 51 414 was observed from the heavy chain of the transglycosylation product with complex glycan (5), with an addition of 2003 Da to the deglycosylated heavy chain of the rituximab, as shown in graph in FIG. 4E. This result indicates the attachment of a sialoglycan from the corresponding sugar oxazoline (2) to the heavy chain.

In addition to the sialylated complex type N-glycan oxazoline (2), the EndoS2 mutants were equally efficient to use the high mannose Man9GlcNAc core oxazoline (3) and the sialo hybrid type oxazoline (4) for rituximab glycoengineering, leading to the formation of the corresponding homogeneous glycoforms, (6) and (7), respectively (FIG. 4F and FIG. 4G). The deconvoluted ESI-MS of the heavy chain of the transglycosylation product (6) showed a single species at 51074, as shown in FIG. 4F, which matched well with the calculated molecular mass (M=51082 Da) of the rituximab heavy chain carrying a Man9GlcNAc2 glycan. Similarly, the deconvoluted ESI-MS of the heavy chain of transglycosylation product (7) showed a single species at 51080, as shown in FIG. 4G, which was in good agreement with the calculated molecular mass (M=50190 Da) of the rituximab heavy chain carrying a N3Man3GlcNAc2 glycan. The results set forth herein represents the first report of glycosylation remodeling of an intact IgG monoclonal antibody with an en bloc transfer of a full-size natural high mannose (Man9) and sialo hybrid type N-glycan to the Fc domain through a highly efficient deglycosylation-reglycosylation protocol enabled by the combined use of EndoS2 and EndoS2-based glycosynthase. After completion of the transglycosylation, the product could be purified by a simple protein A affinity chromatography, giving the well-defined homogeneous glycoform. Notably glycoengineering of intact rituximab with the transfer of biantennary complex type N-glycan to the Fc domain by using EndoS/EndoS-based glycosynthase has been reported. However, that system is inefficient in transfer high mannose and hybrid type glycan to antibody. The development of EndoS2/EndoS2-glycosynthethase system significantly expanded the scope of glycan specifies of chemoenzymatic glycoengineering of antibody.

Figure 5:
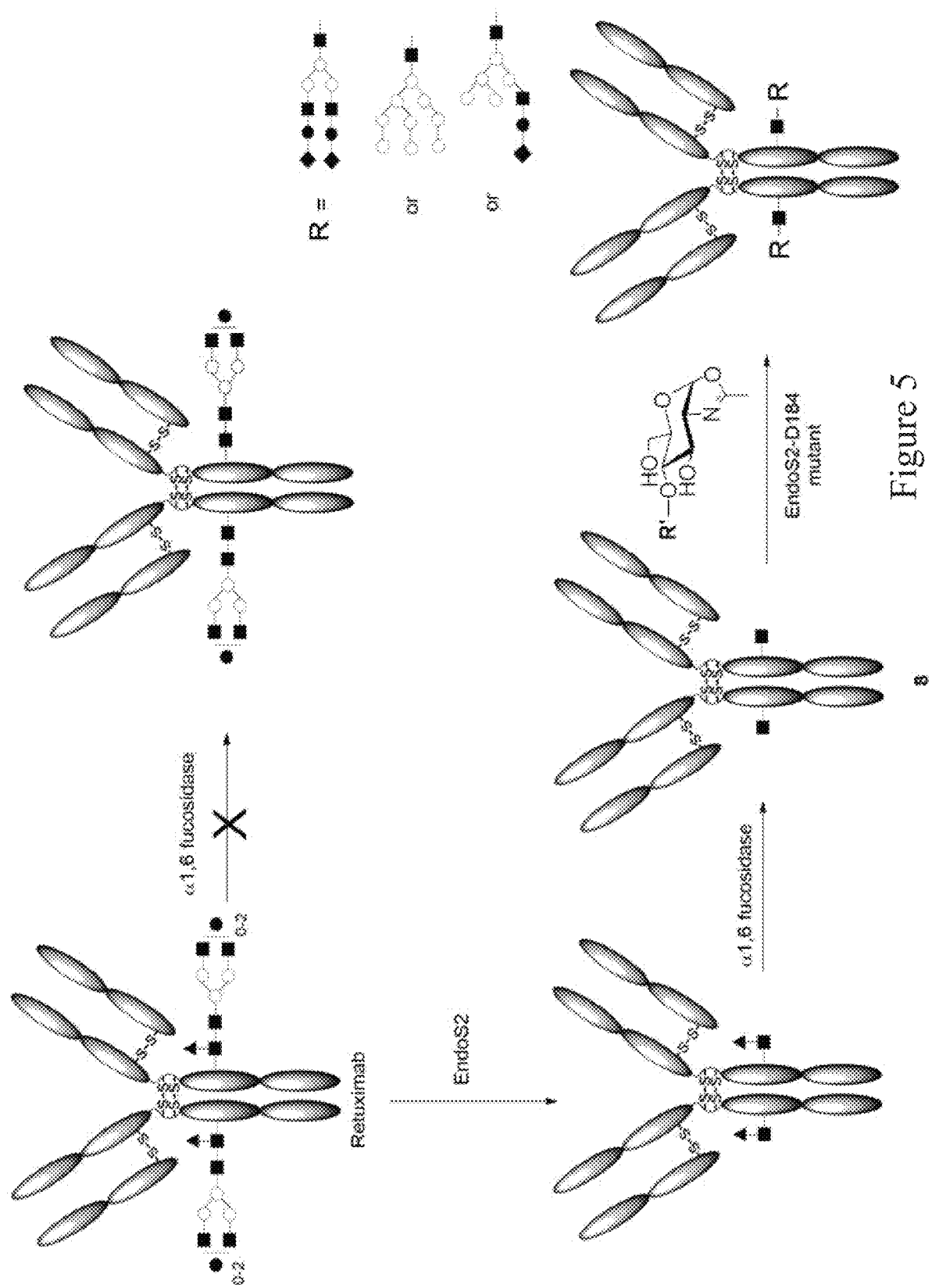
FIG. 5 shows the scheme for enzymatic remodeling to non-fucosylated homogeneous complex, high mannose and hybrid glycoform of rituximab.
Figure 6:
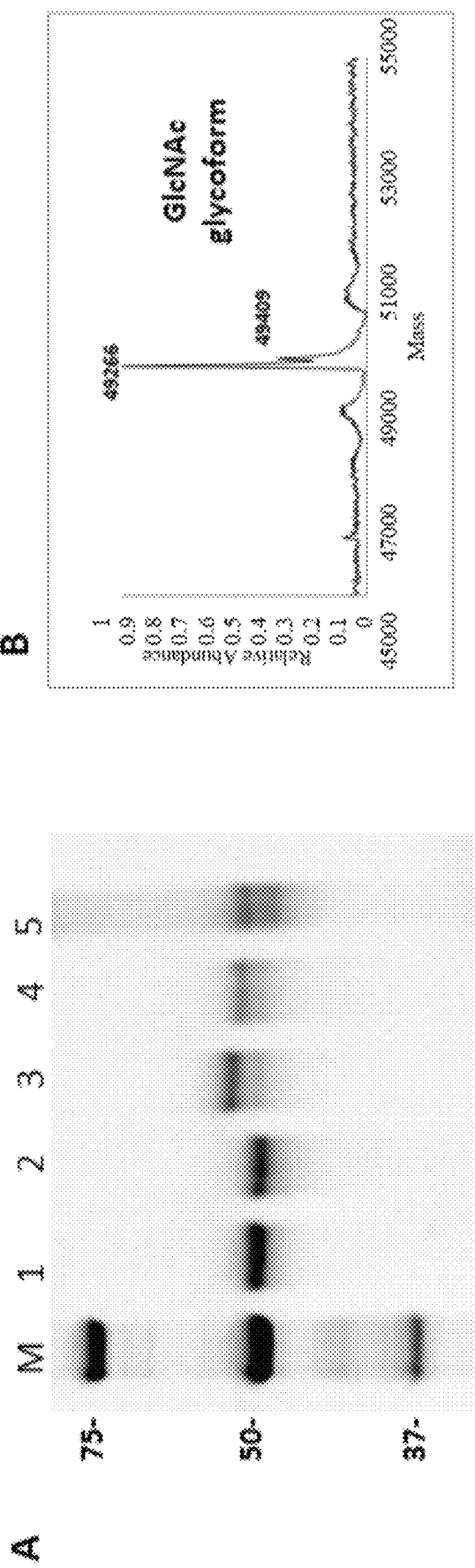
FIG. 6 shows SDS-PAGE and ESI-MS analysis of glycoengineering of rituximab to the non-fucosylated G2 glycoform. (A) SDS-PAGE analysis: Lane 1, commercial rituximab; Lane 2, the EndoS2 de-glycosylated rituximab (1); Lane 3, the defucosylated product (8); Lane 4, the glycoengineered complex glycoform from the EndoS2-D184N catalyzed reaction (9); Lane 5, the glycoengineered Man9 glycoform from the EndoS2-D184N catalyzed reaction (10); Lane 6, the glycoengineered sialo hybrid glycoform from the EndoS2-D184A catalyzed reaction (11) (B) ESI-MS (after deconvolution) of the heavy chain of the defucosylated rituximab (8). (C) ESI-MS of the heavy chain of the glycoengineered complex type rituximab (9). (D) ESI-MS of the heavy chain of the glycoengineered Man9 rituximab (10). (E) ESI-MS of the heavy chain of the glycoengineered sialo hybrid type rituximab (11).
Figure 6:
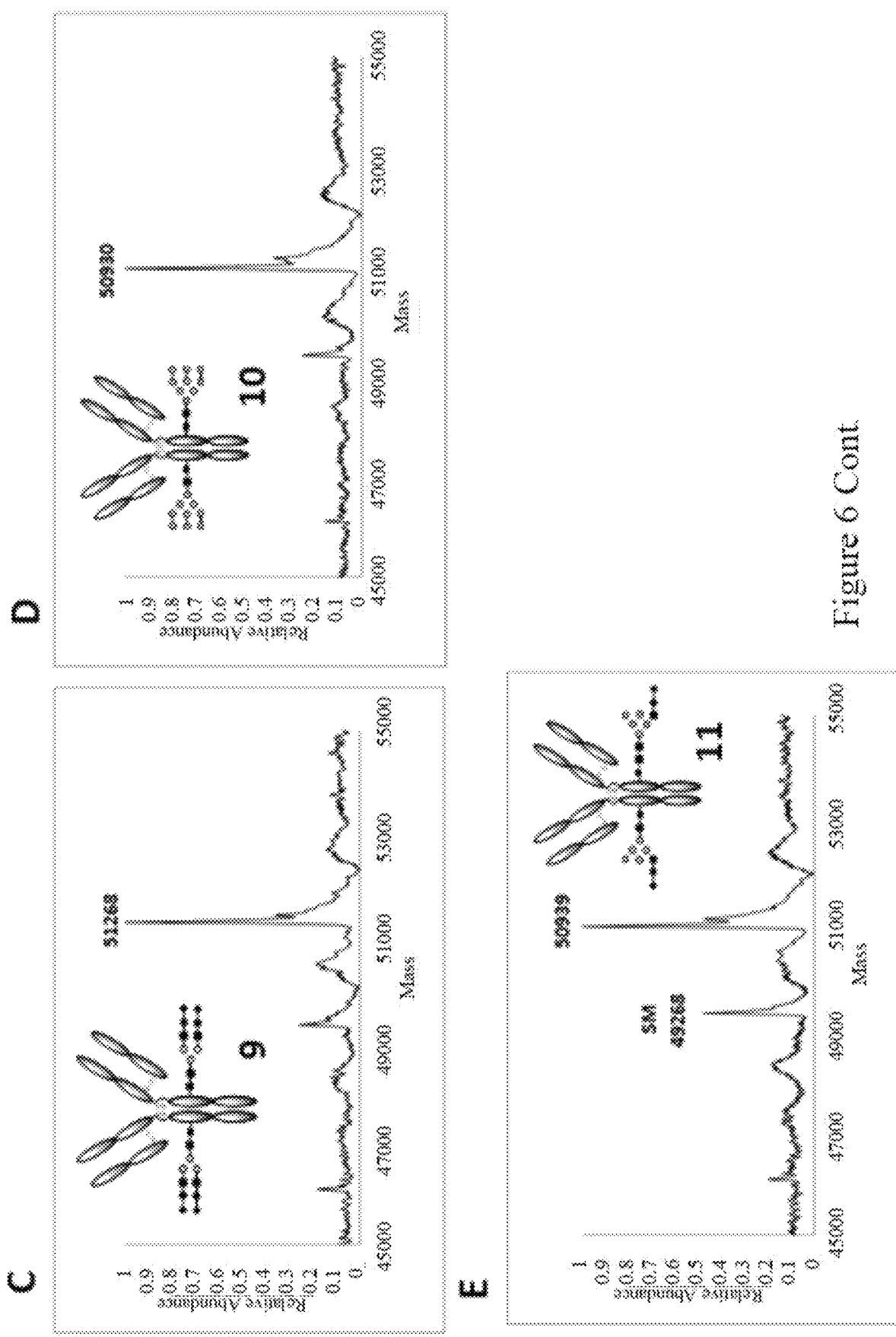

Glycoengineering of Rituximab to Provide Nonfucosylated Complex, High Mannose, and Hybrid Glycoforms For anticancer therapy, nonfucosylated IgG glycoforms are desirable as it has been previously demonstrated that mAbs with low-fucose contents of Fc N-glycans showed enhanced ADCC activity in vitro and enhanced anticancer efficacy in vivo, particularly for those patients carrying the low affinity F158 allele of the FcγIIIa receptor. [8, 39, 40, 49]. However, no α-fucosidases is available to remove the α1,6-fucose in the intact rituximab. The α-1,6-fucose moiety might be shielded by the Fc domain and/or the complex N-glycan, making it inaccessible to α-fucosidases. It was theorized that, upon deglycosylation, the resulting Fuc(α1, 6)GlcNAc glycoform of rituximab might be more accessible to α-fucosidases. Indeed, after deglycosylation with EndoS2, most of the α-1,6-fucose moiety could be removed by overnight incubation with α1,6-fucosidase from *Lactobacillus casei* to give the GlcNAc-containing rituximab (8). The result is confirmed with LC-MS (FIG. 6B). Next, it was determined that the glycosynthases EndoS2-D184A, EndoS-D184Q, or EndoS-D184N were also efficient to recognize the nonfucosylated GlcNAc in (8) for transglycosylation with complex (2), high mannose (3) or hybrid (4) oxazoline to provide the relatively homogeneous, nonfucosylated complex (9), high mannose (10) and hybrid (11) type glycoform in an essentially quantitative conversion (FIG. 5). The identity and purity of the glycoengineered product (9, 10, 11) were confirmed by SDS-PAGE and LC-MS analysis, as shown in FIG. 6. The defucosylated rituximab (8) showed a major peak at 49266 (FIG. 6B), confirming the removal of the fucose (calcd. for the heavy chain of GlcNAc-rituximab, M=49274 Da). The deconvoluted ESI-MS of the heavy chain of the transglycosylation product of complex type glycan (9) appeared as a major species at 51268 (FIG. 6C), which matched well with the calculated molecular mass (M=51276 Da) of the rituximab heavy chain carrying a sialylated biantennary complex type N-glycan, Sia2Gal2GlcNAc2Man3GlcNAc2. Similarly, LC-MS analysis of the heavy chain of transglycosylation product of the high mannose (10) and hybrid type glycan (11) appeared as a major species at 50930 (FIG. 6D) and 50939 (FIG. 6E), which matched well with the calculated molecular mass (50936 and 50944 Da), respectively. In the transfer of hybrid glycan oxazoline, approximately 33% of starting material is left untransferred. With optimization of reaction condition (increase of EndoS2 mutant concentration, addition of more oxazoline, etc.), the reaction should be able to push to completion. It just seems fucosylated rituximab (1) is a more preferred acceptor than non-fucosylated one (8). In a comparative study, it was also found that mutants D184A, D184N, and D184Q had a faster transglycosylation reaction on the fucosylated GlcNAc-rituximab (1) than the nonfucosylated acceptor (8) (data not shown). Taken together, these experimental results revealed a combined enzymatic approach to making the nonfucosylated complex, high mannose and hybrid type homogeneous (or relatively homogeneous) glycoform from commercially available monoclonal antibodies. The resulting nonfucosylated rituximab is expected to gain improved ADCC and CDC effector functions as suggested by previously studies. [8, 42, 49].

Comparison of the Transglycosylation Activity of Different Mutants of EndoS2 D184

Figure 7:
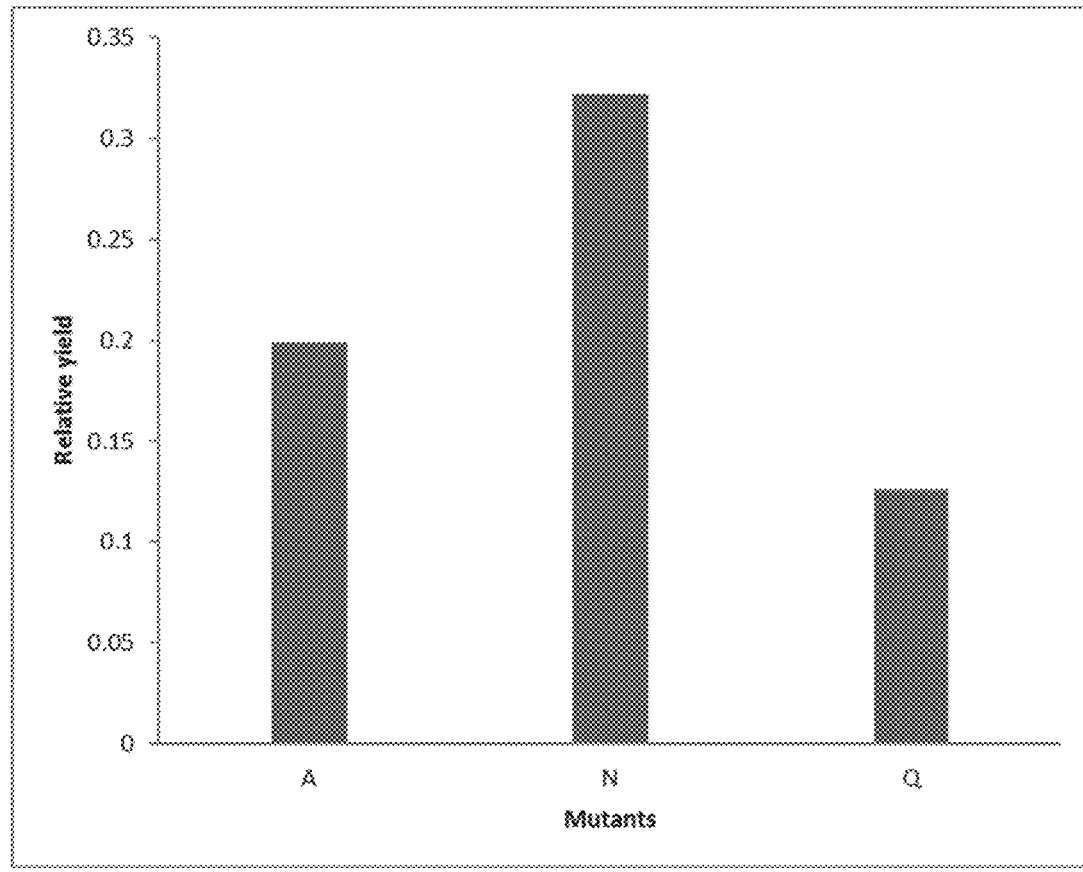
FIG. 7 shows the comparison of transglycosylation activity of alanine, asparagine, glutamine mutants of EndoS2 D184 of complex type glycan oxazoline to fucosylated rituximab.

The activities of EndoS2-D184A, D184N, and D184Q were compared of transferring sialo bianntenary complex glycan oxazoline (2) to fucosylated GlcNAc-rituximab (1). With the same reactive conditions, the asparagine (N) mutant transferred more than 30% of oxazoline to the acceptor in five minutes while the alanine (A) and glutamine (Q) mutants transfer less than 20% (FIG. 7). It seems the N mutant is more active than A and Q mutants in the transfer of complex type oxazoline.

Cloning, Expression and Characterization of Endo-S2 cDNA sequence encoding Endo-S2 (44-843 of SEQ ID NO: 1) (The Genbank accession number for the Endo-S2 gene (ndoS2) is ACI61688) was cloned into a pET22b-CPD vector, which adds to the C-terminus of the expressed protein the cysteine protease domain (CPD) of the *Vibrio cholerae* MARTX toxin and a 10× histidine tag [35] (SEQ ID NO 22). It was recently reported that a high level, soluble expression of Endo-F3 and its mutants could be achieved using this vector [32]. In the alternative, the cDNA sequence for encoding Endo-S2 may include (1, and 44-843 amino acids of SEQ ID NO: 1). Following a similar method, the Endo-S2 was successfully expressed in *E. coli* and readily purified using immobilized metal ion affinity chromatography (IMAC) to obtain the soluble enzyme with a yield of more than 20 mg/L. The recombinant Endo-S2 showed high hydrolysis activity as demonstrated by its rapid deglycosylation of commercial rituximab, which was monitored by LC-MS analysis.

Generation of Glycosynthase Mutants from Endo-S2

Glycosynthase mutants from endoglycosidases of both GH85 and GH18 family were generated by site-directed mutation at a key residue that is responsible for promoting the formation of the oxazolinium ion intermediate during hydrolysis, which proceeds in a substrate-assisted mechanism. These include a key asparagine residue for endoglycosidases Endo-A (Asn171) [36], Endo-M (Asn175) [37, 38], and Endo-D (Asn322) [24] of the GH85 family, or a key aspartic acid residue for the GH18 family endoglycosidases Endo-S (Asp233) [25] and Endo-F3 (Asp-165) [32]. Sequence alignment of Endo-S2 and Endo-S revealed that the Asp-184 of Endo-S2 was the residue equivalent to the Asp233 of Endo-S essential for promoting oxazolinium ion formation in hydrolysis (FIG. 2). To generate efficient glycosynthase mutants from Endo-S2, the Asp-184 was systematically replaced in the truncated expressed protein comprising the residues of 44 to 843) with other 19 natural amino acid residues using site-directed mutagenesis. Notably, it is envisioned that unnatural proteins may also be used in the substitution. The resulting 19 D184 mutants were also expressed as soluble proteins in the pET22bCPD vector and purified using immobilized metal ion affinity chromatography, in the same way as demonstrated for the wild type enzyme. The expression of the mutant enzymes gave comparable yields (15-20 mg/L) as the expression of the wild type enzyme.

Notably, it is envisioned that unnatural proteins may also be used in the substitution. Examples of unnatural amino acids that can be used by the translation system include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof.

Figure 8:
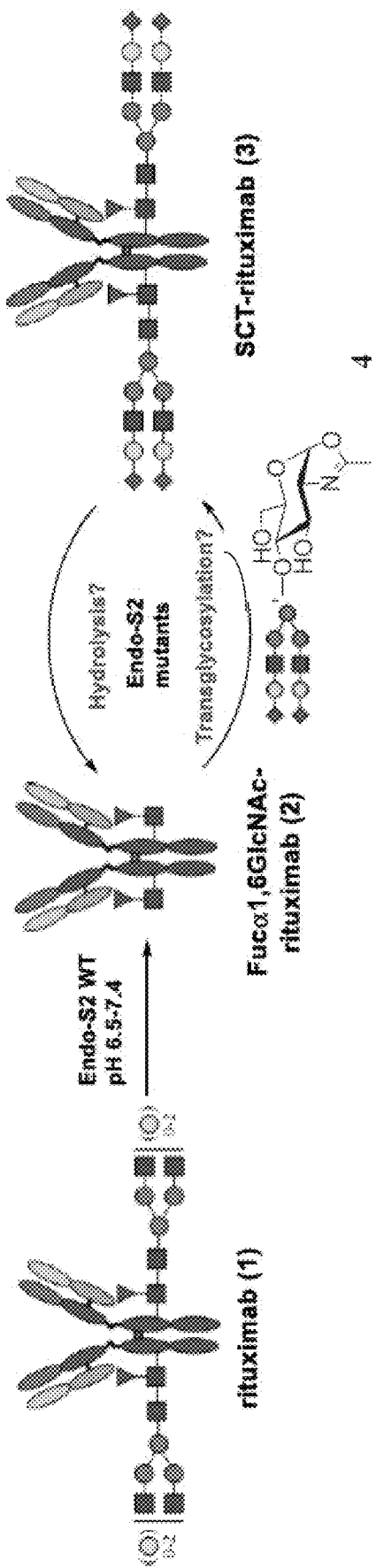
FIG. 8 show a schematic presentation of the hydrolysis and transglycosylation by Endo-S2 and its mutants using rituximab as the substrate. Fuc α1,6GlcNAc-rituximab, the deglycosylated rituximab carrying the core-fucosylated GlcNAc moiety at the glycosylation site; SCT-rituximab; the sialyl complex type glycoform of rituximab.

Comparative Study on the Hydrolysis and Transglycosylation Activity of 19 Mutants and WT The hydrolysis activities on Fc N-glycans in an intact antibody and the transglycosylation activities with glycan oxazoline were assessed by following the scheme as shown in FIG. 8. The results indicate that most of the mutants at the D184 residue led to significantly reduced or completely diminished hydrolysis activity on Fc N-glycan. Among them, the D184F, D184H, D184K, D184R, and D184W mutants were completely devoid of hydrolytic activity, while several other mutants, including D184C, D184E, D184G, D184N, D184S, D184Y, were found to still retain significant hydrolysis activity (Table 1). On the other hand, the evaluation of transglycosylation indicated that almost all the mutants possessed transglycosylation activity when using the deglycosylated rituximab as the acceptor and a biantennary complex type glycan oxazoline as the donor substrate, but the activities varied significantly among different mutants (FIG. 8, Table 2). Among others, the D184C, D184M, D184G, D184E, D184Y, D184S, and D184A were found to be the most active mutants. However, the D184C, D184G, D184E, D184Y, D184S, and D184A also demonstrated significant residual hydrolytic activity. The most interesting mutant is D184M, which retained only marginal hydrolytic activity but showed extraordinarily high transglycosylation activity (only second to D184C), making it one of the best glycosynthase mutants to choose for glycosylation remodeling.

Figure 9:
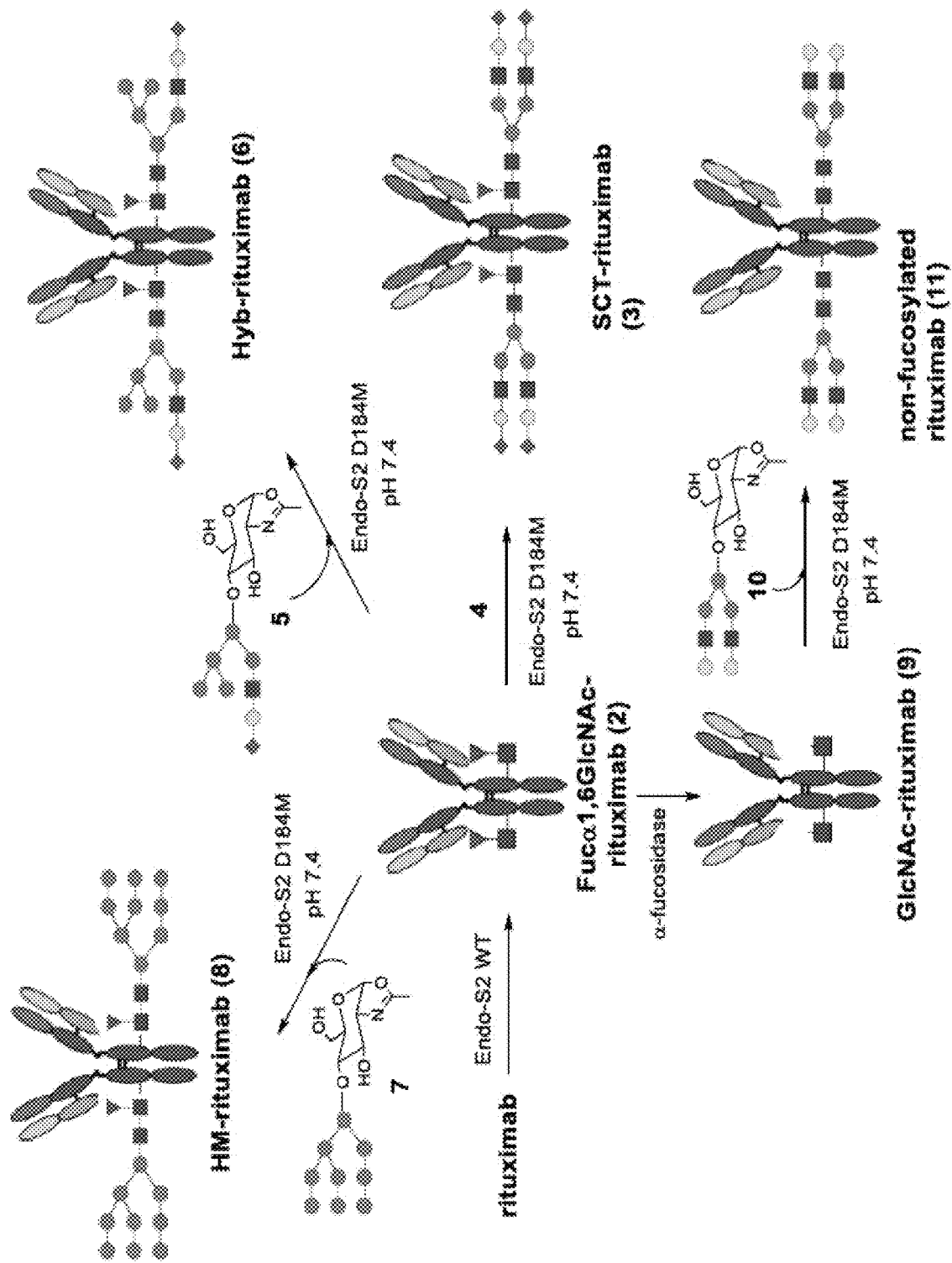
FIG. 9 shows the evaluation of substrate specificity of Endo-S2 mutants on various glycans (HM, CT, and hybrid type). GlcNAc-rituximab, the rituximab glycoform carry only the first GlcNAc moiety at the Fc glycosylation site; Fuc α1,6GlcNAc-rituximab, the deglycosylated rituximab carrying the core fucosylated GlcNAc moiety at the glycosylation site; SCT-rituximab; the sialyl complex type glycoform of rituximab; HM-rituximab, the high-mannose type glycoform of rituximab; Hyb-rituximab, the hybrid type glycoform of rituximab.
Figure 10:
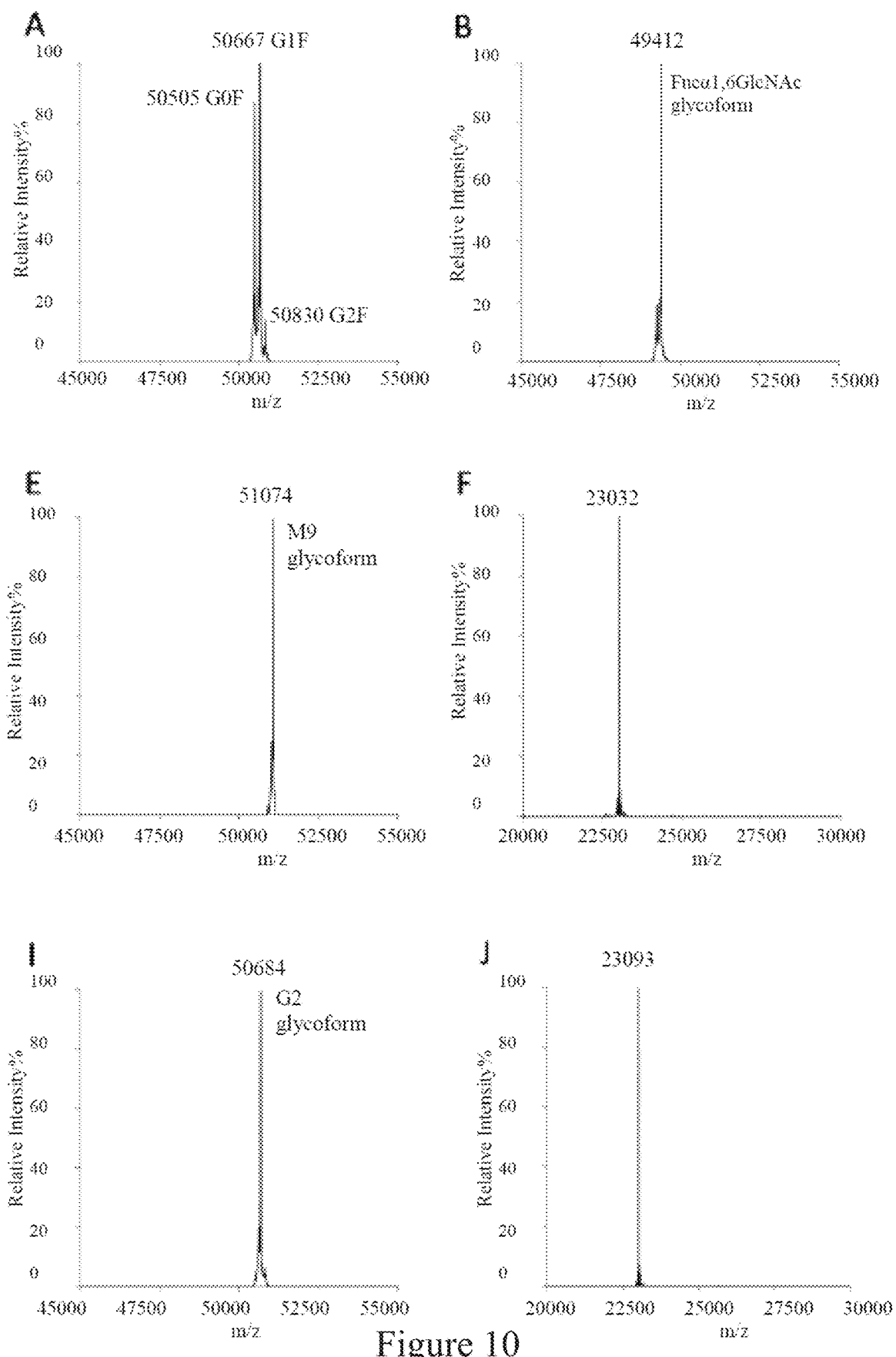
FIG. 10 shows the ESI-MS analysis of the glycosylation remodeling of rituximab using Endo-S2 D184M. A) ESI-MS (after deconvolution) of the heavy chain of the commercial rituximab; B) ESI-MS of the heavy chain of the Fuc α1,6GlcNAc-rituximab (2); C and D) ESI-MS of the heavy chain and light chain of transglycosylation product (3) (SCT-rituximab), respectively; E and F) ESI-MS of the heavy chain and light chain of transglycosylation product (8) (HM-rituximab); G and H) ESI-MS of the heavy chain and light chain of transglycosylation product (6) (Hyb-rituximab); I and J) ESI-MS of the heavy chain and light chain of transglycosylation product (11) (non-fucosylated rituximab).
Figure 10:
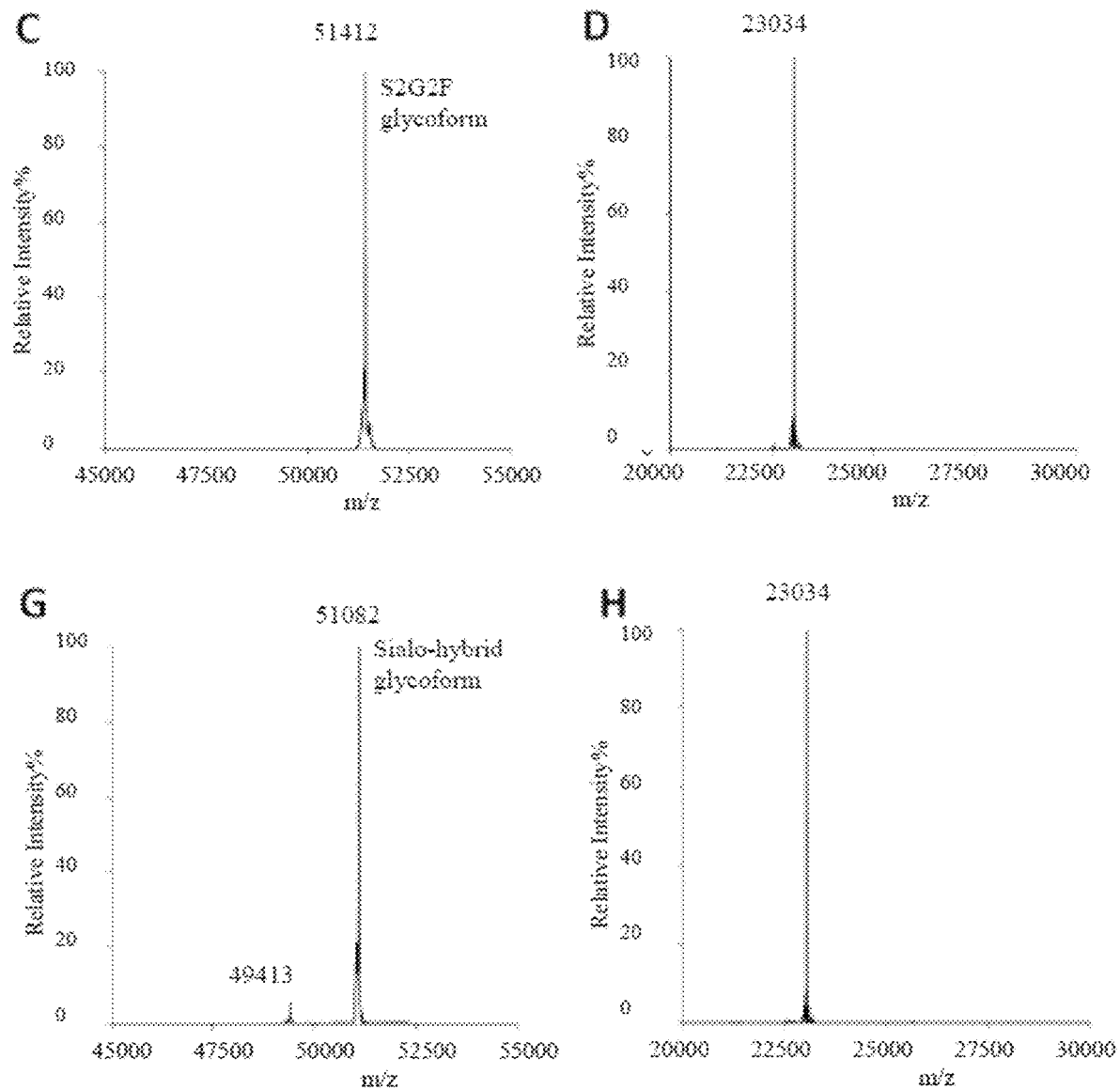

Endo-S2 Glycosynthases Show Remarkably Broad Substrate Specificity in Transglycosylation Rituximab, a therapeutic monoclonal antibody, was used as a model to examine the transglycosylation activity of the Endo-S2 D184 mutants. The major Fc glycans of commercial rituximab are core-fucosylated bi-antennary complex type oligosaccharides carrying 0-2 galactose moieties named G0F, G1F, and G2F glycoforms, respectively. The general glycosylation remodeling approach was presented in FIG. 9 and the reaction products were assessed by LC-MS analysis (FIG. 10). Treatment of rituximab (1) with wild-type Endo-S2 resulted in complete deglycosylation of rituximab, as demonstrated by the conversion of the glycoform mixtures (G0F, G1F, and G2F) found in commercial rituximab (FIG. 10A) to the Fucα1,6GlcNAc-glycoform (2) of rituximab (FIG. 10B). The Fucα1,6GlcNAc-rituximab (2) was purified away from the WT endoglycosidase and released glycans by Protein A affinity chromatography and used as the acceptor in the transglycosylation reactions. It was found that EndoS2 D184M was able to efficiently transfer the sialylated biantennary complex-type (SCT) N glycan from the corresponding glycan oxazoline (4) to the Fucα1,6GlcNAc-rituximab acceptor (2) to form the S2G2F glycoform of rituximab (3). The reaction could be readily pushed to completion with 20 molar equivalent (i.e., 10 molar equivalent per monomeric Fc domain) of the glycan oxazoline. The reaction yield was estimated by LC-MS analysis to be over 95% as almost no starting material was detected, which confirmed the completion of the transglycosylation. LC-MS analysis of the transglycosylation products (3) carrying the SCT N-glycan revealed that the heavy chain of (3) appeared as a single species at 51412 (deconvolution data), which is in good agreement with the calculated molecular mass (M=51421 Da) for the heavy chain carrying a SCT N-glycan (with core-fucose), respectively (FIG. 10C).

In addition to the complex-type N-glycan, the specificity of Endo-S2 was further tested with high-mannose-type (HM) Man9GlcNAc oxazoline (7) and sialo hybrid-type (Hyb) Neu5AcGalGlcNAcMan5GlcNAc oxazoline (5) as donor substrate in the transglycosylation reactions. The reactions led to the formation of the corresponding homogeneous glycoforms, (8) and (6), respectively (FIG. 10E, 10G). The deconvoluted ESI-MS of the heavy chain of the transglycosylation product (8) showed a single species at 51074, as shown in FIG. 10E, which matched well with the calculated molecular mass (M=51081 Da) of the rituximab heavy chain carrying a Man9GlcNAc2 glycan. Similarly, the deconvoluted ESI-MS of the heavy chain of transglycosylation product (6) showed a single species at 51082, as shown in FIG. 10G, which was in good agreement with the calculated molecular mass (M=51090 Da) of the rituximab heavychain carrying a Neu5AcGalGlcNAcMan5GlcNAc2 glycan. Under the same conditions, it was found that the previously reported Endo-S mutants, including D233A and D233Q mutants of Endo-S [25] showed only marginal transglycosylation activity with high mannose and hybrid type N-glycans, although they could efficiently transfer biantennary complex type N-glycan. In addition, the recently reported D165A mutant of Endo-F3 [32] was unable to transfer the high-mannose or hybrid type Nglycans but could work on bi- and tri-antennary complex type sugars. Thus, these Endo-S2 derived mutants represent the first glycosynthases that can efficiently transfer high-mannose and hybrid type N-glycans to core-fucosylated GlcNAc acceptor in an intact antibody. It should be mentioned that the Endo-A mutant (N171A and N171Q) could transfer high-mannose type N-glycan to GlcNAcFc domain, but they were unable to use corefucosylated GlcNAc-Fc as an acceptor [22, 23, 36]. These studies also show that the combined use of wild type Endo-S2 and Endo-S2 glycosynthase mutants provides a particularly efficient glycosylation remodeling approach to various homogeneous glycoforms of antibodies starting from a single precursor.

Endo-S2 Based Glycosylation Remodeling for Making Nonfucosylated Glycoforms

For anticancer therapy, nonfucosylated IgG glycoforms are desirable as it has been previously demonstrated that mAbs with low-fucose contents of Fc glycosylation showed enhanced ADCC activity in vitro and enhanced anticancer efficacy in vivo, particularly for those patients carrying the low affinity F158 allele of the FcγIIIa receptor [8, 9, 39, 40]. To test whether Endo-S2 can glycosylate non-fucosylated IgG, Fucα1,6GlcNAc-rituximab (2) was incubated with a recombinant α1,6-fucosidase from *Lactobacillus casei* [41] to give GlcNAc-rituximab (9) lacking the core-fucose. Endo-S2 D184M catalyzed transglycosylation of GlcNAc-rituximab (9) was carried out with a sialo biantennary complex-type (CT) N-glycan oxazoline (10). It was found that the D184M mutant could efficiently transfer the N-glycan to the GlcNAc acceptor in the antibody to give the fully galactosylated and nonfucosylated glycoform (11) in an essentially quantitative conversion. The deconvoluted ESI-MS of the heavy chain of transglycosylation product (11) showed a single species at 50684, as shown in FIG. 10I, which was in good agreement with the calculated molecular mass (M=50693 Da) of rituximab heavy chain carrying a fully galactosylated biantennary complex type N-glycan without the core-fucose. In addition to the confirmation of site-specific glycosylation of the heavy chain by LC-MS analysis combined with enzymatic transformation, the light chain of the transglycosylation products (3, 6, 8, 11) also appeared as a single species at 23034, which matches the calculated molecular mass of the light chain of rituximab (M=23039 Da) (FIG. 10D, F, H, J) without any modifications. These results indicated that there were no non-enzymatic modifications occurring on the heavy and light chains except the attachment of the transferring Nglycan at the GlcNAc acceptor at the Fc domain during the Endo-S2 catalyzed glycosylation remodeling processes. It should be pointed out that the fully galactosylated and non-fucosylated glycoform of rituximab (11) was previously shown to have at least 20-fold enhanced affinity for the FcγIIIA receptor in comparison with the commercial rituximab, which is an indication of a significantly enhanced ADCC [25].

Figure 11:
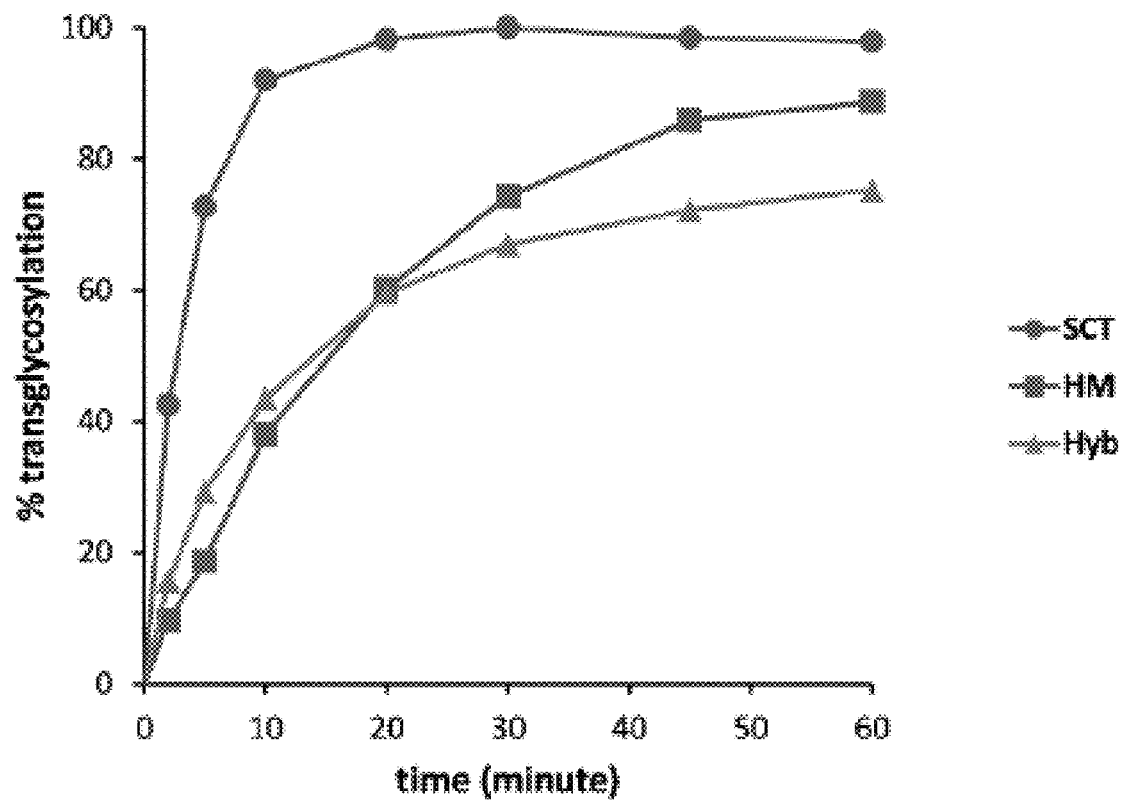
FIG. 11 shows a comparison of transglycosylation efficiency of different types of glycans by Endo-S2 D184M mutant. The transglycosylation reaction was carried out using deglycosylated rituximab (2) as the acceptor and different types of glycan oxazolines as the donor substrate under the catalysis of Endo-S2 D184M (0.05 mg/ml). The molar ratio of donor to acceptor was 20:1. The data sets presented here are representative of two independent experiments.

Comparison of Transglycosylation Efficiency on Different N-Glycan Substrates by Endo-S2 D184M Mutant To further characterize the N-glycan substrate preference of Endo-S2 D184M, three parallel transglycosylation reactions were carried out with the N-glycan oxazolines of the complex (SCT) type, high-mannose (HM) type, and hybrid (Hyb) type, respectively. The reaction progresses were monitored by LC-MS analysis of reaction aliquots taken at multiple time-points and the results were summarized in FIG. 11. Under the same reaction conditions, the transglycosylation reaction with SCT-oxazoline (4) was completed within 20 minutes to give S2G2F-rituximab (3), while the transglycosylation with HM-oxazoline (7) and Hyb-oxazoline (5) were much slower. These results suggest that Endo-S2 D184M prefers complex-type over the high-mannosetype and hybrid-type N-glycan despite of having a remarkably relaxed N-glycan specificity.

Figure 12:
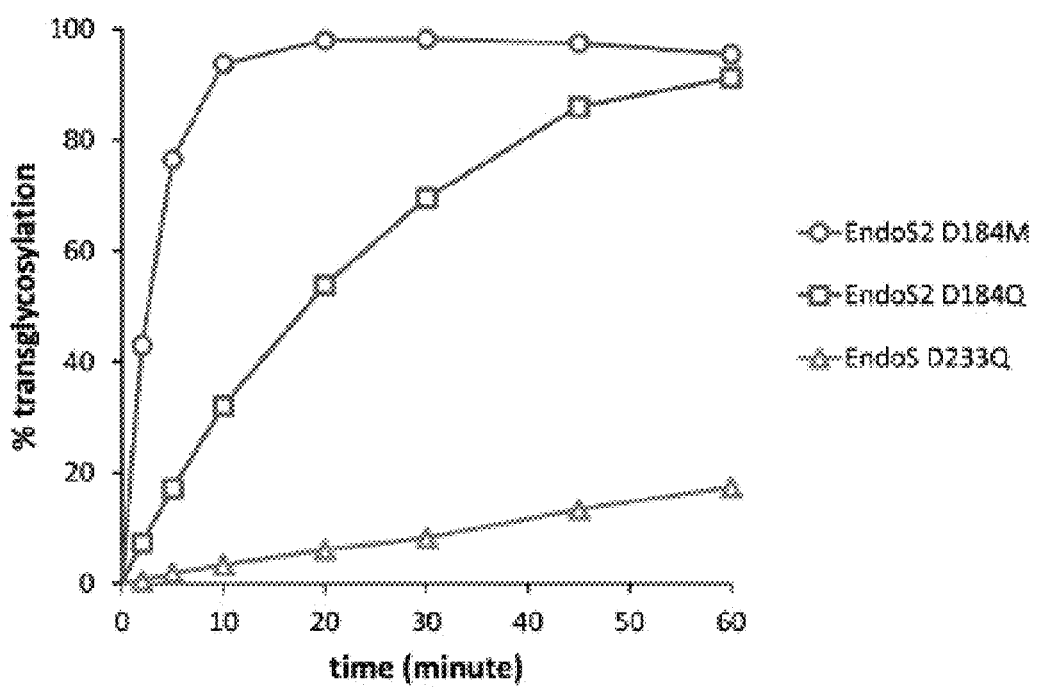
FIG. 12 show a comparison of the transglycosylation with SCT by Endo-S2 D184Q, Endo-S2 D184M, and Endo-S D233Q. The transglycosylation was performed using deglycosylated rituximab (2) as the acceptor and SCT glycan oxazoline (4) as the donor substrate under the catalysis of different endoglycosidase mutants at a fixed concentration of 0.05 mg/ml. The molar ratio of donor to acceptor was 20:1. The data sets presented here are representative of two independent experiments.

Comparison of the Transglycosylation Efficiency of Typical Endo-S2 and Endo-S Mutants Endo-S glycosynthase mutants D233Q and D233A were previously generated that transglycosylate rituximab efficiently with complex-type N-glycan oxazoline [25]. The EndoS D233 mutants have been recently used to generate homogeneous monoclonal antibodies for structural and functional studies [26-31]. To compare the transglycosylation efficiency of the glycosynthase mutants from Endo-S2 and Endo-S, the Endo-S D233Q mutant was selected, the equivalent Endo-S2 D184Q mutant and the Endo-S2 D184M mutant to catalyze three parallel transglycosylation reactions. The time-course of the transglycosylation reactions was monitored by LC-MS analysis and was summarized in FIG. 12. Under the reaction conditions, the D184M mutant of Endo-S2 showed remarkably potent transglycosylation activity, and reached completion of the glycan transfer within 10 min. The other Endo-S2 mutant could also transfer the glycan smoothly and reached the completion within one hour. However, the corresponding Endo-S mutant (D233Q) was much less efficient, reaching about 10% of transglycosylation at one hour under the same conditions (FIG. 12). As demonstrated in a separate experiment, much more (10-fold) of Endo-S D233Q mutant and a larger excess of the glycan oxazoline were required to achieve the same level of the transglycosylation catalyzed by the Endo-S2 D184Q mutant, and the D184M mutant of Endo-S2 was even much more efficient than the D184Q mutant. These studies suggest that the newly discovered Endo-S2 D184 mutants are superior to the previously reported Endo-S mutants for antibody glycosylation remodeling in both efficiency of reactions and the breadth of substrate diversity.

Figure 13:
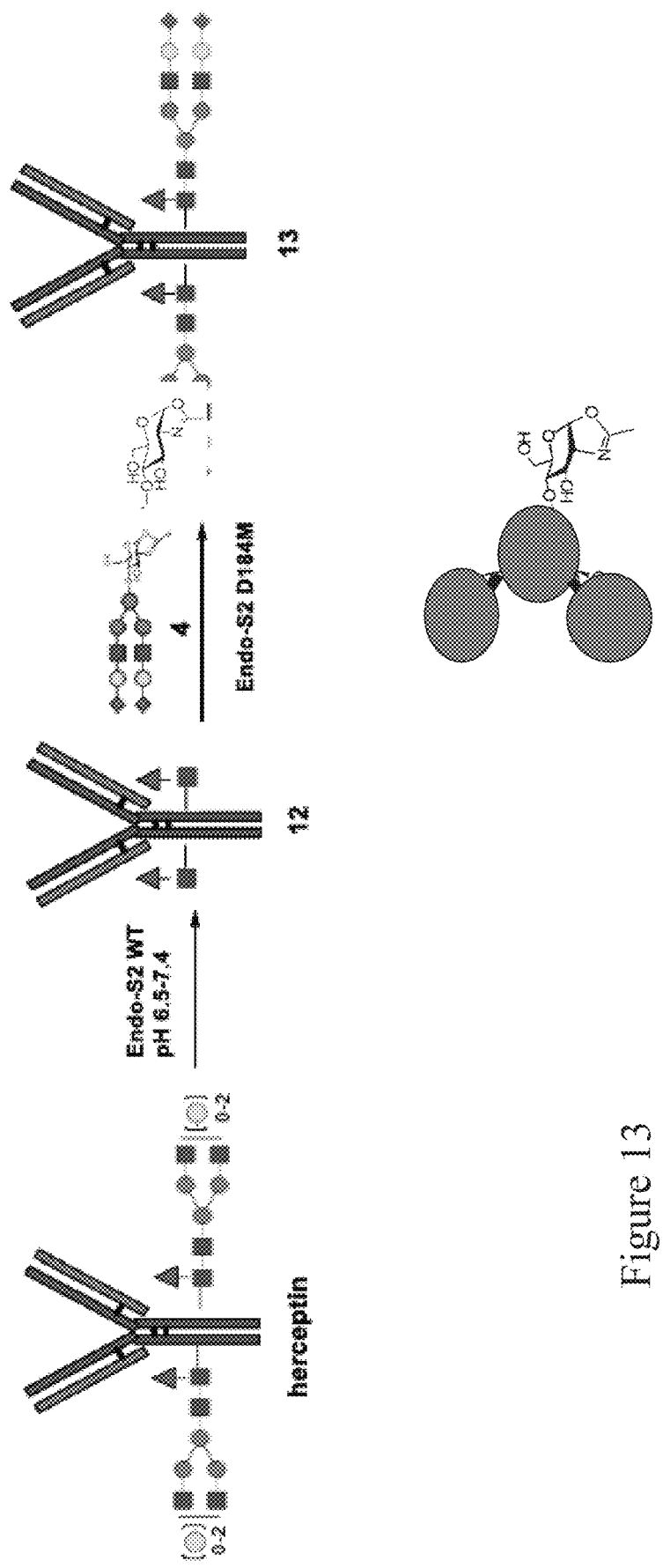
FIG. 13 shows glycosylation remodeling of herceptin (trastuzumab) using a pair of Endo-S2 enzymes (Endo-S2 WT and Endo-S2 D184M mutant) and A) ESI-MS of the heavy chain of commercial trastuzumab (Herceptin); B) ESI-MS of the heavy chain of deglycosylated herceptin (12); C) ESI-MS of the heavy chain of transglycosylation product 13 (S2G2F-trastuzumab); D) ESI-MS of the light chain of transglycosylation product (13); E) ESI-MS of the heavy chain of transglycosylation product (13) after PNGase F catalyzed deglycosylation.
Figure 13:
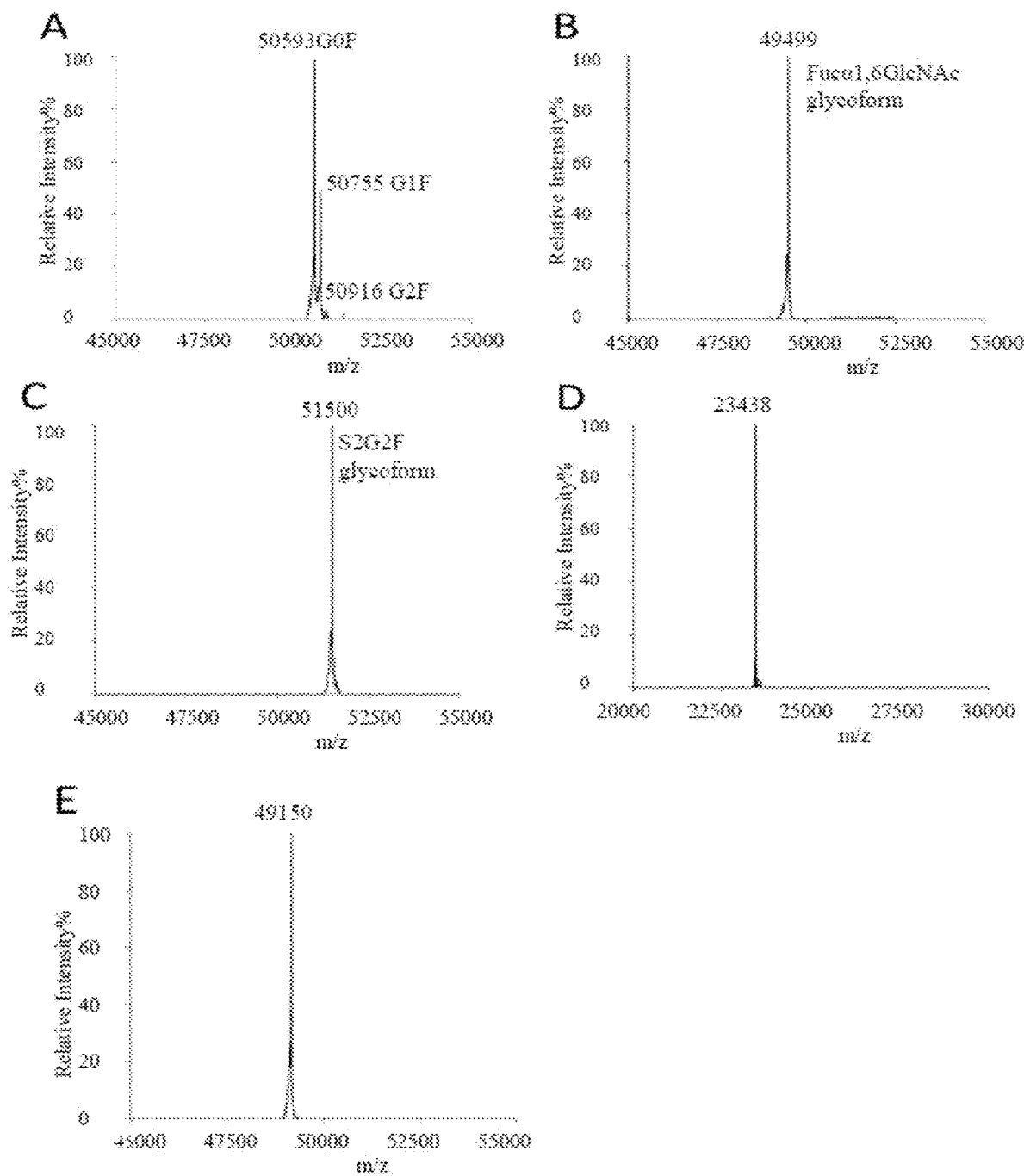

Glycosylation Remodeling of Trastuzumab (Herceptin) Using a Pair of Endo-S2 Enzymes To demonstrate that the observed enzymatic properties of Endo-S2 and its mutants are generally applicable to antibody glycosylation remodeling, glycosylation remodeling of another monoclonal antibody was performed, trastuzumab (Herceptin), which is widely used for treatment of breast cancer. The glycosylation remodeling was assessed by the synthesis of a sialylated glycoform of trastuzumab (FIG. 13). Treatment of trastuzumab with wild-type Endo-S2 resulted in complete deglycosylation, as demonstrated by the conversion of the glycoform mixtures (G0F, G1F, and G2F) found in commercial trastuzumab (FIG. 13A) to the Fucα1,6GlcNAc-glycoform (12) of trastuzumab (FIG. 13B). The deglycosylated trastuzumab was purified away from the endoglycosidase and released glycans by Protein A affinity chromatography and used as the acceptor in the transglycosylation reactions. Incubation of the Fucα1,6GlcNAc-trastuzumab (12) with the donor substrate SCT-oxazoline (4) in the presence of Endo-S2 D184M mutant resulted in rapid conversion of the deglycosylated trastuzumab (12) to the fully glycosylated trastuzumab (13). The reaction was essentially quantitative to give a single transglycosylation product (13). LC-MS analysis of the transglycosylation products (13) revealed that the heavy chain of (13) appeared as a single species at 51500 Da (deconvolution data) (FIG. 13C), indicating the attachment of a single sialylated N-glycan on the heavy chain. On the other hand, the light chain of the transglycosylation product (13) appeared as a single species at 23438, which is in a good agreement with the light chain of trastuzumab without any additional modifications (FIG. 13D).

To confirm that the N-glycan was attached specifically to the Asn-297 N-glycosylation site of the Fc domain, instead of other sites of the polypeptide backbone that might occur by nonenzymatic reactions as implicated in a recent publication [30], the transglycosylation product (13) was treated with PNGase F and examined the protein portion by mass spec analysis. PNGase F was highly specific and could release the Nglycans only when they were attached to the Asn side chain in an N-glycosylamide linkage at the conserved glycosylation site in N-glycoproteins. LC-MS analysis of the heavy chain of the PNGase F treated transglycosylation product (13) gave a single species of 49150 (deconvolution data), which corresponds to the polypeptide backbone of the heavy chain without any additional modifications (FIG. 13E). Taken together, these results clearly indicated that a single sialylated biantennary N-glycan was conjugated to the antibody heavy chain, and the intact N-glycan was attached at the conserved N-glycosylation site without any non-enzymatic glycations of the antibody. The highly efficient transformation catalyzed by the Endo-S2 glycosynthase mutants allowed much less reaction time and the use of much less excess of glycan oxazoline to achieve a quantitative conversion.

Described herein is the discovery of a new class of glycosynthases derived from an endoglycosidase (Endo-S2) of the *Streptococcus pyogenes* M49 serotype, which showed broader substrate specificity and much more potent transglycosylation activity for antibody glycosylation remodeling than the previously reported glycosynthases, such as those derived from Endo-A, Endo-M, Endo-S, and Endo-F3. These findings were enabled by a systematic mutagenesis at the critical residue D184, coupled with comparative analysis of the hydrolysis and transglycosylation activities of the resulting 19 mutants. The experimental data also revealed remarkable difference in both the hydrolysis and transglycosylation activities among the 19 mutants (Tables 1 and 2), which would be difficult to predict without this comparative study. Several notable mutants, including the D184M and D184Q mutants, were identified that showed high transglycosylation activity for glycosylation remodeling but retained only marginal hydrolysis activity.

Comparison of the hydrolysis and transglycosylation activities of the mutants reveals several interesting features. First, most of the mutants that showed high transglycosylation activity, including the D184C, D184G, D184E, D184Y, D184 S, and D184A mutants, also possessed relatively high residual hydrolysis activity. An exception is the D184M mutant, which demonstrated remarkable transglycosylation activity but retained only residual hydrolysis activity, making it the most efficient glycosynthase for glycosylation remodeling. Secondly, most the mutants with the D184 residue being replaced by amino acids with positively charged side chains (K, R, H) or bulky hydrophobic side chains (I, L, F, W) showed very low activities in both transglycosylation and hydrolysis. But, interestingly, the D184Y mutant retained the highest hydrolytic activity among all the mutants and also possessed a relatively high transglycosylation activity.

Another important discovery is the findings of the much broader substrate specificity of the Endo-S2 derived glycosynthases. It was found that the D184M and D184Q mutants, two notable Endo-S2 glycosynthases identified, were able to efficiently transfer all three major types of N-glycans including high-mannose type, complex type, and hybrid type, in antibody glycosylation remodeling. In addition, the Endo-S2 glycosynthases could recognize both core-fucosylated GlcNAc or nonfucosylated GlcNAc moiety at the Fc domain as an acceptor for transglycosylation. These findings significantly expand the scope of the glycosylation remodeling strategy. For example, the previously reported Endo-S and Endo-F3 are specific for complex type N-glycans and are unable to efficiently transfer high-mannose and hybrid type N-glycans, and the Endo-F3 is efficient only for core-fucosylated GlcNAc acceptor [32]. A direct comparison of the transglycosylation activity of the typical Endo-S2 and Endo-S glycosynthase mutants reveals that the Endo-S2 mutants are generally much more active than the corresponding Endo-S mutant. By an estimate of the initial rate, the D184Q mutant of Endo-S2 was at least 10-fold more active than the corresponding D233Q mutant of Endo-S, and the best Endo-S2 mutant, D184M, was estimated to be 100-fold better than the Endo-S D233Q mutant in glycosylating the deglycosylated rituximab (FIG. 12). Finally, in addition to the remodeling of rituximab, the highly efficient glycosylation remodeling of trastuzumab (Herceptin) by using a pair of Endo-S2 (the wild type and the D184M mutant) enzymes to give a single homogeneous glycoform without side reactions (FIG. 13) showcases the power of the newly discovered glycosynthases. It is expected that these highly efficient glycosynthases, which show also remarkably relaxed substrate specificity, will find a wide range of applications for producing various homogeneous glycoforms of antibodies for structural and functional studies, and for developing more effective antibody-based therapeutics as well.

Figure 14:
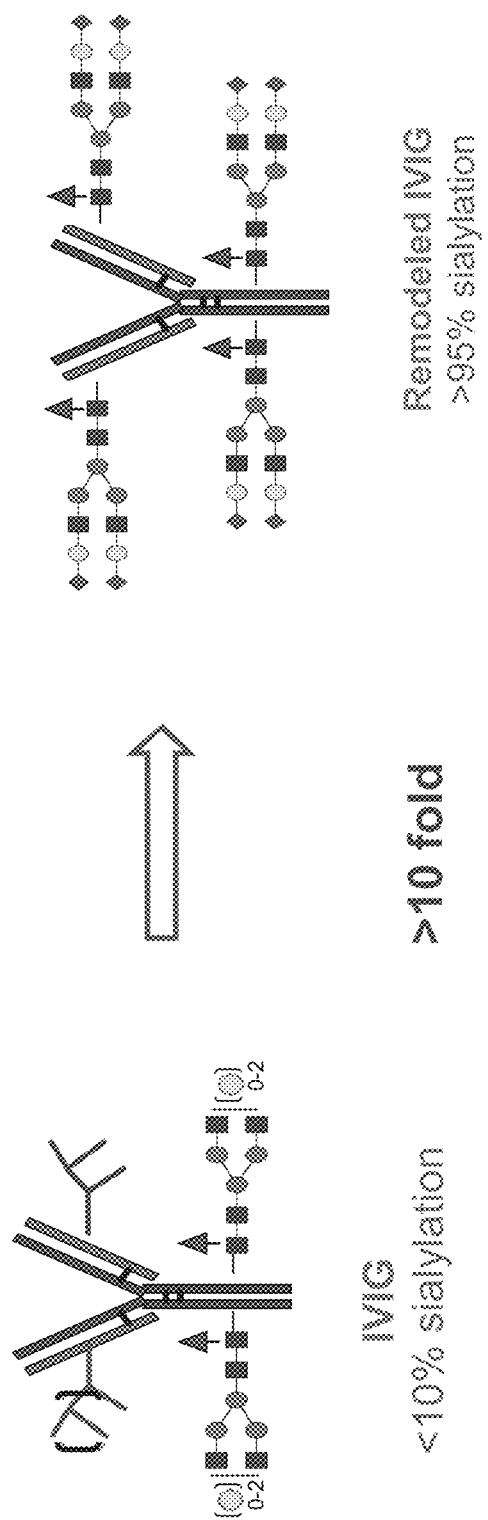
FIG. 14 shows Fc glycoengineering of IVIG for improved anti-inflammatory activity of IVIG.

FIG. 14 shows the use of the present invention to provide the desired homogeneous glycoforms of antibodies. IVIG is widely used for the treatment of Rheumatoid arthritis, but usually requires high doses such as (1-1.5 g/kg). However as shown in FIG. 14 the homogenous glycoform provides the benefits of reduced doses, enhance efficacy and reduced side effects. Such effects are due to a remodeled IVIG with greater than 95% sialylation due the use of the Endo S2 mutants of the present invention. Such improvement in glycosylation is applicable to glycoprotein hormones, cytokines (IL-2, interferons, etc.) and enzyme replacement therapy (lysosomal diseases).

Experimental Procedures

Materials—Monoclonal antibodies rituximab and trastuzumab (Herceptin) were products from Genentech Inc., (South San Francisco, Calif.). A sialo and sialoglycan complex type oxazoline was synthesized following the previously reported procedure [42]. The high mannose-type (HM) glycan (Man9GlcNAc) was prepared from soy bean flour by the previously described procedure [43]. The synthesis of hybrid type (Hyb) glycan (Neu5AcGalGlcNAcMan5GlcNAc) was achieved by a sequential enzymatic glycosylation of the Man5GlcNAc [43] under the catalysis of a β-1,2-GlcNAc transferase (GnT1) [44], a β-1,4-galactosyltransferase [45] and an α-2,6-Sialyltransferase [46]. The HM and Hybrid glycan oxazolines were synthesized following the previously described one-pot transformation procedure [42]. Endo-S D233Q from Streptococcus pyogenes was overexpressed and purified following our previous procedure [25].

Site-Directed Mutagenesis and Expression and Purification of Recombinant Endo-S2 cDNA encoding amino acids 44-843 of Endo-S2 from Streptococcus pyogenes NZ131 (serotype M49) was amplified by PCR and cloned into the pCPDLasso vector (a pET22b-CPD derivative) (35), wherein the sequence for the CPD (cysteine protease domain of the Vibrio cholerae MARTX toxin and histidine tag is set forth in SEQ ID NO: 22. For saturation mutagenesis of Asp-184 residue, a forward primer, 5'-CGTAAATTCGTGCTCAATNN-NAATATCTAGTCCATCGACACCACGATCAGTT-3', (SEQ ID NO: 23) and a reverse primer, 5'-AACT-GATCGTGGTGTCGATGGACTAGATATTNNNATT-GAGCACGAATTTACG-3' (SEQ ID NO: 24), were used. Mutations were confirmed by DNA sequencing. The plasmids containing mutated Endo-S2 genes were transformed into E. coli BL21 (DE3). For simultaneous production of 20 Endo-S2 D184 variants, the transformants were cultured in 20 mL 2×YT broth media supplemented with 100 µg/mL carbenicillin. Cultures were grown at 37° C. until the cells reached an OD600 of 0.8-1.0. Then 0.5 mM isopropyl β-D-1-thiogalactopyranoside (IPTG) was added to the culture to induce protein overproduction at 20° C. After 24 h the cells were harvested by centrifugation. The cell pellets were lysed by Bacterial Cell Lysis Buffer (Gold Biotechnology, Inc.) following manufacturer's instructions. 10× histidine (His10)-tagged EndoS2/CPD fusion proteins were purified with NiNTA Spin Columns (Qiagen). The purified EndoS2 proteins were desalted into PBS (pH 7.4) using centrifugal diafiltration with Amicon ultra filtration (10 kDa, Millipore). The protein purity was confirmed by SDS-PAGE and the concentration was measured on a NanoDrop 2000c using absorbance at 280 nm. For large-scale purification of selected Endo-S2 variants, 1 L culture is used. The cell lysate was applied to a HisTrap HP column (GE) and washed with PBS with 0.5 M NaCl and 20 mM imidazole (pH 7.4). Bound His-tagged protein was eluted with a gradient of 0-250 mM imidazole in PBS buffer. Eluted fractions containing Endo-S2 protein were pooled, concentrated and further purified by size exclusion chromatography through a HiPrep 16/60 Sephacryl S-200 HR column (GE).

Liquid Chromatography Mass Spectrometry (LC-ESI-MS) of IgG

The LC-MS analysis was performed on an Exactive Plus Orbitrap (Thermo Scientific). For intact antibody, the analysis was performed with a Waters XBridge™ BEH300 C4 column (3.5 2.1×50 mm) with a linear gradient of 5-90% MeCN containing 0.1% formic acid within 9 min at a flow rate of 0.4 ml/min. For analysis of antibody light chain and heavy chain, the IgG antibody were treated with 50 mM TCEP and heated at 37° C. for 20 min then subjected to LC-MS analysis with an Agilent Poroshell 300SB-C8 column (5 µm, 75×1 mm). The analysis was performed at 60° C. eluting with a linear gradient of 25-35% MeCN containing 0.1% formic acid within 6 min at a flow rate of 0.40 mL/min. The LC-MS analysis of PNGase F treated antibody glycoforms was performed in the same manner but included a 3-hr incubation with PNGaese F prior to TCEP treatment. Raw data was deconvoluted using MagTran (Amgen).

Deglycosylation of Rituximab by WildType Endo-S2 to Give (Fucα1,6)GlcNAc-Rituximab Commercial rituximab in its original buffer was incubated with wild-type Endo-S2 for one hour at 37° C. with an antibody-to-enzyme ratio of 500:1 (by weight). LC-MS analyses indicated the complete cleavage of the N-glycans on the heavy chain. The deglycosylated rituximab was purified by protein A chromatography. LC-MS: calculated for the heavy chain of (Fucα1,6)GlcNAc-rituximab (2), M=49420 Da; found (m/z), 49412 (deconvolution data).

Defucosylation of (Fucα1,6)GlcNAc-Rituximab by Bacterial α-Fucosidase

A solution of (Fucα1,6)GlcNAc-rituximab (2) in a Tris-HCl buffer (50 mM, pH 7.4) was incubated with the α-fucosidase AlfC from Lactobacillus casei at 37° C., with an antibody-to-enzyme ratio of 50:1. After 16 h incubation, LC-MS monitoring indicated the complete defucosylation of (Fucα1,6)GlcNAc rituximab (2) to give the product, GlcNAc-rituximab (9). The defucosylated rituximab was purified by protein A chromatography. LC-MS: calculated for the heavy chain of GlcNAc-rituximab (9) carrying a GlcNAc moiety, M=49274 Da; found (m/z), 49265 (deconvolution data).

Enzyme Assay

Assay for the hydrolysis activity of each Endo-S2 variant (0.1 µg) was performed at 30° C. with pure sialo-complex-type (S2G2F) rituximab 3 (10 µg, 7.0 µM) as substrate in PBS buffer (pH 7.4, 10 µl). An aliquot of each reaction mixture was diluted in 0.1% formic acid to stop the reaction and analyzed by LC-MS. Relative amount of the substrate and the hydrolysis products were quantified after deconvolution of the raw data and integration of the corresponding MS peaks using MagTran. The transglycosylation reaction with synthetic sugar oxazoline was assayed as follows: (Fucα1,6)GlcNAc-rituximab (100 µg, 69 µM), SCTox (1.38 mM, 20 equivalents) was incubated with 0.1 µg of each Endo-S2 variants at 30° C. in PBS (pH 7.4, 10 µl). The reactions were stopped and analyzed as in the hydrolysis assay stated above. Experiment of each mutant was repeated at least twice to ensure the consistency of the results.

Transglycosylation of Fuc1,6 GlcNAc Rituximab with SCT-Ox, Hyb-Ox and HM-Ox by Endo-S2 D184M: Synthesis of 3, 6, 8

A solution of Fuc1,6GlcNAc-Rituximab (1 mg, 69 µM) (2) and SCTox (1.38 mM, 20 eq) (4) was incubated with Endo-S2 D184M (5 µg) at 30° C. in 100 µl of 100 mM Tris Buffer (pH 7.4) for 15 min. LC-MS analysis indicated the completion of the transglycosylation reaction. The product (3) was purified using protein A chromatography. LC-MS: calculated for the heavy chain of (3) carrying the fully sialylated bi-antennary N-glycan, M=51421 Da; found (m/z), 51412 (deconvolution data).

A solution of Fuc1,6GlcNAc-Rituximab (1 mg, 69 µM) (2) and Hybox (1.38 mM, 20 eq) (5) was incubated with Endo-S2 D184M (5 µg) at 30° C. in 100 µl of 100 mM Tris Buffer (pH 7.4) for 30 min. Then another 10 eq of Hybox (5) was added and the reaction was monitored by LC-MS of aliquots. When LC-MS analysis indicated the near completion of the transglycosylation reaction, the product (6) was purified using protein A chromatography. LC-MS: calculated for the heavy chain of (5) carrying the sialylated hybrid-type Nglycan, M=51090 Da; found (m/z), 51082 (deconvolution data).

A solution of Fuc1,6GlcNAc-Rituximab (1 mg, 69 µM) (2) and HMox (1.38 mM, 20 eq) (7) was incubated with Endo-S2 D184M (5 µg) at 30° C. in 100 µl of 100 mM Tris Buffer (pH 7.4) for 30 min. Then another 10 eq of HMox (7) was added and the reaction was monitored by LC-MS of aliquots. When LC-MS analysis indicated the completion of the transglycosylation reaction, the product (8) was purified using protein A chromatography. LC-MS: calculated for the heavy chain of (12) carrying the high-mannose-type (Man9GlcNAc2) N-glycan, M=51081 Da; found (m/z), 51074 (deconvolution data).

Transglycosylation of GlcNAc-Rituximab with CT-Ox by Endo-S2 D184M: Synthesis of 11

A solution of GlcNAc-Rituximab (1 mg, 69 µM) (9) and CTox (1.38 mM, 20 eq) (10) was incubated with Endo-S2 D184M (5 µg) at 30° C. in 100 µl of 100 mM Tris Buffer (pH 7.4) for 30 min. LC-MS analysis indicated the completion of the transglycosylation reaction. The product (11) was purified using protein A chromatography. LC-MS: calculated for the heavy chain of (11) carrying the bi-antennary N-glycan, M=50693 Da; found (m/z), 50684 (deconvolution data).

Comparison of Transglycosylation Activity of Endo-S2 D184M Mutant Using SCT-, HM- and Hyb-Oxazoline as Donor Substrates In three separate reactions, Fuc1,6GlcNAc-Rituximab (0.2 mg, 69 µM) (2) together with SCTox (4), Hyb-ox (5) or HM-ox (7) (1.38 mM, 20 eq) was incubated with Endo-S2 D184M (1 µg) at 30° C. in 20 µl of 100 mM Tris Buffer (pH 7.4). An aliquot of reaction (0.5 µl) was taken out at several time points and dilute in 0.1% formic acid to stop the reaction. All aliquots were analyzed by LC-MS and % transglycosylation was calculated from the deconvoluted data.

Comparison of Transglycosylation Activity of Endo-S2 D184M, D184Q Mutants and Endo-S D233Q Mutant Using SCT-Oxazoline as the Donor Substrate In three separate reactions, Fuc1,6GlcNAc-Rituximab (0.2 mg, 69 µM) (2) and SCTox (4) (1.38 mM, 20 eq) was incubated with Endo-S2 D184M, Endo-S2 D184Q or Endo-S D233Q (1 µg) at 30° C. in 20 µl of 100 mM Tris Buffer (pH 7.4). An aliquot of reaction (0.5 µl) was taken out at several time points and dilute in 0.1% formic acid to stop the reaction. All aliquots were analyzed by LC-MS and % transglycosylation was calculated from the deconvoluted data.

Transglycosylation of Fuc1,6GlcNActrastuzumab with SCT-Ox by Endo-S2 D184M

Commercial trastuzumab (lyophilized powder) was dissolved in water and deglycosylated with wildtype Endo-S2 following the same method for rituximab. For transglycosylation, a solution of Fuc1,6GlcNAc-trastuzumab (12) (1 mg, 69 µM) and SCTox (4) (1.38 mM, 20 eq) was incubated with Endo-S2 D184M (5 µg) at 30° C. in 100 µl of 100 mM Tris Buffer (pH 7.4) for 15 min. LC-MS analysis indicated the completion of the transglycosylation reaction. The product (13) was purified using protein A chromatography.

REFERENCES

The contents of all references cited herein are hereby incorporated by reference herein for all purposes.

1. Adams, G. P., and Weiner, L. M. (2005) Monoclonal antibody therapy of cancer. Nat. Biotechnol. 23, 1147-1157.
2. Aggarwal, S. R. (2012) What's fueling the biotech engine-2011 to 2012. Nat. Biotechnol. 30, 1191-1197.
3. Aggarwal, S. R. (2014) A survey of breakthrough therapy designations. Nat. Biotechnol. 32, 323-330.
4. Jefferis, R. (2009) Glycosylation as a strategy to improve antibody-based therapeutics. Nat. Rev. Drug Discov. 8, 226-234.
5. Dalziel, M., Crispin, M., Scanlan, C. N., Zitzmann, N., and Dwek, R. A. (2014) Emerging principles for the therapeutic exploitation of glycosylation. Science 343, 1235681.
6. van de Bovenkamp, F. S., Hafkenscheid, L., Rispens, T., and Rombouts, Y. (2016) The Emerging Importance of IgG Fab Glycosylation in Immunity. J. Immunol. 196, 1435-1441.
7. Le, N. P., Bowden, T. A., Struwe, W. B., and Crispin, M. (2016) Immune recruitment orsuppression by glycan engineering of endogenous and therapeutic antibodies. Biochim. Biophys. Acta. 1860, 1655-1668.
8. Niwa, R., Shoji-Hosaka, E., Sakurada, M., Shinkawa, T., Uchida, K., Nakamura, K., Matsushima, K., Ueda, R., Hanai, N., and Shitara, K. (2004) Defucosylated chimeric anti-CC chemokine receptor 4 IgG1 with enhanced antibody-dependent cellular cytotoxicity shows potent therapeutic activity to T-cell leukemia and lymphoma. *Cancer Res.* 64, 2127-2133.
9. Illidge, T., Cheadle, E. J., Donaghy, C., and Honeychurch, J. (2014) Update on obinutuzumab in the treatment of B-cell malignancies. *Expert Opin. Biol. Ther.* 14, 1507-1517.
10. Kaneko, Y., Nimmerjahn, F., and Ravetch, J. V. (2006) Anti-inflammatory activity of immunoglobulin G resulting from Fc sialylation. *Science* 313, 670-673.
11. Anthony, R. M., Nimmerjahn, F., Ashline, D. J., Reinhold, V. N., Paulson, J. C., and Ravetch, J. V. (2008) Recapitulation of IVIG anti-inflammatory activity with a recombinant IgG Fc. *Science* 320, 373-376.
12. Schwab, I., Mihai, S., Seeling, M., Kasperkiewicz, M., Ludwig, R. J., and Nimmerjahn, F. (2014) Broad requirement for terminal sialic acid residues and FcgammaRIIB for the preventive and therapeutic activity of intravenous immunoglobulins in vivo. *Eur. J. Immunol.* 44, 1444-1453.
13. Washburn, N., Schwab, I., Ortiz, D., Bhatnagar, N., Lansing, J. C., Medeiros, A., Tyler, S., Mekala, D., Cochran, E., Sarvaiya, H., Garofalo, K., Meccariello, R., Meador, J. W., 3rd, Rutitzky, L., Schultes, B. C., Ling, L., Avery, W., Nimmerjahn, F., Manning, A. M., Kaundinya, G. V., and Bosques, C. J. (2015) Controlled tetra-Fc sialylation of IVIg results in a drug candidate with consistent enhanced anti-inflammatory activity. *Proc. Natl. Acad. Sci. USA* 112, E1297-1306.
14. Umana, P., Jean-Mairet, J., Moudry, R., Amstutz, H., and Bailey, J. E. (1999) Engineered glycoforms of an anti-neuroblastoma IgG1 with optimized antibody-dependent cellular cytotoxic activity. *Nat. Biotechnol.* 17, 176-180.
15. Yamane-Ohnuki, N., Kinoshita, S., Inoue-Urakubo, M., Kusunoki, M., Iida, S., Nakano, R., Wakitani, M., Niwa, R., Sakurada, M., Uchida, K., Shitara, K., and Satoh, M. (2004) Establishment of FUT8 knockout Chinese hamster ovary cells: an ideal host cell line for producing completely defucosylated antibodies with enhanced antibody-dependent cellular cytotoxicity. *Biotechnol. Bioeng.* 87, 614-622.
16. Stanley, P., Sundaram, S., Tang, J., and Shi, S. (2005) Molecular analysis of three gain-of function CHO mutants that add the bisecting GlcNAc to N-glycans. *Glycobiology* 15, 43-53.
17. Cox, K. M., Sterling, J. D., Regan, J. T., Gasdaska, J. R., Frantz, K. K., Peele, C. G., Black, A., Passmore, D., Moldovan-Loomis, C., Srinivasan, M., Cuison, S., Cardarelli, P. M., and Dickey, L. F. (2006) Glycan optimization of a human monoclonal antibody in the aquatic plant *Lemna minor. Nat. Biotechnol.* 24, 1591-1597.
18. Strasser, R., Castilho, A., Stadlmann, J., Kunert, R., Quendler, H., Gattinger, P., Jez, J., Rademacher, T., Altmann, F., Mach, L., and Steinkellner, H. (2009) Improved virus neutralization by plant-produced anti-HIV antibodies with a homogeneous beta1,4-galactosylated N-glycan profile. *J. Biol. Chem.* 284, 20479-20485.
19. Li, H., Sethuraman, N., Stadheim, T. A., Zha, D., Prinz, B., Ballew, N., Bobrowicz, P., Choi, B. K., Cook, W. J., Cukan, M., Houston-Cummings, N. R., Davidson, R., Gong, B., Hamilton, S. R., Hoopes, J. P., Jiang, Y., Kim, N., Mansfield, R., Nett, J. H., Rios, S., Strawbridge, R., Wildt, S., and Gerngross, T. U. (2006) Optimization of humanized IgGs in glycoengineered *Pichia pastoris. Nat. Biotechnol.* 24, 210-215.
20. Zhou, Q., Shankara, S., Roy, A., Qiu, H., Estes, S., McVie-Wylie, A., Culm-Merdek, K., Park, A., Pan, C., and Edmunds, T. (2008) Development of a simple and rapid method for producing non-fucosylated oligomannose containing antibodies with increased effector function. *Biotechnol. Bioeng.* 99, 652-665.
21. Wang, L. X., and Amin, M. N. (2014) Chemical and chemoenzymatic synthesis of glycoproteins for deciphering functions. *Chem. Biol.* 21, 51-66.
22. Wei, Y., Li, C., Huang, W., Li, B., Strome, S., and Wang, L. X. (2008) Glycoengineering of human IgG1-Fc through combined yeast expression and in vitro chemoenzymatic glycosylation. *Biochemistry* 47, 10294-10304.
23. Zou, G., Ochiai, H., Huang, W., Yang, Q., Li, C., and Wang, L. X. (2011) Chemoenzymatic synthesis and Fcgamma receptor binding of homogeneous glycoforms of antibody Fc domain. Presence of a bisecting sugar moiety enhances the affinity of Fc to FcgammaIIIa receptor. *J. Am. Chem. Soc.* 133, 18975-18991.
24. Fan, S. Q., Huang, W., and Wang, L. X. (2012) Remarkable transglycosylation activity of glycosynthase mutants of Endo-D, an endo-beta-N-acetylglucosaminidase from *Streptococcus pneumoniae. J. Biol. Chem.* 287, 11272-11281.
25. Huang, W., Giddens, J., Fan, S. Q., Toonstra, C., and Wang, L. X. (2012) Chemoenzymatic glycoengineering of intact IgG antibodies for gain of functions. *J. Am. Chem. Soc.* 134, 12308-12318.
26. Quast, I., Keller, C. W., Maurer, M. A., Giddens, J. P., Tackenberg, B., Wang, L. X., Munz, C., Nimmerjahn, F., Dalakas, M. C., and Lunemann, J. D. (2015) Sialylation of IgG Fc domain impairs complement-dependent cytotoxicity. *J. Clin. Invest.* 125, 4160-4170.
27. Giddens, J. P., and Wang, L. X. (2015) Chemoenzymatic Glyco-engineering of Monoclonal Antibodies. *Methods Mol. Biol.* 1321, 375-387.
28. Lin, C. W., Tsai, M. H., Li, S. T., Tsai, T. I., Chu, K. C., Liu, Y. C., Lai, M. Y., Wu, C. Y., Tseng, Y. C., Shivatare, S. S., Wang, C. H., Chao, P., Wang, S. Y., Shih, H. W., Zeng, Y. F., You, T. H., Liao, J. Y., Tu, Y. C., Lin, Y. S., Chuang, H. Y., Chen, C. L., Tsai, C. S., Huang, C. C., Lin, N. H., Ma, C., Wu, C. Y., and Wong, C. H. (2015) A common glycan structure on immunoglobulin G for enhancement of effector functions. *Proc. Natl. Acad. Sci. USA* 112, 10611-10616.
29. Kurogochi, M., Mori, M., Osumi, K., Tojino, M., Sugawara, S., Takashima, S., Hirose, Y., Tsukimura, W., Mizuno, M., Amano, J., Matsuda, A., Tomita, M., Takayanagi, A., Shoda, S., and Shirai, T. (2015) Glycoengineered Monoclonal Antibodies with Homogeneous Glycan (M3, G0, G2, and A2) Using a Chemoenzymatic Approach Have Different Affinities for FcgammaRIIIa and Variable Antibody-Dependent Cellular Cytotoxicity Activities. *PLoS One* 10, e0132848.
30. Parsons, T. B., Struwe, W. B., Gault, J., Yamamoto, K., Taylor, T. A., Raj, R., Wals, K., Mohammed, S., Robinson, C. V., Benesch, J. L., and Davis, B. G. (2016) Optimal Synthetic Glycosylation of a Therapeutic Antibody. *Angew. Chem. Int. Ed.* 55, 2361-2367.
31. Liu, R., Giddens, J., McClung, C. M., Magnelli, P. E., Wang, L. X., and Guthrie, E. P. (2016) Evaluation of a glycoengineered monoclonal antibody via LC-MS analysis in combination with multiple enzymatic digestion. *MAbs* 8, 340-346.
32. Giddens, J. P., Lomino, J. V., Amin, M. N., and Wang, L. X. (2016) Endo-F3 Glycosynthase Mutants Enable Chemoenzymatic Synthesis of Core-fucosylated Triantennary Complex Type Glycopeptides and Glycoproteins. *J. Biol. Chem.* 291, 9356-9370.
33. Sjogren, J., Struwe, W. B., Cosgrave, E. F., Rudd, P. M., Stervander, M., Allhorn, M., Hollands, A., Nizet, V., and Collin, M. (2013) EndoS2 is a unique and conserved enzyme of serotype M49 group A *Streptococcus* that hydrolyses N-linked glycans on IgG and alphal-acid glycoprotein. *Biochem. J.* 455, 107-118.
34. Sjogren, J., Cosgrave, E. F., Allhorn, M., Nordgren, M., Bjork, S., Olsson, F., Fredriksson, S., and Collin, M. (2015) EndoS and EndoS2 hydrolyze Fc-glycans on therapeutic antibodies with different glycoform selectivity and can be used for rapid quantification of high-mannose glycans. *Glycobiology* 25, 1053-1063.
35. Shen, A., Lupardus, P. J., Morell, M., Ponder, E. L., Sadaghiani, A. M., Garcia, K. C., and Bogyo, M. (2009) Simplified, enhanced protein purification using an inducible, autoprocessing enzyme tag. *PloS One* 4, e8119.
36. Huang, W., Li, C., Li, B., Umekawa, M., Yamamoto, K., Zhang, X., and Wang, L. X. (2009) Glycosynthases enable a highly efficient chemoenzymatic synthesis of N-glycoproteins carrying intact natural N-glycans. *J. Am. Chem. Soc.* 131, 2214-2223.
37. Umekawa, M., Huang, W., Li, B., Fujita, K., Ashida, H., Wang, L. X., and Yamamoto, K. (2008) Mutants of *Mucor hiemalis* endo-beta-N-acetylglucosaminidase show enhanced transglycosylation and glycosynthase-like activities. *J. Biol. Chem.* 283, 4469-4479.
38. Umekawa, M., Li, C., Higashiyama, T., Huang, W., Ashida, H., Yamamoto, K., and Wang, L. X. (2010) Efficient glycosynthase mutant derived from *Mucor hiemalis* endo-beta-Nacetylglucosaminidase capable of transferring oligosaccharide from both sugar oxazoline and natural N-glycan. *J. Biol. Chem.* 285, 511-521.
39. Cartron, G., Dacheux, L., Salles, G., Solal-Celigny, P., Bardos, P., Colombat, P., and Watier, H. (2002) Therapeutic activity of humanized anti-CD20 monoclonal antibody and polymorphism in IgG Fc receptor FcgammaRIIIa gene. *Blood* 99, 754-758.
40. Shields, R. L., Lai, J., Keck, R., O'Connell, L. Y., Hong, K., Meng, Y. G., Weikert, S. H., and Presta, L. G. (2002) Lack of fucose on human IgG1 N-linked oligosaccharide improves binding to human Fcgamma RIII and antibody-dependent cellular toxicity. *J. Biol. Chem.* 277, 26733-26740.
41. Rodriguez-Diaz, J., Monedero, V., and Yebra, M. J. (2011) Utilization of natural fucosylated oligosaccharides by three novel alpha-L-fucosidases from a probiotic *Lactobacillus casei* strain. *Appl. Environ. Microbiol.* 77, 703-705.
42. Huang, W., Yang, Q., Umekawa, M., Yamamoto, K., and Wang, L. X. (2010) *Arthrobacter* endobeta-N-acetylglucosaminidase shows transglycosylation activity on complex-type N-glycan oxazolines: one-pot conversion of ribonuclease B to sialylated ribonuclease C. *ChemBioChem* 11, 1350-1355.
43. Wang, L. X., Ni, J., Singh, S., and Li, H. (2004) Binding of high-mannose-type oligosaccharides and synthetic oligomannose clusters to human antibody 2G12: implications for HIV-1 vaccine design. *Chem. Biol.* 11, 127-134.
44. Saribas, A. S., Johnson, K., Liu, L., Bezila, D., and Hakes, D. (2007) Refolding of human beta-1-2 GlcNAc transferase (GnT1) and the role of its unpaired Cys 121. *Biochem. Biophys. Res. Commun.* 362, 381-386.
45. Park, J. E., Lee, K. Y., Do, S. I., and Lee, S. S. (2002) Expression and characterization of beta-1,4-galactosyltransferase from *Neisseria meningitidis* and *Neisseria gonorrhoeae*. *J. Biochem. Mol. Biol.* 35, 330-336
46. Yu, H., Huang, S., Chokhawala, H., Sun, M., Zheng, H., and Chen, X. (2006) Highly efficient chemoenzymatic synthesis of naturally occurring and non-natural alpha-2, 6-linked sialosides: a *P. damsela* alpha-2,6-sialyltransferase with extremely flexible donor-substrate specificity. *Angew. Chem. Int. Ed.* 45, 3938-3944.
47. Allhorn M, Olsen A, Collin M: EndoS from *Streptococcus pyogenes* is hydrolyzed by the cysteine proteinase SpeB and requires glutamic acid 235 and tryptophans for IgG glycan-hydrolyzing activity. *BMC Microbiol* 2008, 8:3.
48. Collin M, Olsen A: EndoS, a novel secreted protein from *Streptococcus pyogenes* with endoglycosidase activity on human IgG. *EMBO J.* 2001, 20:3046-3055.
49 Strome S E, Sausville E A, Mann D: A mechanistic perspective of monoclonal antibodies in cancer therapy beyond target-related effects. *Oncologist* 2007, 12:1084-1095.

TABLE 1

Comparison of the specific hydrolysis activities of the Endo-S2 D184 mutants using a synthetic complex glycoform of rituximab as the substrate.

| Mutant | Specific hydrolysis activity *100 (umole/min/mg) | Percentage of specific hydrolysis activity % |
|---|---|---|
| WT | 11.185 | 100.000 |
| D184A | 0.750 | 6.701 |
| D184C | 1.386 | 12.392 |
| D184E | 0.879 | 7.855 |
| D184F | 0.000 | 0.000 |
| D184G | 1.249 | 11.168 |
| D184H | 0.000 | 0.000 |
| D184K | 0.000 | 0.000 |
| D184R | 0.000 | 0.000 |
| D184I | 0.033 | 0.295 |
| D184L | 0.045 | 0.405 |
| D184M | 0.158 | 1.410 |
| D184N | 0.842 | 7.526 |
| D184P | 0.340 | 3.043 |
| D184Q | 0.049 | 0.441 |
| D184S | 1.387 | 12.398 |
| D184T | 0.212 | 1.899 |
| D184V | 0.409 | 3.659 |
| D184W | 0.000 | 0.000 |
| D184Y | 5.526 | 49.406 |

TABLE 2

Comparison of the specific transglycosylation activity of Endo-S2 D184 mutants using sialoglycan oxazoline as donor substrate and deglycosylated rituximab as the acceptor substrate.

| Mutants | Specific transglycosylation activity *10 (umolmin/mg) | Percentage of specific transglycosylation activity % |
|---|---|---|
| WT | 1.712 | 44.31 |
| D184A | 1.023 | 26.46 |
| D184C | 3.864 | 100.00 |
| D184E | 2.006 | 51.907 |
| D184H | 0.044 | 1.14 |
| D184G | 2.270 | 58.73 |
| D184H | 0.026 | 0.68 |
| D184K | 0.021 | 0.54 |
| D184R | 0.022 | 0.57 |
| D184I | 0.066 | 1.71 |

TABLE 2-continued

Comparison of the specific transglycosylation activity of Endo-S2 D184 mutants using sialoglycan oxazoline as donor substrate and deglycosylated rituximab as the acceptor substrate.

| Mutants | Specific transglycosylation activity *10 (umolmin/mg) | Percentage of specific transglycosylation activity % |
|---|---|---|
| D184L | 0.099 | 2.55 |
| D184M | 2.866 | 74.18 |
| D184N | 0.879 | 22.75 |
| D184P | 0.160 | 4.13 |
| D184Q | 0.383 | 9.92 |
| D184S | 1.164 | 30.13 |
| D184T | 0.828 | 21.42 |
| D184V | 0.147 | 3.79 |
| D184W | 0.046 | 1.20 |
| D184Y | 1.198 | 30.99 |

That which is claimed is:

1. A *Streptococcus pyogenes* (serotype M49) Endoglycosidase-S2 (Endo-S2) Asp184 mutant enzyme selected from the group consisting of D184M (SEQ ID NO: 7), D184E (SEQ ID NO: 8), D184C (SEQ ID NO: 6), D184G (SEQ ID NO: 9), D184A (SEQ ID NO: 2), D184N (SEQ ID NO: 3), D184Q (SEQ ID NO: 4), D184S (SEQ ID NO: 16), and D184T (SEQ ID NO. 17), wherein the Endo-S2 Asp 184 mutant enzyme exhibits increased transglycosylation efficiency relative to a wild-type Endo-S2 enzyme.

2. A composition comprising at least a *Streptococcus pyogenes* (serotype M49) Endoglycosidase-S2 (Endo-S2) Asp 184 mutant enzyme selected from the group consisting of D184M (SEQ ID NO: 7), D184E (SEQ ID NO: 8), D184C (SEQ ID NO: 6), D184G (SEQ ID NO: 9), D184A (SEQ ID NO: 2), D184N (SEQ ID NO: 3), D184Q (SEQ ID NO: 4), D184S (SEQ ID NO: 16), and D184T (SEQ ID NO. 17) and optionally a buffer.

3. The composition according to claim 2, further comprising a decosylated glycoprotein, wherein the decosylated glycoprotein comprises a N-acetylglucosamine (GlcNAc) acceptor protein with a protein domain and wherein a GlcNAc residue is positioned closest to the protein domain.

4. The composition according to claim 3, wherein the decosylated glycoprotein is a fucosylated or nonfucosylated antibody or Fc-containing fragment thereof.

5. The composition according to claim 3, further comprising an activated oligosaccharide oxazoline donor having a predetermined number of saccharides.

6. The composition according to claim 5, wherein the activated oligosaccharide oxazoline donor is a synthetic oligosaccharide oxazoline or natural N-glycan (complex, high mannose, or hybrid) oxazoline.

7. The composition according to claim 6, wherein the synthetic oligosaccharide oxazoline is a di-, tri-, tetra-, penta-, hexyl-, hepta-, octyl-, nona-, deca- or undeca-saccharide oxazoline.

8. The composition according to claim 5, wherein the activated oligosaccharide oxazoline donor further comprises an additional biologically active agent or a tag.

9. The composition according to claim 4, wherein the fucosylated or nonfucosylated antibody is selected from the group consisting of 17b, 48d, A32, C11, 2G12, F240, IgG1b12, 19e, X5, TNX-355, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab, and MYO-029.

10. The composition according to claim 8, wherein the additional biologically active agent or tag is a drug, toxin, fluorescent probe, biotin, a PEG, lipid, or polypeptide.

11. The composition according to claim 3, wherein the N-acetylglucosamine (GlcNAc) acceptor protein is an alpha-1-6-fucosyl-GlcNAc-protein.

12. The composition according to claim 2, where in the *Streptococcus pyogenes* (serotype M49) Endo-S2 Asp 184 mutant enzyme is D184M (SEQ ID NO: 7), D184E (SEQ ID NO: 8), D184C (SEQ ID NO: 6), or D184G (SEQ ID NO: 9).

\* \* \* \* \*